(12) United States Patent
Sung et al.

(10) Patent No.: US 8,318,200 B1
(45) Date of Patent: *Nov. 27, 2012

(54) PHARMACEUTICAL COMPOSITION OF NANOPARTICLES

(75) Inventors: Hsing-Wen Sung, Hsinchu (TW); Zi-Xian Liao, Hsinchu (TW); Ko-Jie Chen, Hsinchu (TW); Cherng-Jyh Ke, Hsinchu (TW); Hosheng Tu, Newport Beach, CA (US)

(73) Assignee: GP Medical, Inc., Newport Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/462,699

(22) Filed: May 2, 2012

Related U.S. Application Data

(63) Continuation-in-part of application No. 12/928,121, filed on Dec. 3, 2010, now Pat. No. 8,198,246, which is a continuation-in-part of application No. 11/975,279, filed on Oct. 18, 2007, now Pat. No. 7,985,426, which is a continuation-in-part of application No. 11/328,552, filed on Jan. 10, 2006, now Pat. No. 7,304,045, which is a continuation-in-part of application No. 10/958,864, filed on Oct. 5, 2004, now Pat. No. 7,348,026.

(51) Int. Cl.
*A61K 9/127* (2006.01)
(52) U.S. Cl. ...................................... 424/450
(58) Field of Classification Search .................. 424/450
See application file for complete search history.

(56) References Cited

U.S. PATENT DOCUMENTS

| | | |
|---|---|---|
| 6,177,274 B1 | 1/2001 | Park et al. |
| 6,726,934 B1 | 4/2004 | Prokop |
| 7,244,449 B2 * | 7/2007 | Slater et al. ............ 424/450 |
| 8,187,571 B1 * | 5/2012 | Sung et al. ............. 424/1.73 |
| 2006/0051423 A1 | 3/2006 | Heppe et al. |

* cited by examiner

*Primary Examiner* — Maryam Monshipouri

(57) ABSTRACT

The invention discloses a pharmaceutical composition of liposome nanoparticles for lodging in a target tissue cell in situ of an animal subject, the nanoparticles comprising at least one thermal triggered phase-transition compound as a targeting drug delivery system for physical cancer therapy.

19 Claims, 22 Drawing Sheets

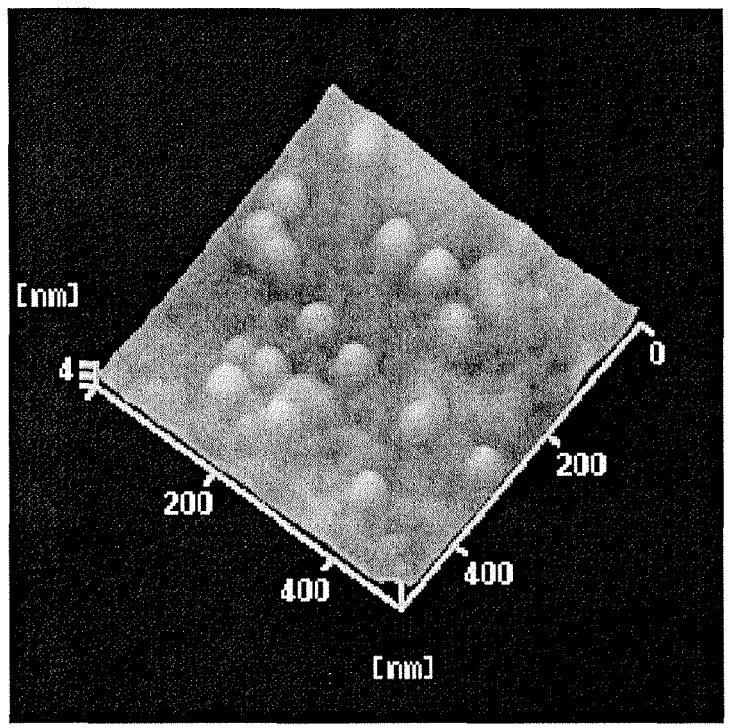
(A) P/C = 0/10
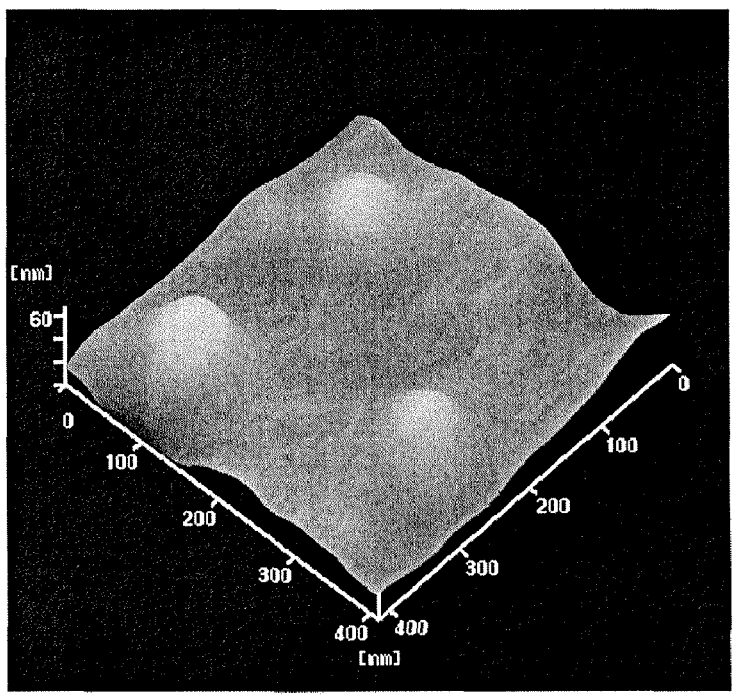
(B) P/C = 0.5/10
FIG. 4

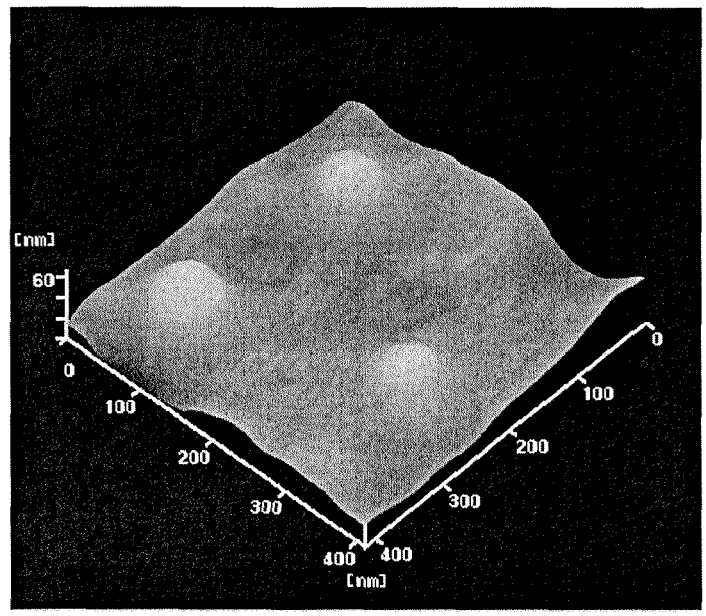
(C) P/C = 2/10
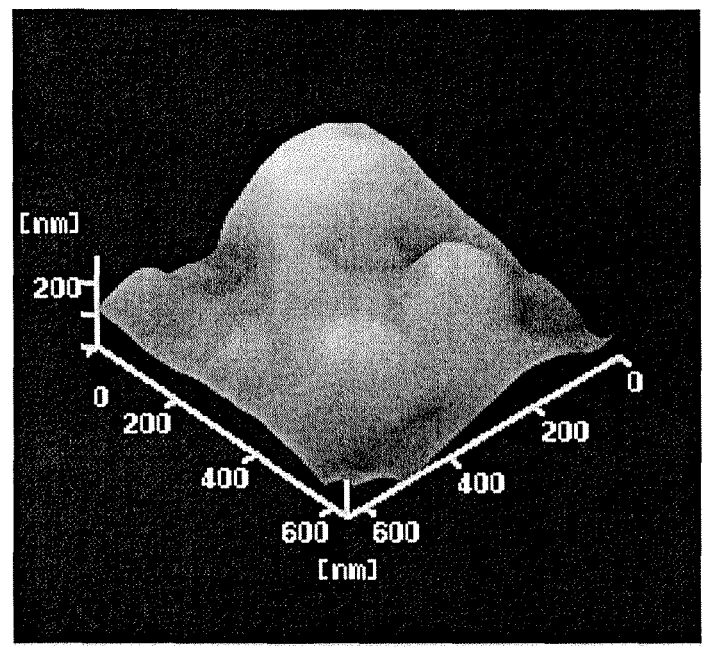
(D) P/C = 3/10
FIG. 4 (continued)

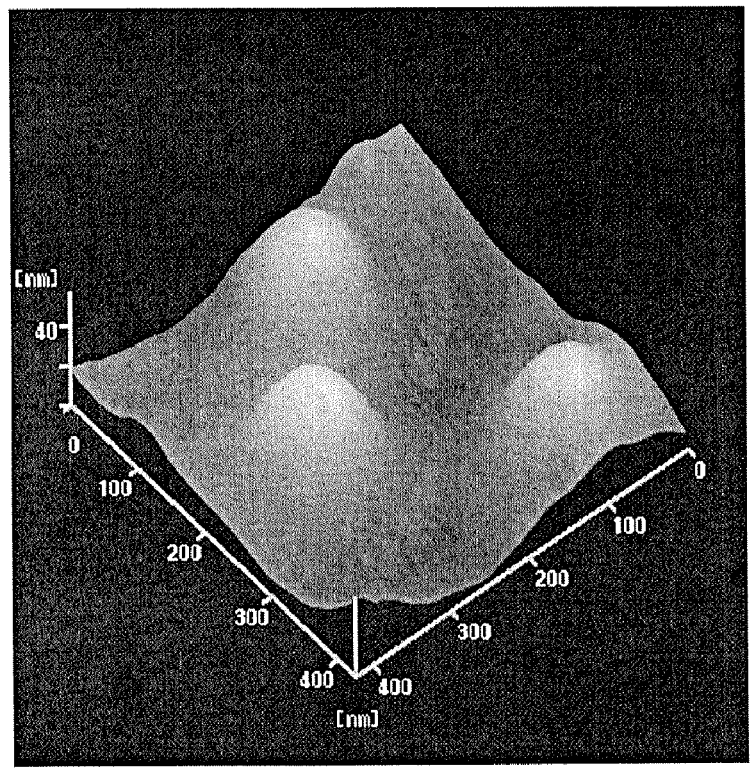
(E) P/C = 1/10
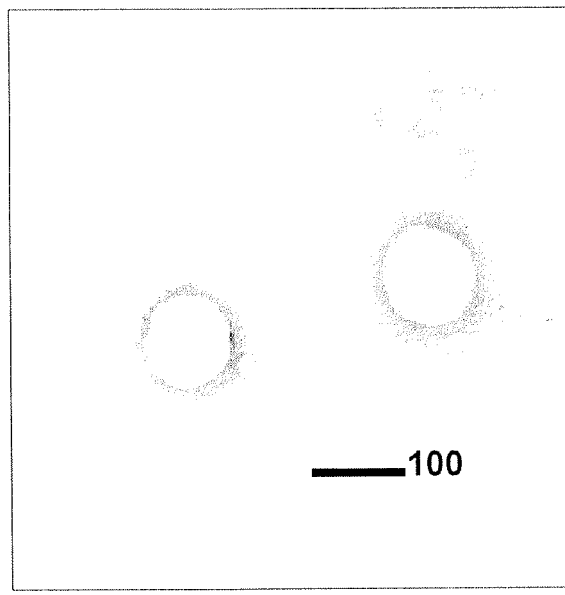
(F) P/C = 1/10
FIG. 4 (continued)

FIG. 7
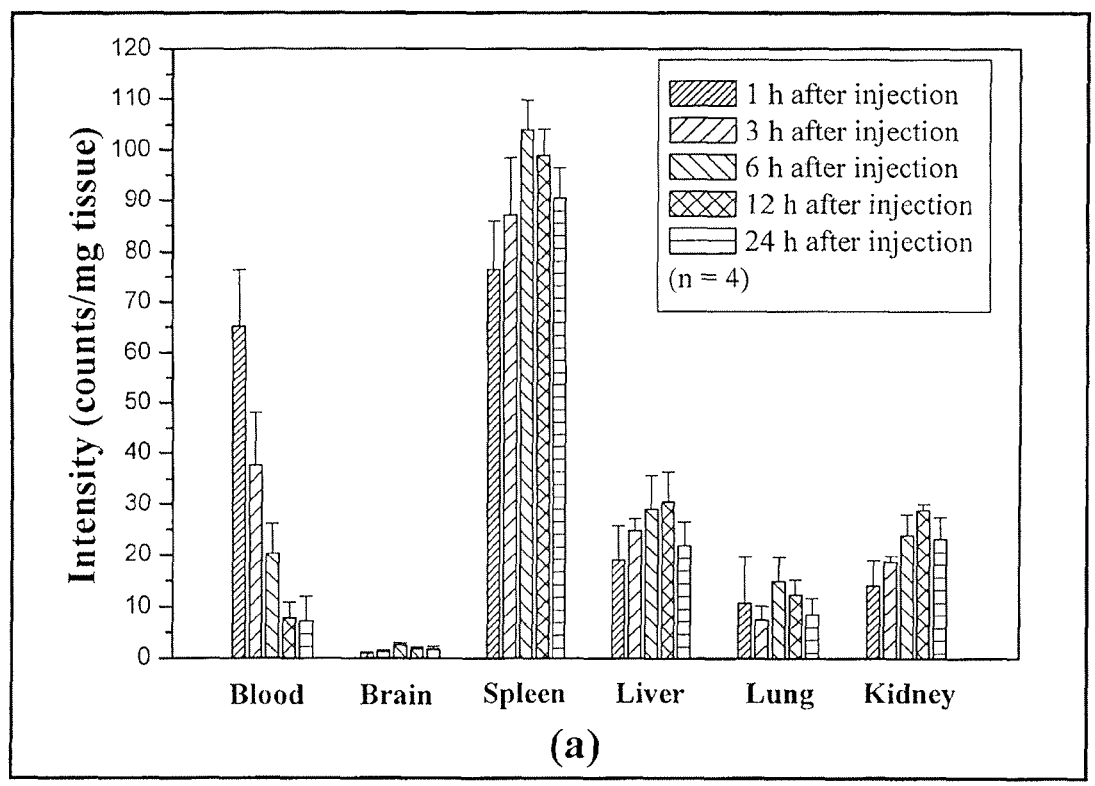
(a)
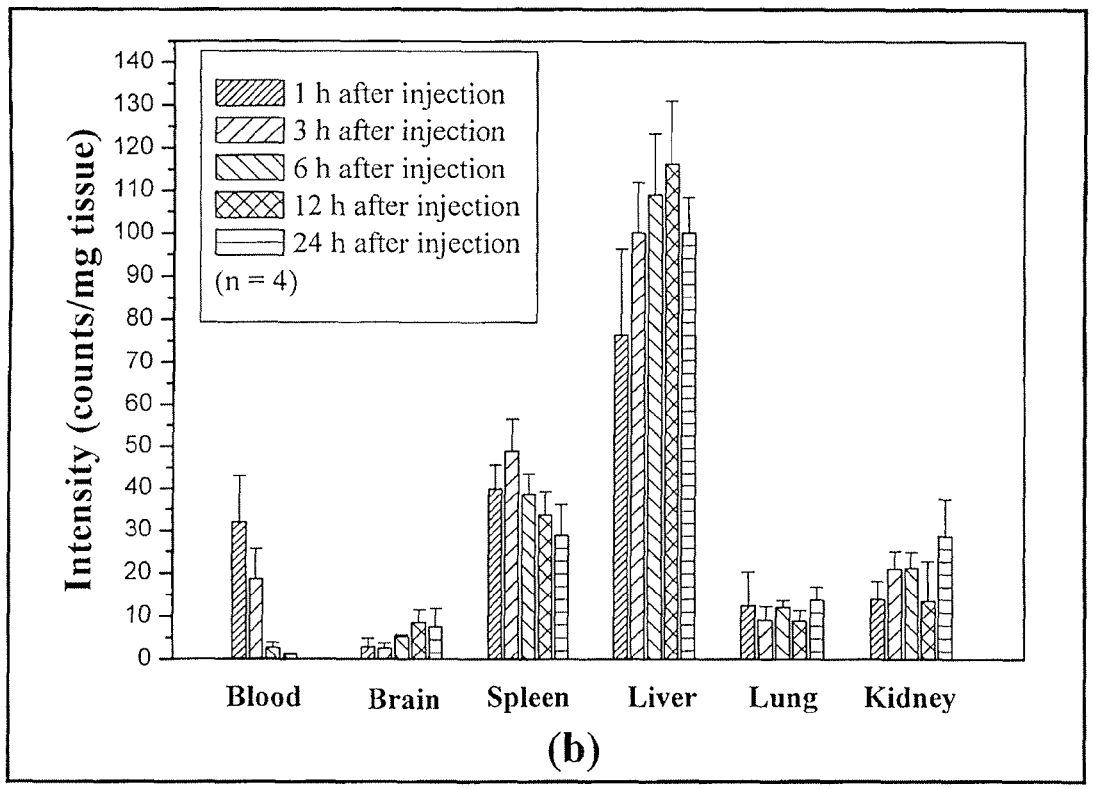
(b)

FIG. 8
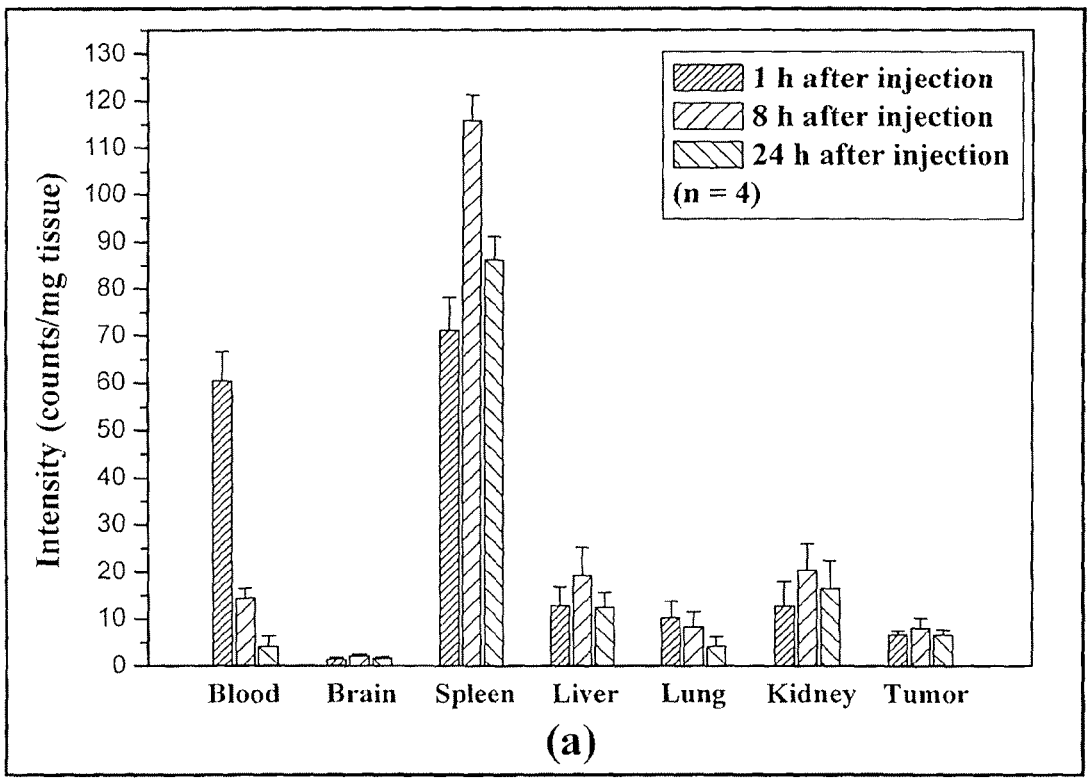
(a)
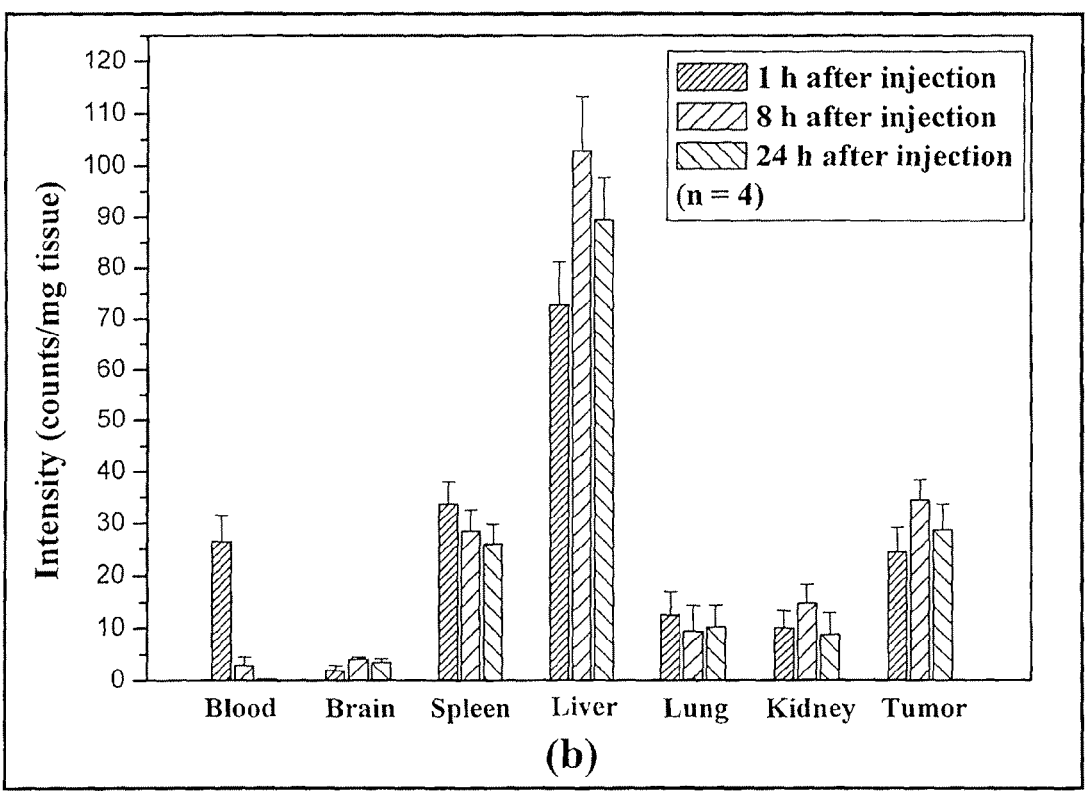
(b)

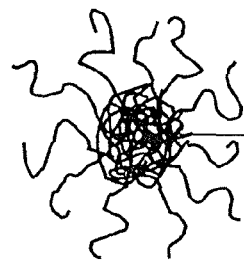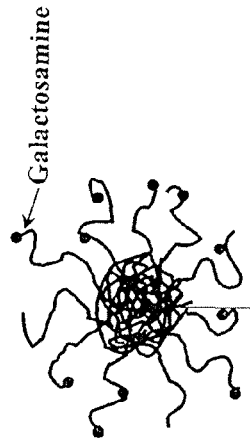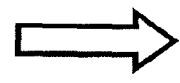
FIG. 10

Note: The symbol ⊞ denotes a liposome micelle that contains at least one thermal triggered phase-transition compound within the micelle FIG. 19 Endocytosis pathway

PHARMACEUTICAL COMPOSITION OF NANOPARTICLES

CROSS-REFERENCE TO RELATED APPLICATIONS

This application is a continuation-in-part application of U.S. patent application Ser. No. 12/928,121 filed Dec. 3, 2010, now U.S. Pat. No. 8,198,246, which is a continuation-in-part application of U.S. patent application Ser. No. 11/975,279 filed Oct. 18, 2007, now U.S. Pat. No. 7,985,426, which is a continuation-in-part application of U.S. patent application Ser. No. 11/328,552 filed Jan. 10, 2006, now U.S. Pat. No. 7,304,045, which is a continuation-in-part application of U.S. patent application Ser. No. 10/958,864 filed Oct. 5, 2004, now U.S. Pat. No. 7,348,026, the entireties of the priority documents are hereby incorporated by reference.

FIELD OF THE INVENTION

The present invention is related to a pharmaceutical composition of liposome nanoparticles composed of at least one thermal triggered phase-transition compound as a targeting drug delivery system for physical cancer therapy.

BACKGROUND OF THE INVENTION

Chemotherapy for cancers is usually limited by the toxicity of drugs to normal tissues. Additionally, short circulation half-life in plasma, limited aqueous solubility, and non-selectivity are usually encountered by most of the currently available anticancer drugs and thus restrict their therapeutic efficacy (Adv. Drug Deliver. Rev. 2002; 54:695-713). To reduce the toxicity and increase the therapeutic efficacy of anticancer drugs, various drug carriers, such as soluble polymers, polymeric nanoparticles, liposomes, and microspheres have been investigated (J. Control. Release 2000; 69:225-236; J. Control. Release 2003; 92:49-67; J. Biomed. Mater. Res. 2003; 65A:271-282). The hydrophilic shell-forming block determines surface properties of the nanoparticles and influences interactions between the surrounding environments and the nanoparticles (Biomaterials 2003; 24:2053-2059).

Nanoparticles may be delivered to specific sites by size-dependant passive targeting or by active targeting (Cancer Res. 1986; 46:6387-6392; J. Control. Release 1999; 62:253-262). To obtain a high degree of selectivity to a specific organ and to enhance the uptake of drug-loaded nanoparticles into the target cells, active targeting has been attempted. Liver has been one of the most desirable target organs in the body due to various liver-related metabolic and infectious diseases and cancers (Int. J. Pharm. 1999; 188:39-47). The asialoglycoprotein (ASGP) receptor is known to be present on hepatocytes and several human hepatoma cell lines (Adv. Drug Deliver. Rev. 1989; 4:49-63). Therefore, liver targeting is achieved by designing drug delivery systems conjugated with a ligand that can bind to the ASGP receptors.

Poly(lactide) (PLA), poly(ε-caprolactone) (PCL), poly(β-benzyl L-aspartate) (PLBA), and poly(γ-benzyl L-glutamate) (PLBG) have been used mostly for the core-forming hydrophobic segment of nanoparticles (J. Control. Release 2004; 94:323-335). On the other hand, poly(ethylene oxide) (PEO), a non-toxic and highly hydrated polymer, has been used as the outer shell segment of nanoparticles because of its superior biocompatibility (J. Control. Release 2004; 94:323-335). In the present invention, PLA was used for the hydrophobic segment of the block copolymer, while a natural compound [poly(γ-glutamic acid), γ-PGA], produced as capsular substance or as slime by members of the genus *Bacillus*, was used as the hydrophilic segment.

γ-PGA is unique in that it is composed of naturally occurring L-glutamic acid linked together through amide bonds rather than a nondegradable C—C backbone such as PEO. It was reported that this naturally occurring γ-PGA is a water-soluble, biodegradable, and non-toxic polymer (Crit. Rev. Biotechnol. 2001; 21:219-232). A related, but structurally different, polymer poly(α-glutamic acid), (α-PGA) is usually synthesized from poly(γ-benzyl-L-glutamate) by removing the benzyl protecting group with the use of hydrogen bromide (Adv. Drug Deliver. Rev. 2002; 54:695-713). Li et al. conjugated paclitaxel onto α-PGA via covalent bonding to form a new drug formulation (Cancer Res. 1998; 58:2404-2409). Their pre-clinical data suggested that the uptake of α-PGA-paclitaxel by tumor cells was about 5-fold greater than that of paclitaxel. Additionally, α-PGA-paclitaxel had a significantly longer circulation half-life in plasma than paclitaxel (Adv. Drug Deliver. Rev. 2002; 54:695-713). For the potential of targeting liver cancer cells, the prepared nanoparticles are further conjugated with galactosamine. Hashida et al. reported using α-PGA as a polymeric backbone and galactose moiety as a ligand to target hepatocytes (J. Control. Release 1999; 62:253-262). Their in vivo results indicated that the galactosylated α-PGA had a remarkable targeting ability to hepatocytes and degradation of α-PGA was observed in the liver. The internalization efficiency of the prepared nanoparticles with or without galactosamine conjugated into HepG2 cells (a liver cancer cell line) was examined in vitro using a confocal laser scanning microscope.

Liver cancer is a common lethal disease in Asia (Br J Cancer 1998; 78:34-39). It is also the ninth leading cause of cancer deaths in the United States (Cancer Lett. 1999; 136:109-118). It is known that chemotherapy for cancers is usually limited by the toxicity of drugs to normal tissues (Adv. Drug Deliver. Rev. 2002; 54:695-713). The self-assembled nanoparticles, composed of amphiphilic block copolymers, have a hydrophobic inner core and a hydrophilic outer shell. In a co-pending application U.S. Ser. No. 10/958,864, filed Oct. 5, 2004, it is disclosed that poly(γ-glutamic acid) (abbreviated as γ-PGA) and poly(lactide) (abbreviated as PLA) are used to synthesize amphiphilic block copolymers via a simple coupling reaction between γ-PGA and PLA to prepare a novel type of self-assembled nanoparticles (J. Control. Release 2005; 105:213-225). No aggregation or precipitation of the nanoparticles was observed during storage for up to 1 month, because of the electrostatic repulsion between the negatively charged nanoparticles (J. Control. Release 2005; 105:213-225). γ-PGA, produced by certain *Bacillus* species, is a naturally occurring anionic homo-polyamide that is made of L-glutamic acid units connected by amide linkages between α-amino and γ-carboxylic acid groups (Crit. Rev. Biotechnol. 2001; 21:219-232). Because of its water-solubility, biodegradability, edibility, and non-toxicity toward humans, several applications of γ-PGA in food, cosmetics, and medicine have been investigated in the past few years.

Owing to its unique structure, paclitaxel readily enters mammalian cells and preferentially binds to tubulin in polymerized microtubules (J. Biol. Chem. 1995; 270:20235-20238). This binding stabilizes microtubules and greatly interferes with microtubular reorganization necessary, among other factors, for spindle formation and cell division (Cancer Lett. 1999; 136:109-118). Thus, exposure of susceptible cells to paclitaxel has been shown to initially cause arrest in the G2/M phase and finally to cell death through apoptotic mechanisms (Cancer Res. 1996; 56:816-825).

Most chemotherapy drugs are generally taken up nonspecifically by all types of cells resulting in serious side effects. Physical cancer therapy, such as radiofrequency ablation, has less side effects but it is difficult to target the specific tumor site or the in vivo range of heating. Therefore, patients may have a recurrence of cancer.

Liposomes have good biocompatibility and can carry hydrophobic or hydrophilic drug. Liposomes can carry the thermal sensitive compound (also known as thermal triggered phase-transition compound), such as $NH_4HCO_3$, which is able to generate $CO_2$ by heat to an elevated temperature in situ to rapidly blow up the liposomes inside a cell. In general, cells would be little damaged if the cell temperature were maintained lower than about 42° C.

There is, therefore, a clinical need for providing a pharmaceutical composition of biodegradable liposome nanoparticles composed of at least one thermal triggered phase-transition compound to abruptly cause physical damage of cancer cells as means for physical cancer therapy. Furthermore, the liposome nanoparticles may further comprise a cancer drug as means for a dual physical and biochemical cancer treatment.

SUMMARY OF THE INVENTION

Some aspects of the invention provide a liposome nanoparticle or micelle or a pharmaceutical composition of liposome nanoparticles or micelles, the nanoparticle/micelle comprising liposome and at least one thermal triggered phase-transition compound. In one embodiment, the liposome micelle is a micelle with liposome dominating on the outer surface. In another embodiment, the outer surface is positively charged. In still another embodiment, the liposome micelle further comprises at least one anticancer drug (for example, paclitaxel), chemotherapy components (for example, doxorubicin and cyclophosphamide for treating breast cancer), and/or cancer targeting moiety (for example, galactosamine toward hepatoma cells).

Some aspects of the invention provide a pharmaceutical composition of nanoparticles, the nanoparticles consisting of a positively charged chitosan, a negatively charged substrate, optionally a zero-charge compound, and liposome micelles that contains at least one thermal triggered phase-transition compound, such as ammonium bicarbonate.

Some aspects of the invention provide a pharmaceutical composition of liposome nanoparticles loaded with at least one thermal triggerable phase-transition compound that are adapted for delivery to a blood vessel of the animal subject. In one embodiment, the liposome nanoparticles are further loaded with at least one bioactive agent. Basically, the liposome portion of the liposome nanoparticles of the present invention is relatively thermal insensitive whereas the active content portion of the thermal triggerable phase-change compound of the liposome nanoparticles is highly thermal sensitive. In one embodiment, the liposome portion of the liposome nanoparticles is less thermal sensitive than the thermal triggerable phase-change compound of the liposome nanoparticles.

Some aspects of the invention provide a process for preparing self-assembled nanoparticles using poly(γ-glutamic acid) (γ-PGA) and poly(lactide) (PLA) to synthesize block copolymers via a simple coupling reaction between γ-PGA and PLA. In a further embodiment for targeting liver cancer cells, galactosamine is further conjugated on the prepared nanoparticles as a targeting moiety. γ-PGA, a water-soluble, biodegradable, and non-toxic compound, was produced by microbial fermentation (*B. licheniformis*, ATCC 9945a) and then was hydrolyzed. The hydrolyzed γ-PGA with a molecular weight of 4 kDa and a polydispersity index of 1.3 was used, together with PLA (10 kDa, polydispersity index 1.1), to synthesize block copolymers. The prepared nanoparticles had a mean particle size of about 140 nm with a zeta potential of about −20 mV. One object of the invention provides a process for preparing self-assembled nanoparticles using poly(glutamic acid) (PGA) and poly(lactide) (PLA) to synthesize block copolymers via a simple coupling reaction between PGA and PLA. In one embodiment, the PGA is selected from the group consisting of γ-PGA, α-PGA, water-soluble salts of PGA, metal salts of PGA. In a further embodiment for targeting liver cancer cells, galactosamine is further conjugated on the prepared nanoparticles as a targeting moiety.

Some aspects of the invention relate to a compound or dose for treating liver cancers in a patient comprising nanoparticles composed of γ-PGA-PLA block copolymers conjugated with galactosamine. In a further embodiment, the compound or the dose comprises a therapeutically effective amount of the nanoparticles.

Some aspects of the invention relate to a compound or pharmaceutical composition for treating liver cancers in a patient comprising of nanoparticles composed of γ-PGA-PLA block copolymers, wherein the nanoparticles are loaded with at least one bioactive agent.

Some aspects of the invention relate to a compound or pharmaceutical composition for treating liver cancers in a patient comprising nanoparticles composed of γ-PGA-PLA block copolymers conjugated with galactosamine, wherein the nanoparticles are loaded with at least one bioactive agent.

Some aspects of the invention relate to a compound or pharmaceutical composition for treating liver cancers in a patient comprising nanoparticles composed of γ-PGA-PLA block copolymers configured for targeting tissue cells, wherein the nanoparticles are loaded with at least one bioactive agent of DNA, RNA or siRNA. In one embodiment, the γ-PGA-PLA block copolymers are conjugated with galactosamine for targeting liver tissue cells. In another embodiment, the γ-PGA-PLA block copolymers are conjugated with a tissue-specific targeting moiety for that specific tissue.

In one embodiment, the nanoparticles are mixed in a solution with a nanoparticle concentration of up to 100 μg/ml. In one embodiment, a γ-PGA component prior to polymerization for forming the γ-PGA-PLA block copolymers has a molecular weight of about 4 kDa with a polydispersity index of about 1.3. In another embodiment, the nanoparticles comprise a hydrophobic inner core and a hydrophilic outer shell.

In one embodiment, a mean particle size for the nanoparticles in the compound or dose is in the range of about 10 to 500 nm, preferably in the range of about 50 to 200 nm, and most preferably in the range of about 100 to 150 nm.

In one embodiment, the bioactive agent associated with the nanoparticles of the present invention comprises an anticancer drug or is selected from the group consisting of doxorubicin, adriamycin, cisplatin, taxol, and 5-fluorouracil. In another embodiment, the bioactive agent associated with the nanoparticles of the present invention is selected from the group consisting of epipodophyllotoxins, camptothecins, endiyne antibiotics, taxanes, coformycins, anthracycline glycosides, mytomycin, combretastatin, anthrapyrazoles, and polyamine biosynthesis inhibitors.

Some aspects of the invention relate to a dual-particle tumor targeting system comprising a first ligand-mediated targeting nanoparticle(s) and a second EPR-mediated targeting nanoparticle(s), wherein the first and second nanoparticles are mixed in a solution delivering to the target tumor. In one embodiment, the first nanoparticle alone or the second nanoparticle alone is not cytotoxic to a cell. In another embodiment, the co-location of the first nanoparticle and the second nanoparticle in the tumor cell kills or inactivates the cell. In one embodiment, the nanoparticle-containing solution is configured and adapted for intravenous or intra-arterial injection for treating the tumor or cancer in a patient.

In one embodiment, the first or second nanoparticle of the dual-particle tumor targeting system is biodegradable. In another embodiment, the first or second nanoparticle of the dual-particle tumor targeting system comprises γ-PGA-PLA block copolymers. In a further embodiment, the first nanoparticle is conjugated with galactosamine and/or further comprises a pro-drug ganciclovir or a radiotracer.

In one embodiment, the second nanoparticle of the dual-particle tumor targeting system comprises HSV thymidine kinase gene. In another embodiment, the second nanoparticle of the dual-particle tumor targeting system further comprises matrix metalloproteinases, or an endothelial cells specific promoter selected from a group consisting of VEGF receptor-2 promoter, $α_vβ_3$ integrin promoter, and bFGF receptor promoter. In an alternate embodiment, the second nanoparticle comprises EC-specific promoter and HSV-TK gene constructed plasmid.

In one embodiment, the first and second nanoparticles of the dual-particle tumor targeting system are mixed in a solution with a nanoparticle concentration of up to 100 μg/ml in the solution. In one embodiment, the first or second nanoparticle is loaded with at least one bioactive agent. In one embodiment, the first nanoparticle, second nanoparticle, or both comprise a hydrophobic inner core and a hydrophilic outer shell.

Some aspects of the invention relate to a method for selectively inhibiting angiogenesis within a tumor, the method comprising delivering a dose of combined EC-specific promoters and HSV-TK genes to the tumor. In one embodiment, the tumor is hepatoma. In another embodiment, the dose is loaded within a nanoparticle(s). In still another embodiment, the dose further comprises a first ligand-mediated targeting nanoparticle(s), and wherein the EC-specific promoters and HSV-TK genes are loaded within a second nanoparticle(s).

It is one object of the present invention to provide a nanoparticle system and a method for administering DNA, RNA (including short interfering, double-stranded, micro or short hairpin RNA) into an animal subject. In one embodiment, the administration is via injection into a blood vessel through a vein or an artery.

The invention provides a nanoparticle system comprising compounds, compositions, and methods useful for modulating the expression of genes, such as those genes associated with angiogenesis and proliferation, using short interfering RNA molecules. Some aspects of the invention further provide a nanoparticle system that comprises compounds, compositions, and methods useful for modulating the expression and activity of vascular endothelial growth factor (VEGF) and/or vascular endothelial growth factor receptor (e.g., VEGFr1, VEGFr2, VEGFr3) genes, or genes involved in VEGF and/or VEGFr pathways of gene expression and/or VEGF activity by RNA interference (RNAi) using small nucleic acid molecules.

Some aspects of the invention provide a nanoparticle system used in the method of administering the siNA in an animal subject by transcutaneous injection or injection through a vein or an artery, the nanoparticle system comprising chemically synthesized double stranded short interfering nucleic acid (siNA) molecule that directs cleavage of a vascular endothelial growth factor receptor 1 (VEGEr1) RNA via RNA interference (RNAi).

Some aspects of the invention provide a pharmaceutical composition of nanoparticles for lodging in a target tissue of an animal subject, each nanoparticle comprising a first component of a positively charged chitosan, a second component of negatively charged substrate that complexes with the first positively charged component, and at least one bioactive agent encapsulated within the nanoparticles. In one embodiment, the nanoparticles are biodegradable. In another embodiment, the nanoparticle is about 50 μm to 500 μm in size.

In one preferred embodiment, the lodging of a nanoparticle in a target tissue is promoted/facilitated or enhanced by incorporating ligand-mediated targeting moiety (agent) in the nanoparticle. By ways of illustration, nanoparticle is conjugated with proteins or ligands (for example, galactosamine) that bind to the surface receptor (for example, ASGP Receptor) of hepatocyte (normal cells) and/or hepatocyte-derived cell lines such as hepatoma (abnormal cells). The nanoparticles would be swallowed up by receptor-mediated endocytosis of those cells. This is referred to as "ligand-mediated specific cell targeting" and may be used to lodge DNA, RNA into target tissue cells via a ligand-receptor binding mechanism for the ligand to bind a surface receptor of the cells.

One aspect of the invention provides a pharmaceutical composition of nanoparticles for lodging in a target tissue of an animal subject, each nanoparticle comprising a first component of a positively charged chitosan, a second component of negatively charged substrate that complexes with the first positively charged component, wherein the second component comprises a material selected from the group consisting of γ-PGA, α-PGA, PGA derivatives, glycosaminoglycans, and alginate, and a third component of ligand-mediated targeting moiety. In one embodiment, the second component comprises heparin.

Some aspects of the invention provide a pharmaceutical composition of nanoparticles for lodging in a target tissue cell in situ of an animal subject, the nanoparticles comprising poly(glutamic acid)-poly(lactide)_block copolymers that are conjugated with a ligand, wherein the ligand has ligand-receptor binding affinity for the ligand to bind a surface receptor of the tissue cell. In one embodiment, the ligand comprises a receptor-antagonist ligand. In this case, the ligand functions as a targeting medium (with little biological function) whereas the encapsulated bioactive agent reveals desired biological or biochemical functions. In another embodiment, the PGA is selected from the group consisting of γ-PGA, α-PGA, water-soluble salts of PGA, metal salts of PGA.

One aspect of the invention provides a pharmaceutical composition of nanoparticles for lodging in (or attracting to via the conjugated ligand) a target tissue cell in situ (or in vivo) of an animal subject, the nanoparticles comprising PGA-PLA block copolymers that are conjugated with a ligand, wherein the target tissue cell comprises a liver cell, a tumor or cancer cell.

One aspect of the invention provides a pharmaceutical composition of nanoparticles for lodging in a target tissue cell of an animal subject further comprising at least one bioactive agent, wherein the bioactive agent encapsulated within the nanoparticles is a protein or a peptide.

One aspect of the invention provides a pharmaceutical composition of nanoparticles for lodging in a target tissue cell of an animal subject further comprising at least one bioactive agent, wherein the bioactive agent encapsulated within the nanoparticles is plasmid protein.

One aspect of the invention provides a pharmaceutical composition of nanoparticles for lodging in a target tissue cell of an animal subject further comprising at least one bioactive agent, wherein the bioactive agent encapsulated within the nanoparticles comprises a ribonucleic acid.

One aspect of the invention provides a pharmaceutical composition of nanoparticles for lodging in a target tissue cell of an animal subject further comprising at least one bioactive agent, wherein the bioactive agent encapsulated within the nanoparticles is a deoxyribonucleic acid.

One aspect of the invention provides a pharmaceutical composition of nanoparticles for lodging in a target tissue cell of an animal subject further comprising at least one bioactive agent, wherein the bioactive agent encapsulated within the nanoparticles comprises a small interfering ribonucleic acid.

One aspect of the invention provides a pharmaceutical composition of nanoparticles for lodging in a target tissue cell of an animal subject further comprising at least one bioactive agent, wherein the bioactive agent encapsulated within the nanoparticles comprises a growth factor.

One aspect of the invention provides a pharmaceutical composition of nanoparticles for lodging in a target tissue cell of an animal subject further comprising at least one bioactive agent, wherein the bioactive agent encapsulated within the nanoparticles comprises paclitaxel.

One aspect of the invention provides a pharmaceutical composition of nanoparticles for lodging in a target tissue cell of an animal subject further comprising at least one bioactive agent, wherein the nanoparticle is mixed with trehalose in a freeze-drying process.

One aspect of the invention provides a pharmaceutical composition of nanoparticles for lodging in a target tissue cell of an animal subject further comprising at least one bioactive agent, wherein the nanoparticle is mixed with hexan-1,2,3,4,5,6-hexyl in a freeze-drying process.

One aspect of the invention provides a pharmaceutical composition of nanoparticles for lodging in a target tissue cell of an animal subject, wherein the nanoparticle is crosslinked or partially crosslinked.

One aspect of the invention provides a pharmaceutical composition of nanoparticles for lodging in a target tissue cell of an animal subject, wherein the nanoparticle further comprises an adenovirus vector, the adenovirus vector comprising a small interfering ribonucleic acid. One aspect of the invention provides a pharmaceutical composition of nanoparticles for lodging in a target tissue cell of an animal subject, wherein a surface of the nanoparticle is positively charged. In an alternate embodiment, the surface of the nanoparticle is negatively charged.

Some aspects of the invention provide a method of treating a cancer or tumor cell of an animal subject, comprising steps of: (a) providing a pharmaceutical composition of nanoparticles, wherein the nanoparticles comprise liposomes and at least one thermal triggered phase-transition compound; (b) lodging the nanoparticles in the cancer or tumor cell in situ of the animal subject; and (c) supplying thermal energy to the at least one thermal triggered phase-transition compound, wherein the thermal energy is sufficient to cause a phase transition of the thermal triggered phase-transition compound, thereby causing the liposomes to rupture.

Some aspects of the invention provide a method of treating a cancer or tumor cell by providing a pharmaceutical composition of liposome nanoparticles of the present invention to an animal subject, wherein the liposome comprises HSPC (L-α-phosphatidylcholine, hydrogenated), DOTMA (N-[1-(2,3-dioleyloxy)propyl]-N,N,N-trimethylammonium chloride), and cholesterol. In one embodiment, the thermal triggered phase-transition compound is ammonium bicarbonate. In one embodiment, the nanoparticles are adapted for delivery to a blood vessel of the animal subject. In another embodiment, the lodging step is via an endocytosis pathway.

Some aspects of the invention provide a method of treating a cancer or tumor cell by providing a pharmaceutical composition of liposome nanoparticles of the present invention to an animal subject and supplying thermal energy to the at least one thermal triggered phase-transition compound, the thermal energy is supplied via a radiofrequency energy source, via an ultrasonic energy source, via a high-intensity focused ultrasound, or via an electromagnetic energy source. In one embodiment, the duration of the thermal energy supplied to the compound is within 60 minutes, preferably within 30 minutes, and most preferably within 10 minutes.

Some aspects of the invention provide a composition of liposome nanoparticles, comprising at least one antitumor or anticancer agent and a thermal triggerable phase-transition compound, wherein said thermal triggerable phase-transition compound is selected from the group consisting of ammonium bicarbonate, ammonium sulfate, ammonium citrate, ammonium acetate, ammonium carbonate, and ammonium sesquecarbonate. In one embodiment, the liposome comprises HSPC (L-α-phosphatidylcholine, hydrogenated), DOTMA (N-[1-(2,3-dioleyloxy)propyl]-N,N,N-trimethylammonium chloride), and cholesterol. In another embodiment, at least a portion of the nanoparticles comprises a hydrophilic outer shell or a hydrophobic outer shell.

Some aspects of the invention provide liposome nanoparticles that are adapted for delivery to a blood vessel of an animal subject. In one embodiment, the liposome nanoparticles enter cells of the animal subject via an endocytosis pathway. In one embodiment, the at least one anticancer agent is paclitaxel, a chemotherapy component, doxorubicin, camptothecin, or daunorubicin. In a further embodiment, the liposome nanoparticles further comprise at least one bioactive agent, wherein the at least one bioactive agent is a cancer targeting moiety, a deoxyribonucleic acid, or a small interfering ribonucleic acid. In one embodiment, the at least one antitumor or anticancer agent is loaded into the liposome nanoparticles via a concentration gradient of the compound across a liposomal layer.

Some aspects of the invention provide a thermal triggerable compound having a phase-transitional temperature above 40° C. or above about 40° C. In one embodiment, thermal energy is supplied to raise the phase-transitional temperature of the compound inside the liposome nanoparticles, wherein the thermal energy is supplied via a source selected from the group consisting of radiofrequency energy, ultrasonic energy, high-intensity focused ultrasound energy, electromagnetic energy, and hot saline energy. In one embodiment, a duration of the thermal energy supplied to the compound is within 30 minutes. In another embodiment, the compound is a sublimable compound. In one embodiment, the liposome nanoparticles have a size less than about 300 nanometers.

BRIEF DESCRIPTION OF THE DRAWINGS

FIGS. 4A-4F show morphology of the nanoparticles prepared with varying feed weight ratios of paclitaxel to block copolymer (the P/C ratio) obtained by the AFM and TEM.

FIG. 7 shows biodistributions of the nanoparticles loaded with rhodamine 123 (a) without galactosamine conjugated (the NPs) and (b) with galactosamine conjugated (the Gal-NPs) in normal mice.

FIG. 8 shows biodistributions of the nanoparticles loaded with rhodamine 123 (a) without galactosamine conjugated (the NPs) and (b) with galactosamine conjugated (the Gal-NPs) in hepatoma-tumor-bearing nude mice.

FIG. 10 shows a dual-particle tumor targeting system comprising a first ligand-mediated targeting nanoparticle and a second EPR mediated targeting nanoparticle.

DETAILED DESCRIPTION OF THE EXEMPLARY EMBODIMENTS

Figure 1:
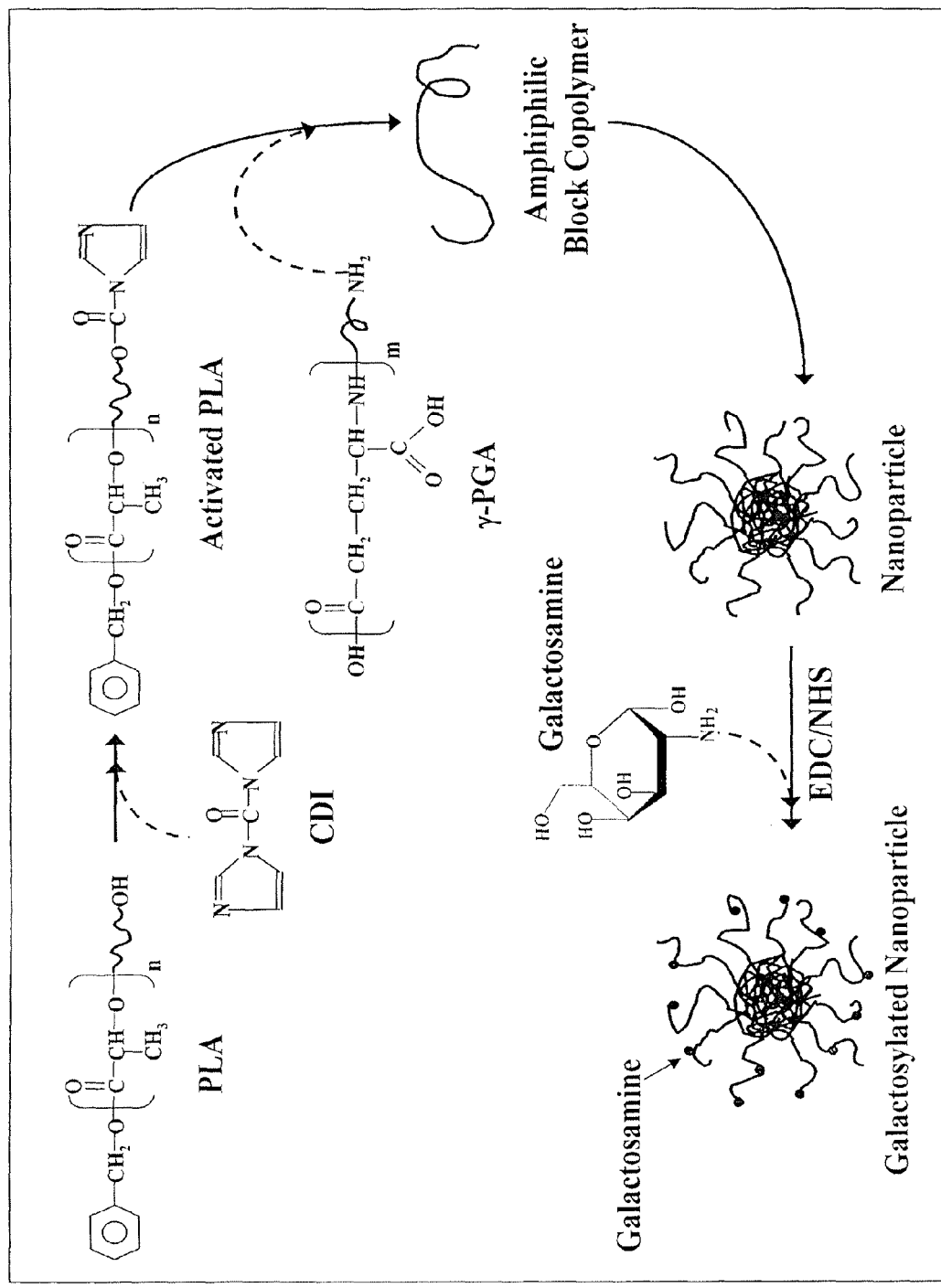
FIG. 1 shows schematic illustrations of synthesis of γ-PGA-PLA block copolymers and formation of self-assembled nanoparticles with galactosamine conjugated.

The preferred embodiments of the present invention described below relate particularly to preparation of liposome micelles comprising at least one thermal triggered phase-transition compound. In a further embodiment, the nanoparticles of the present invention relate to poly(γ-glutamic acid)-poly(lactide) block copolymers conjugated with galactosamine and/or further loaded with paclitaxel for HepG2 cells uptake, with optionally loaded liposome micelles. While the description sets forth various embodiment specific details, it will be appreciated that the description is illustrative only and should not be construed in any way as limiting the invention. Furthermore, various applications of the invention, and modifications thereto, which may occur to those who are skilled in the art, are also encompassed by the general concepts described below.

Over the past few decades, biodegradable nanoparticles composed of amphiphilic block copolymers have attracted considerable interests as an effective drug carrier. Additionally, numerous attempts have been made to increase the effectiveness of anticancer drugs by increasing their concentration at the target site. In one embodiment, biodegradable and biocompatible polymers, γ-PGA and PLA, are used to synthesize γ-PGA-PLA block copolymers via a simple coupling reaction between γ-PGA and PLA to prepare self-assembled nanoparticles. In addition, galactosamine is conjugated on the prepared nanoparticles as a targeting moiety.

γ-PGA is a naturally occurring anionic homo-polyamide that is made of L-glutamic acid units connected by amide linkages between α-amino and γ-carboxylic acid groups (Crit. Rev. Biotechnol. 2001; 21:219-232). It is an exocellular polymer of certain *Bacillus* species that is produced within cells via the TCA cycle and is freely excreted into the fermentation broth. Its exact biological role is not fully understood, although it is likely that γ-PGA is linked to increasing the survival of producing strains when exposed to environmental stresses. Because of its water-solubility, biodegradability, edibility, and non-toxicity toward humans and the environment, several applications of γ-PGA in food, cosmetics, medicine, and water treatment have been investigated in the past few years.

EXAMPLE NO. 1

Materials

Paclitaxel powder (purity >99%) and clinical commercial paclitaxel [Phyxol®, contained 6 mg paclitaxel, 527 mg Cremaphor EL and 47.7% (v/v) alcohol per milliliter] were obtained from Sinphar Pharmaceutical Co., Ltd. (Taipei, Taiwan). PLA [poly(L-lactide), Mn: 10 kDa, with a polydispersity index of 1.1 determined by the GPC analysis] was supplied by the Biomedical Engineering Center, Industrial Technology Research Institute (Hsinchu, Taiwan). Dimethyl sulfoxide (DMSO <0.01% water), N,N'-carbonyldiimidazole (CDI, 98%), and dichloromethane were acquired from Fluka (Buchs, Switzerland). L-glutamic acid (purity >99%), N-(3-dimethylaminopropyl)-N'-ethylcarbodiimide (EDC), N-hydroxysuccinimide (NHS), galactosamine, and sodium cholate were purchased from Sigma (St. Louis, Mo.). 4-Dimethylaminopyridine (DMAP) and 1,4-dioxane were obtained from ACROS (Janssen Pharmaceuticalaan, Belgium). All other chemicals used in preparing nanoparticles are reagent grade.

EXAMPLE NO. 2

Production and Purification of γ-PGA

γ-PGA (FIG. 1) was produced by *Bacillus licheniformis* (ATCC 9945, Bioresources Collection and Research Center, Hsinchu, Taiwan) as per the method reported by Yoon et al. with slight modifications (Biotechnol. Lett. 2000; 22:585-588). Highly mucoid colonies (ATCC 9945a) were selected from *Bacillus licheniformis* (ATCC 9945) cultured on the E medium (L-glutamic acid, 20.0 g/l; citric acid, 12.0 g/l; glycerol, 80.0 g/l; $NH_4Cl$, 7.0 g/l; $K_2HPO_4$, 0.5 g/l; $MgSO_4.7H_2O$, 0.5 g/l; $FeCl_3.6H_2O$, 0.04 g/l; $CaCl_2.2H_2O$, 0.15 g/l; $MnSO_4.H_2O$, 0.104 g/l, pH 6.5) agar plates at 37° C. for several times. Subsequently, young mucoid colonies were transferred into 10 ml E medium and grown at 37° C. in a shaking incubator at 250 rpm for 24 hours. Afterward, 500 μl of culture broth was mixed with 50 ml E medium and was transferred into a 2.5-1 jar-fermentor (KMJ-2B, Mituwa Co., Osaka, Japan) containing 950 ml of E medium. Cells were cultured at 37° C. The pH was controlled at 6.5 by automatic feeding of 25% (v/v) $NH_4OH$ and 2M HCl. The dissolved oxygen concentration (DOC) was initially controlled at 40% of air saturation by supplying air and by controlling the agitation speed up to 1,000 rpm.

After 40 hours, cells were separated from the culture broth by centrifugation for 20 minutes at 12,000×g at 4° C. The supernatant containing γ-PGA was poured into 4 volumes of methanol and left overnight with gentle stirring. The resulting precipitate containing crude γ-PGA was collected by centrifugation for 40 minutes at 12,000×g at 4° C. and then was dissolved in distilled water to remove insoluble impurities by centrifugation for 20 minutes at 24,000×g at 4° C. The aqueous γ-PGA solution was desalted by dialysis (MWCO: 12,000-14,000, Spectrum Laboratories, Inc., Laguna Hills, Calif.) against distilled water for 12 hours with water exchanges several times, and finally was lyophilized to obtain pure γ-PGA.

The purified γ-PGA was confirmed by the proton nuclear magnetic resonance ($^1$H-NMR) and the Fourier transformed infrared (FT-IR) analyses. Analysis of $^1$H-NMR was conducted on an NMR spectrometer (Varian Unityionva 500 NMR Spectrometer, MO) using DMSO-$d_6$ at 2.49 ppm as an internal reference. Test samples used for the FT-IR analysis first were dried and ground into a powder form. The powder then was mixed with KBr (1:100) and pressed into a disk. Analysis was performed on an FT-IR spectrometer (Perkin Elmer Spectrum RX1 FT-IR System, Buckinghamshire, England). The samples were scanned in the range of 400-4000 $cm^{-1}$.

In the $^1$H-NMR spectrum of the purified γ-PGA obtained from fermentation, five chief signals observed at 1.73, 1.94, 2.19, 4.14, and 8.15 ppm representing the protons of β-$CH_2$, γ-$CH_2$, α-CH, and amide, respectively. Additionally, the fermented product after purification showed no detected macromolecular impurities by the $^1$H-NMR analysis, suggesting that the obtained white power of γ-PGA was highly pure.

EXAMPLE NO. 3

Hydrolysis of γ-PGA

The average molecular weight (Mn) of the purified γ-PGA obtained via the previous fermentation procedure was about 320 kDa. The purified γ-PGA was then hydrolyzed in a tightly sealed steel container at 150° C. for distinct durations. The average molecular weight along with the polydispersity index of the hydrolyzed γ-PGA were determined by a gel permeation chromatography (GPC) system equipped with a series of PL aquagel-OH columns (one Guard 8 μm, 50×7.5 mm and two MIXED 8 μm, 300×7.5 mm, PL Laboratories, UK) and a refractive index (RI) detector (RI2000-F, SFD, Torrance, Calif.). Polyethylene glycol (molecular weights of 106-22,000 g/mol) and polyethylene oxide (molecular weights of 20,000-1,000,000 g/mol) standards of narrow polydispersity index (PL Laboratories, UK) were used to construct a calibration curve. The mobile phase contained 0.01M $NaH_2PO_4$ and 0.2M $NaNO_3$ and was brought to a pH of 7.0. The flow rate of mobile phase was 1.0 ml/min, and the columns and the RI detector cell were maintained at 30° C.

Figure 2:
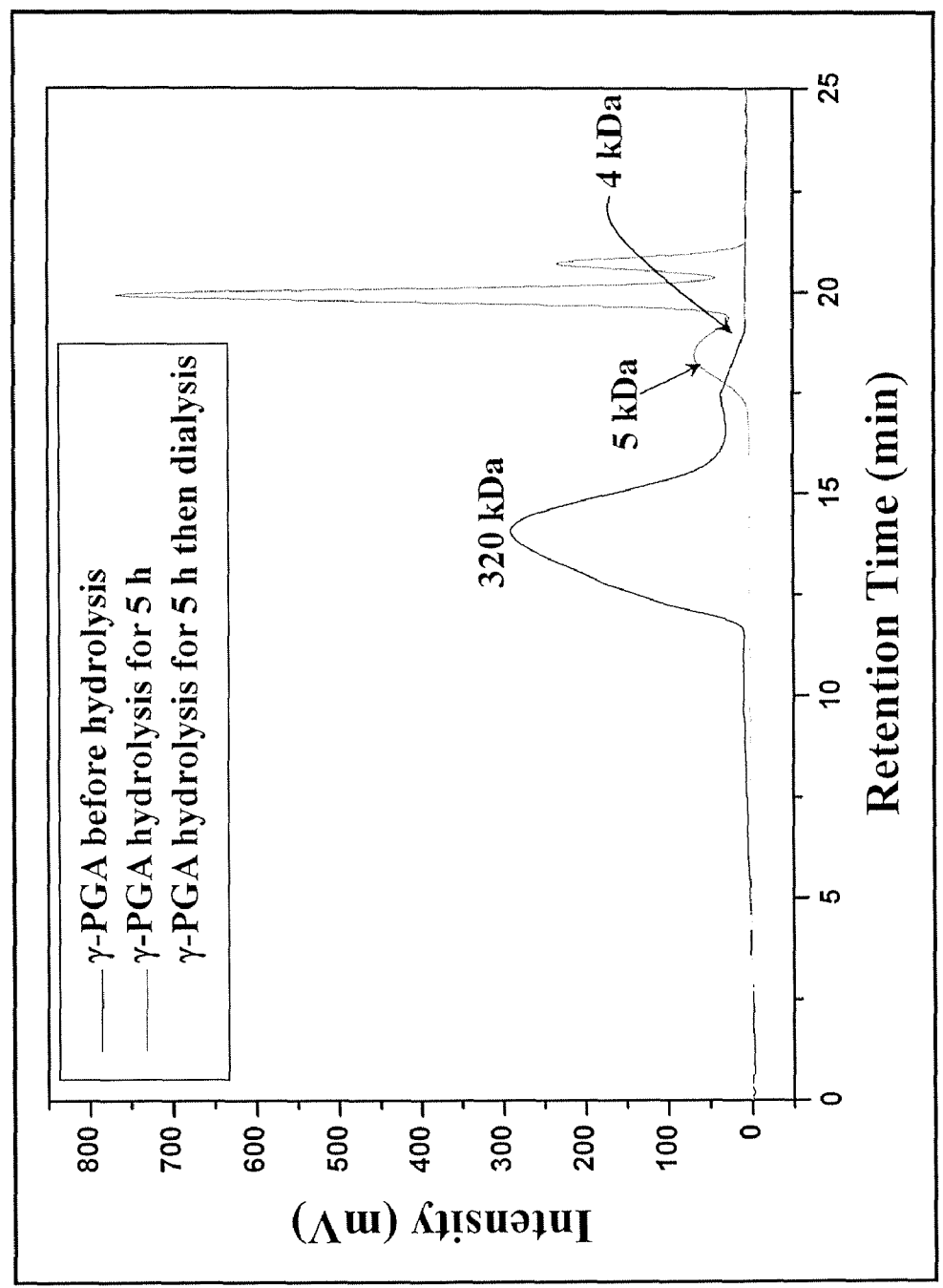
FIG. 2 shows chromatograms of the purified γ-PGA obtained from fermentation (γ-PGA before hydrolysis), the obtained γ-PGA after a 5-h hydrolysis at 150° C. (γ-PGA hydrolysis for 5 h), and the hydrolyzed γ-PGA after dialysis twice against deionized water (γ-PGA hydrolysis for 5 h then dialysis).

Low-molecular-weight γ-PGA was produced by hydrolyzing the purified γ-PGA obtained from fermentation at 150° C. for distinct durations. Solutions of the purified γ-PGA obtained from fermentation and the hydrolyzed γ-PGA were analyzed by a GPC system. As shown in FIG. 2, the purified γ-PGA obtained from fermentation had a high average molecular weight (Mn ~320 kDa) with a polydispersity index of about 1.8. When γ-PGA was hydrolyzed at 150° for 5 hours, the average molecular weight of γ-PGA was reduced to about 5 kDa. To reduce the polydispersity index of the hydrolyzed γ-PGA, the hydrolyzed γ-PGA (~5 kDa) was further dialyzed twice (using a membrane with MWCO: 3,500 and a membrane with MWCO: 6,000-8,000) against deionized water. Thus obtained γ-PGA had an average molecular weight of about 4 kDa with a polydispersity index of 1.3 (FIG. 2). This specific γ-PGA was used subsequently, together with PLA, to synthesize block copolymers to prepare the nanoparticles.

EXAMPLE NO. 4

Synthesis of γ-PGA-PLA Block Copolymers

Block copolymers composed of γ-PGA and PLA were synthesized using CDI to activate the terminal hydroxyl group of PLA. CDI (82 mg) was dissolved in 1,4-dioxane (20 ml) in a nitrogen atmosphere and PLA (0.1 g) was subsequently added into the solution. The clear solution was stirred at 37° C. for 2 hours. Afterward, the solution was dialyzed extensively against deionized water at 4° C. Finally, the activated PLA was obtained via centrifugation.

The acidified form of the hydrolyzed γ-PGA (10 mg, Mn ~4 kDa, PDI=1.3) was dissolved in DMSO (5 ml) in a dry, stoppered 20 ml round bottom flask in a nitrogen atmosphere. After dissolution of DMAP (3 mg), a calculated amount of activated PLA (25 mg) was added. The solution was stirred at room temperature for 3 days, after which the reaction was stopped by adding 0.1 ml of concentrated HCl to neutralize DMAP and imidazole. The reaction mixture was transferred to a dialysis tube and dialyzed for 2 days against deionized water at 4° C. Finally, the product (γ-PGA-PLA block copolymers) was lyophilized and stored at −20° C. until used. The molecular weight distribution of the synthesized block copolymers was determined using a GPC system equipped with a Jordi Gel DVB Mixed Bed column (250×10 mm, Jordi Associates, Inc., MA) and a RI detector. Tetrahydrofuran (THF) was used as an elution solvent (1 ml/min) and polystyrene standards for column calibration.

Low-molecular-weight γ-PGA was produced by hydrolyzing the purified γ-PGA obtained from fermentation at 150° C. for distinct durations. Solutions of the purified γ-PGA obtained from fermentation and the hydrolyzed γ-PGA were analyzed by a GPC system. As shown in FIG. 2, the purified γ-PGA obtained from fermentation had a high average molecular weight (Mn ~320 kDa) with a polydispersity index of about 1.8. When γ-PGA was hydrolyzed at 150° C. for 5 hours, the average molecular weight of γ-PGA was reduced to about 5 kDa. To reduce the polydispersity index of the hydrolyzed γ-PGA, the hydrolyzed γ-PGA (~5 kDa) was further dialyzed twice (using a membrane with MWCO: 3,500 and a membrane with MWCO: 6,000-8,000) against deionized water. Thus obtained γ-PGA had an average molecular weight of about 4 kDa with a polydispersity index of 1.3 (FIG. 2). This specific γ-PGA was used subsequently, together with PLA, to synthesize block copolymers to prepare the nanoparticles.

EXAMPLE NO. 5

Preparation of the Paclitaxel-Loaded Nanoparticles

The paclitaxel-loaded nanoparticles were produced using an emulsion/solvent evaporation technique. Briefly, 10 mg of block copolymers were dissolved in 1 ml methylene chloride, and paclitaxel was subsequently added with varying feed weight ratios to block copolymer [paclitaxel/copolymer (P/C)=0.5/10, 1/10, 2/10, and 3/10]. The solution was then stirred for 2 hours at room temperature and was emulsified in 50 ml of a 0.1 wt % sodium cholate solution using a sonicator (VCX-750, Sonics & Materials Inc., Newtown, Conn., cycles of 1 second sonication followed by 1 second of pauses, total time 20 minutes). Afterward, the solvent was evaporated in a vacuum oven at 37° C. for 1 hour. The resulting suspension was filtered through a 0.8-μm membrane filter (Whatman) and then centrifuged for 60 min at 18,000 rpm at 4° C. The supernatant was subsequently discarded and the pellet was resuspended by 10 ml phosphate buffered saline (PBS, pH 7.4, Sigma). The size distribution and zeta potential of the prepared nanoparticles were measured using a Zetasizer (3000HS, Malvern Instruments Ltd., Worcestershire, UK).

TEM and AFM were used to observe the morphology of the paclitaxel-loaded nanoparticles. The TEM sample was prepared by placing a drop of the paclitaxel-loaded nanoparticle solution onto a 400 mesh copper grid coated with carbon. About 2 minutes after deposition, the grid was tapped with a filter paper to remove surface water and negatively stained by using a 2% (by w/v) phosphortungsten acid (PTA) solution. The AFM sample was prepared by casting a drop of the paclitaxel-loaded nanoparticle solution on a slide glass and then dried in vacuum.

Figure 3:
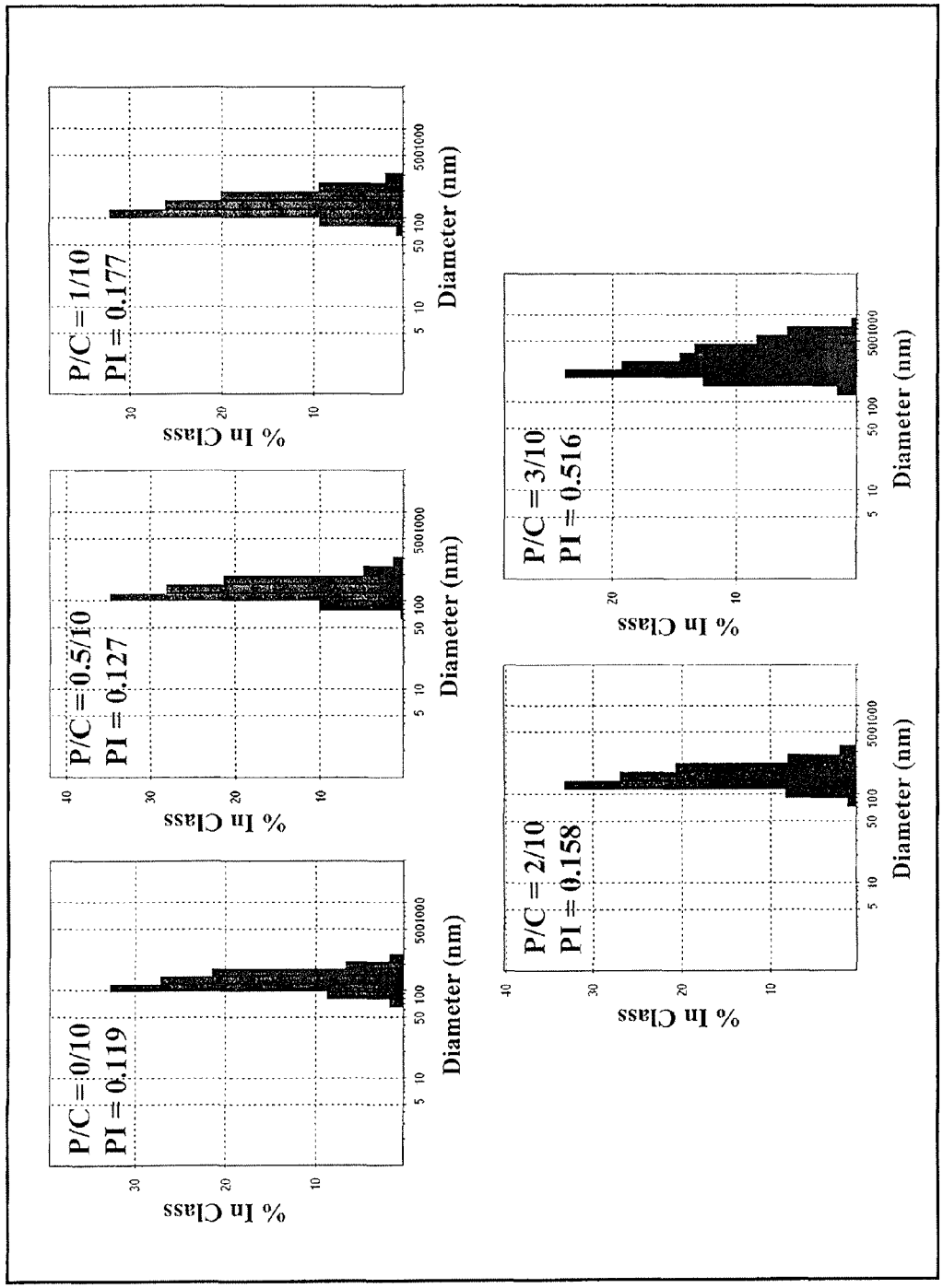
FIG. 3 shows size distributions of the nanoparticles prepared with varying feed weight ratios of paclitaxel to block copolymer (the P/C ratio). PI: the polydispersity index of the size distribution of the prepared nanoparticles.

The size distribution and zeta potential of the prepared nanoparticles play important roles in determining their fates after administration. As shown in Table 1, the particle size of the prepared nanoparticles increases significantly with increasing the P/C ratio. Dynamic light scattering measurements further demonstrated that all the prepared nanoparticles have a narrow size distribution, with the exception of those prepared with a P/C ratio of 3/10 (FIG. 3). The AFM and TEM examinations showed that the morphology of all the prepared nanoparticles is spherical in shape with a smooth surface (FIG. 4).

TABLE 1

Particle size, zeta potential, and drug loading content (LC) and loading efficiency (LE) of the nanoparticles prepared with varying feed weight ratios of paclitaxel to block copolymer (the P/C ratio).

| P/C Ratio (n = 4) | Particle Size (nm) | Zeta Potential (mV) | LC (%) | LE (%) |
|---|---|---|---|---|
| 0/10 | 115.4 ± 4.2 | −21.4 ± 2.3 | — | — |
| 0.5/10 | 125.9 ± 5.5 | −77.5 ± 3.7 | 3.7 ± 0.1 | 76.5 ± 2.4 |
| 1/10 | 128.8 ± 3.4 | −19.6 ± 1.8 | 5.1 ± 0.2 | 53.7 ± 1.7 |
| 2/10 | 144.4 ± 2.6 | −20.3 ± 2.7 | 5.8 ± 0.2 | 30.8 ± 2.3 |
| 3/10 | 263.2 ± 6.8 | −19.2 ± 2.2 | 6.1 ± 0.2 | 21.7 ± 4.2 |

Hashida et al. reported that the majority of the fenestrate of the liver sinusoid is usually smaller than 200 nm in diameter. Thus, large particles hardly reach the liver's parenchymal cells. Additionally, drug carriers with a diameter larger than 200 nm are readily scavenged non-specifically by monocytes and the reticuloendothelial system. It was reported that smaller particles tended to accumulate at the tumor sites due to the EPR (enhanced permeability and retention) effect and a greater internalization was also observed.

As shown in Table 2, the particle size of the Gal-NPs was comparable to that of the NPs (p>0.05). However, the zeta potential of the former was significantly lower than that of the latter (p<0.05). This is because galactosamine was conjugated to the carboxyl (—COO⁻) groups on γ-PGA (the hydrophilic shell of the nanoparticles) and thus reduced the negative surface charge of the Gal-NPs. The drug loading content and loading efficiency of the Gal-NPs were relatively lower than those of the NPs (p<0.05).

TABLE 2

Particle size, zeta potential, and drug loading content (LC) and loading efficiency (LE) of the paclitaxel-loaded nanoparticles without (NPs) or with (Gal-NPs) galactosamine conjugated.

| Samples (n = 4) | Particle Size (nm) | Zeta Potential (mV) | LC (%) | LE (%) |
|---|---|---|---|---|
| NPs | 128.8 ± 3.4 | −19.6 ± 1.8 | 5.1 ± 0.2 | 53.7 ± 1.6 |
| Gal-NPs | 127.5 ± 2.5 | −10.6 ± 2.0 | 4.8 ± 0.2 | 50.2 ± 2.1 |

It was found that the prepared paclitaxel-loaded nanoparticles have a negative surface charge with a zeta potential of about −20 mV (Table 1), due to the carboxyl (—COO⁻) groups on the hydrophilic γ-PGA shell. This may affect the cellular uptake of the prepared nanoparticles due to electrostatic repulsion forces between the nanoparticles and the rather negatively charged surface of cells. However, Wakebayashi et al. suggested that introduction of a specific ligand on the nanoparticles may enhance their cellular uptake via a receptor-mediated endocytosis. Additionally, it was reported that positively charged carriers might induce a non-specific interaction with unintended target tissues, particularly under in vivo conditions after administration.

EXAMPLE NO. 6

Loading Content and Efficiency of the Paclitaxel-Loaded Nanoparticles

The drug loading content and loading efficiency of the nanoparticles were determined using a high-performance liquid chromatography (HPLC) system equipped with a $C_{18}$ analytic column (4.6×250 mm, particle size 5 µm, Thermo-Quest, BDS, Runcorn, UK). Two milligrams of the freeze-dried paclitaxel-loaded nanoparticles were dissolved in 1 ml dichloromethane under vigorous vortexing. This solution was dried by evaporating dichloromethane in vacuum and then was dissolved in a mixture of 50/50 (v/v) ethanol and deionized water for the HPLC analysis. The flow rate of the mobile phase (60% acetonitrile and 40% deionized water by v/v), delivered by an HPLC pump (TCP, P-100, Riviera Beach, Fla.), was 1 ml/min at 30° C. The injection volume was 40 µl and paclitaxel eluted from the column was monitored with an UV detector (Jasco 875-UV, Tokyo, Japan) at 227 nm. The drug loading content and loading efficiency of the nanoparticles were calculated using the equations listed below, respectively.

$$\text{Loading Content (\%)} = \frac{\text{weight of paclitaxel in the nanoparticles}}{\text{weight of the nanoparticles}} \times 100\%$$

$$\text{Loading Efficiency (\%)} = \frac{\text{weight of paclitaxel in the nanoparticles}}{\text{weight of the feeding paclitaxel}} \times 100\%$$

Paclitaxel is highly hydrophobic with a solubility of approximately 1 µg/ml in aqueous solution at pH 7.4. Thus, in the drug loading process, incorporation of paclitaxel in the nanoparticles and precipitation of paclitaxel in aqueous solution competed with each other. With increasing the P/C ratio, incorporation of paclitaxel in the nanoparticles (the drug loading content) appears to increase, while precipitation of paclitaxel in aqueous solution is more pronounced and consequently results in a significantly lower drug loading efficiency (Table 1, $p<0.05$).

EXAMPLE NO. 7

Release of Paclitaxel from the Loaded Nanoparticles

The release profiles of paclitaxel from the prepared nanoparticles were investigated in PBS at 37° C. The freeze-dried paclitaxel-loaded nanoparticles were weighed and resuspended in a centrifuge tube containing 20 ml PBS. The tube was placed in a shaker water bath at 37° C. At particular time intervals, the tube was taken out and centrifuged. The supernatant was poured out, freeze-dried, and then dissolved in a mixture of 50/50 (v/v) ethanol and deionized water for the HPLC analysis. The pellet was resuspended in 20 ml fresh PBS for continuous release measurements. The paclitaxel released at each time point was calculated using a calibration curve.

Paclitaxel was continuously released from the nanoparticles prepared with distinct P/C ratios. All samples exhibited a burst release of paclitaxel at the initial stage. About 10-25% of the encapsulated drug was released in the first hour. This may be due to some portion of drugs were deposited at the region near the γ-PGA shell of the prepared nanoparticles.

With increasing the P/C ratio, the release rate of paclitaxel from the prepared nanoparticles decreases significantly. It was reported that a hydrophobic drug encapsulated within the nanoparticles partially crystallizes at a higher drug loading content, while it forms a molecular dispersion at a lower drug loading content. The crystallized drug in the hydrophobic core of the nanoparticles is expected to dissolve more gradually and diffuse to their outer aqueous phase more slowly than that in the form of a molecular dispersion. Additionally, it would take a longer time for the encapsulated drug to diffuse across the polymer matrix to the aqueous medium for a larger size of nanoparticles (i.e., with increasing the P/C ratio, see Table 1).

Figure 5:
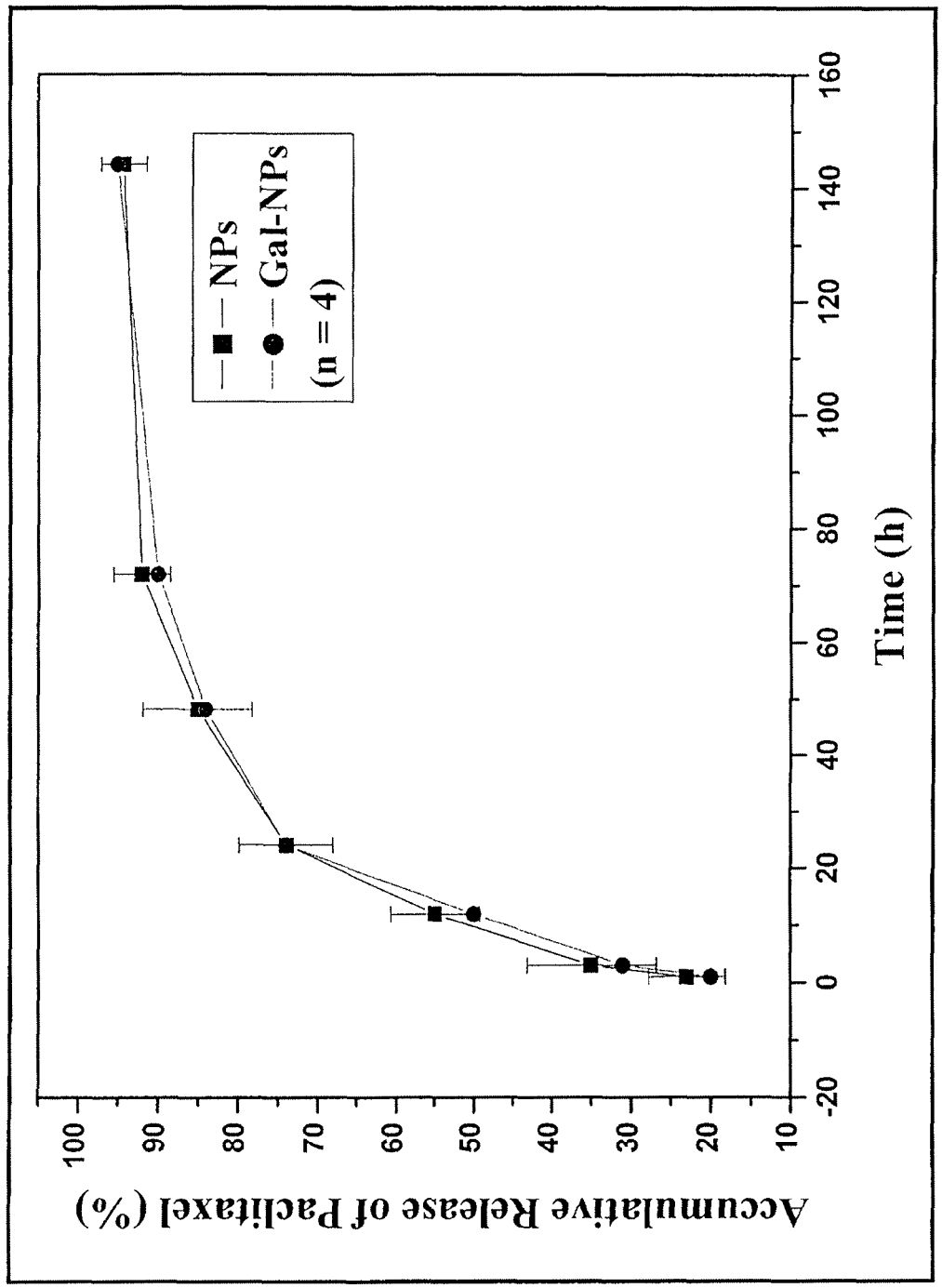
FIG. 5 shows release profiles of paclitaxel from the nanoparticles without (NPs) or with (Gal-NPs) galactosamine conjugated.

As shown in FIG. 5, both the NPs and the Gal-NPs have a similar release profile of paclitaxel ($p>0.05$) and exhibit a burst release of paclitaxel at the initial stage. About 20% of the encapsulated drug in the NPs or the Gal-NPs was released in the first hour. This may be due to some portion of drugs were deposited at the region near the γ-PGA shell of the prepared nanoparticles.

EXAMPLE NO. 8

Conjugation of Galactosamine to the Paclitaxel-Loaded Nanoparticles

Galactosamine was conjugated to the paclitaxel-loaded nanoparticles via an amide linkage by EDC in the presence of NHS. The conditions found in our co-pending application U.S. Ser. No. 10/958,864 filed Oct. 5, 2004, to conjugate galactosamine on the nanoparticles that had the greatest amount of nanoparticles internalized in HepG2 cells were used in the present study. The obtained galactosylated nanoparticles were separated from unreacted molecules via ultrafiltration and then lyophilized. The content of galactosamine conjugated on the nanoparticles was determined by the Morgan Elson assay.

As discussed earlier, with increasing the P/C ratio, the drug loading content of the prepared nanoparticles increases significantly, while their drug loading efficiency decreases remarkably (Table 1). To obtain a comparatively high drug loading content simultaneously with a high loading efficiency (Table 1), the nanoparticles prepared with a P/C ratio of 1/10 (the NPs) were used for the rest of the study. For the potential of targeting liver cancer cells, galactosamine was conjugated to the paclitaxel-loaded nanoparticles (the Gal-NPs). As determined by the Morgan Elson assay, the amount of galactosamine conjugated on the Gal-NPs was 66.2±2.4 nmole/mg nanoparticles (n=4). The particle size of the Gal-NPs (127.5±2.5 nm) was comparable to that of the NPs (128.8±3.4 nm, $p>0.05$). However, the zeta potential of the former (−10.6±2.0 mV) was significantly lower than that of the latter (−19.6±1.8 mV, $p<0.05$). This is because galactosamine was conjugated to the carboxyl (—COO$^-$) groups on γ-PGA and thus reduced the negative surface charge of the Gal-NPs.

EXAMPLE NO. 9

Viability of HepG2 Cells Treated with Distinct Paclitaxel Formulations

The cytotoxicity of the paclitaxel-loaded nanoparticles with or without galactosamine conjugated was evaluated in vitro by the MTT assay, using a clinically available paclitaxel formulation (Phyxol®. Sinphar Pharmaceutical) as a control. The assay is based on mitochondrial dehydrogenase cell activity as an indicator of cell viability. Briefly, MTT [3-(4, 5-dimethyl-thiazol-yl)-2,5-diphenyltetrazolium bromide, Sigma] was dissolved in PBS with a concentration of 5 mg/ml as a stock MTT solution and filtered for sterilization. HepG2 cells were seeded in 24-well plates at $5\times10^4$ cells/well and were allowed to adhere overnight. The growth medium was replaced with a fresh one containing varying concentrations (0.25-8 μg/ml) of distinct paclitaxel formulations investigated in the study: Phyxol®, the nanoparticles without galactosamine conjugated (the NPs), and the nanoparticles with galactosamine conjugated (the Gal-NPs).

The cells were then incubated for 3 days and washed twice by 1 ml PBS. Subsequently, the cells were incubated in a growth medium containing 1 mg/ml MTT agent for an additional 4 hours at 37° C. and 500 μl of DMSO was added to each well to ensure solubilization of formazan crystals. Finally, the optical density readings were performed using a multiwell scanning spectrophotometer (MRX Microplate Reader, Dynatech Laboratories Inc., Chantilly, Va.) at a wavelength of 570 nm.

Hepatoma cells are known to recognize galactose- and N-acetylgalactosamine-terminated glycoproteins via the asialoglycoprotein (ASGP) receptors located on their surfaces. It was found in our previous study that in the incubation with the rhodamine-123-containing nanoparticles without galactosamine conjugated, little fluorescence was observed in HepG2 cells on the images taken by the CLSM. This indicated that without galactosamine, only a small amount of the nanoparticles were able to be internalized in cells, due to electrostatic repulsion forces between the nanoparticles and the cells as mentioned earlier. Hence, the NPs prepared in the study released paclitaxel mainly outside of the cells (i.e., in the culture medium). The released paclitaxel was then diffused into HepG2 cells and led to inhibit the growth of the cells. Accordingly, under in vivo conditions after administration, the normal tissues may be non-selectively exposed to paclitaxel released from the NPs in the blood stream, which can lead to unwanted toxic side effects.

In contrast, with increasing the galactosamine content conjugated on the rhodamine-123-containing nanoparticles, the intensity of fluorescence observed in HepG2 cells increases significantly at 30 min after incubation. This indicates that the galactosylated nanoparticles had a specific interaction with HepG2 cells via ligand-receptor (ASGP) recognition. Therefore, the Gal-NPs prepared in the study were first internalized into HepG2 cells via the ASGP receptors, and then released the encapsulated paclitaxel inside cytoplasm to inhibit the growth of the cells. Thus, the active targeting nature of the Gal-NPs may lead to a high degree of selectivity to the hepatic tumor and enhance their cellular uptake, with a consequent decrease in systemic toxicity.

Figure 6:
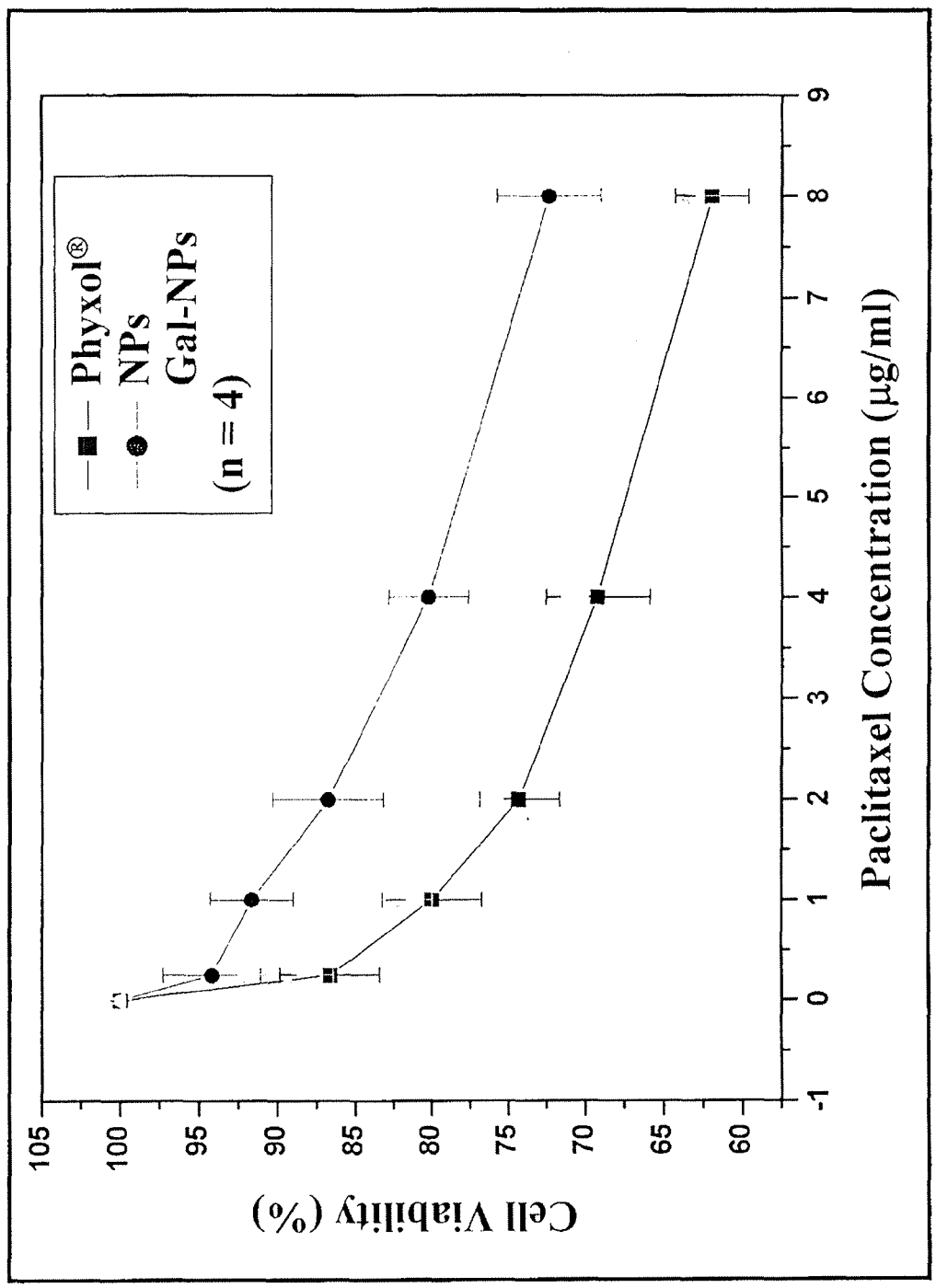
FIG. 6 shows viability of HepG2 cells treated with distinct paclitaxel formulations with varying paclitaxel concentrations. Phyxol®: cells treated with a clinically available paclitaxel formulation (Sinphar Pharmaceutical); NPs: cells treated with the paclitaxel-loaded nanoparticles without galactosamine conjugated; and Gal-NPs: cells treated with the paclitaxel-loaded nanoparticles with galactosamine conjugated.

FIG. 6 shows the viability of HepG2 cells treated with distinct paclitaxel formulations investigated in the study. As shown, the activity in inhibiting the growth of cells by the Gal-NPs was comparable to that of a clinically available paclitaxel formulation (Phyxol®, $p>0.05$), while the NPs displayed a significantly less activity ($p<0.05$).

EXAMPLE NO. 10

Immunofluorescence Analysis of HepG2 Cells

HepG2 cells were grown on glass coverslips and then treated with distinct paclitaxel formulations with a final paclitaxel concentration of 8 μg/ml. After incubation for 3 days, the cells were fixed with 3.7% formaldehyde in PBS for 10 min at room temperature and then permeabilized in 0.1% Triton X-100 in PBS containing 1% bovine serum albumin (PBS-BSA) and RNase 100 μg/ml. After washing 3 times with PBS-BSA, the cells were treated with Oregon Green® 514 palloidin (1:100 v/v, Molecular Probes) in PBS-BSA for 20 min. Cells were then incubated for 60 min with anti-bovine α-tubulin mouse mAb (1 μg/ml, Molecular Probes) in PBS-BSA. The Alexa Fluor® 633-conjugated goat anti-mouse IgG antibody (2 μg/ml, Molecular Probes) was added and incubated for another 60 min. Subsequently, cells were rinsed 3 times with PBS-BSA and treated with 100 nM propidium iodide (PI, Sigma) for 5 min.

Before mounting the samples for the CLSM examinations, cells were washed again with PBS and deionized water. Oregon Green® 514 palloidin, PI, or Alexa Fluor® 633 staining were visualized with excitations at 488, 543, and 633 nm, respectively, using an inversed CLSM (TCS SL, Leica, Germany). Superimposed images were performed with an LCS Lite software (version 2.0).

EXAMPLE NO. 11

Altered Cycling States of HepG2 Cells Treated with Distinct Paclitaxel Formulations To demonstrate whether paclitaxel released from the prepared NPs or the Gal-NPs could restrict HepG2 cells in specific cell cycle stages, flow cytrometric studies were performed. HepG2 cells treated with distinct paclitaxel formulations with a final paclitaxel concentration of 1 μg/ml for 3 days were pelleted at 1500 rpm for 5 min and then were resuspended in PBS. The cell suspension was then added with 100% methanol precooled to −20° C. for 15 min and centrifuged at 1500 rpm for 5 min. The supernatant was discarded, and the cell pellet was rehydrated with PBS. The pellet was stained with a DNA staining solution (10 μg/ml PI and 1 mg/ml RNase A) for 45 min. The DNA content of each cell was measured using a Becton Dickinson FACSCalibur flow cytometer (San Jose, Calif.).

Some aspects of the invention relate to the paclitaxel-loaded nanoparticles with galactosamine conjugated that are configured to be internalized into HepG2 cells via a receptor-mediated endocytosis, resulting in the inhibition of the growth of cells. Therefore in one embodiment, the prepared nanoparticles are provided as a potential drug delivery system for the targeted delivery to liver cancers.

EXAMPLE NO. 12

Animal Study

Male Balb/c mice (5-7 weeks old, 18-22 g) and Balb/c-nu/nu nude mice (5-7 weeks old, 16-20 g) were obtained from the National Laboratory Animal Center (Taipei, Taiwan) and acclimatized for 7 days after arrival. Nude mice were housed in individually ventilated cages (IVC cages) of isolated ventilation to avoid microbial contamination. Balb/c-nu/nu nude mice were injected subcutaneously in the right flank with 0.1 ml of cell suspension containing $10^6$ human hepatoma cells (HepG2) and allowed to grow to a mean volume of 50 mm$^3$. Animal care and use was performed in compliance with the "Guide for the Care and Use of Laboratory Animals" prepared by the Institute of Laboratory Animal Resources, National Research Council, and published by the National Academy Press, revised 1996.

EXAMPLE NO. 13

Biodistribution of the Prepared Nanoparticles

In the study, rhodamine-123 was used as a model fluorescent probe that can be encapsulated in the hydrophobic core of the prepared nanoparticles. The prepared rhodamine-123-containing nanoparticles in PBS were injected into the tail vein of normal or tumor-bearing mice at a dose of 10 mg/kg.

At different time intervals after injection, mice were sacrificed, blood was drawn, and various tissues such as the brain, liver, spleen, lung, kidney, and tumor were excised. An aqueous solution (10 ml) containing deionized water and ethanol (50/50 by v/v) was added to each tissue, and the mixture was homogenized. The mixtures were subsequently centrifuged at 14,000 rpm for 30 min. The supernatants were then lyophilized and resuspended in 1 ml deionized water. Finally, the fluorescence intensities of the solutions were measured using a spectrofluorometer (F-2500, Hitachi, Tokyo, Japan) at an emission wavelength of 520 nm and an excitation wavelength of 490 nm.

Biodistribution of the prepared nanoparticles in various organs in normal mice and hepatoma-tumor-bearing nude mice were evaluated at distinct durations after the injection of the NPs or the Gal-NPs loaded with rhodamine 123. For normal mice, the NPs were distributed mainly in the spleen (FIG. 7a) due to the splenic filtration, whereas the amount of the Gal-NPs observed in the spleen decreased significantly ($p<0.05$, FIG. 7b). It was found that the Gal-NPs are mainly accumulated in the liver.

For hepatoma-tumor-bearing nude mice, similar observations were observed in the spleen and the liver for the groups injected with the NPs (FIG. 8a) or the Gal-NPs (FIG. 8b). It should be noted that the amount of nanoparticles observed at the tumor site for the group injected with the Gal-NPs was significantly greater than that injected with the NPs ($p<0.05$).

These observations were further confirmed by our CLSM inspection of the spleen, liver, and tumor sections retrieved from the mice injected with the NPs or the Gal-NPs loaded with rhodamine 123. For the group injected with the NPs, the intensity of fluorescence observed in the spleen was much stronger than in the liver and the tumor site. In contrast, for the group injected with the Gal-NPs, the intensities of fluorescence observed in the liver and the tumor site increased significantly. The aforementioned results indicated that the galactosylated nanoparticles prepared in the study had a specific interaction with liver's parenchymal cells and HepG2 tumor cells via ligand-receptor recognition.

EXAMPLE NO. 14

Antitumor Efficacy of the Prepared Nanoparticles

The antitumor efficacy of distinct paclitaxel formulations against the subcutaneously implanted solid tumors induced by HepG2 cells in nude mice was evaluated. Treatments were started when the tumors in nude mice reached a tumor volume of 50 mm$^3$ and this day was designated day 0. Mice were divided into four different groups [treated with PBS (control), Phyxol®, the NPs, or the Gal-NPs], consisting of four mice in each group. Distinct paclitaxel formulations were then injected via tail vein administration at a single dose of 20 mg paclitaxel/kg in PBS on days 0, 4, 8, 12, 16. The size of the tumor and the change of body weight of each mouse were recorded.

Figure 9:
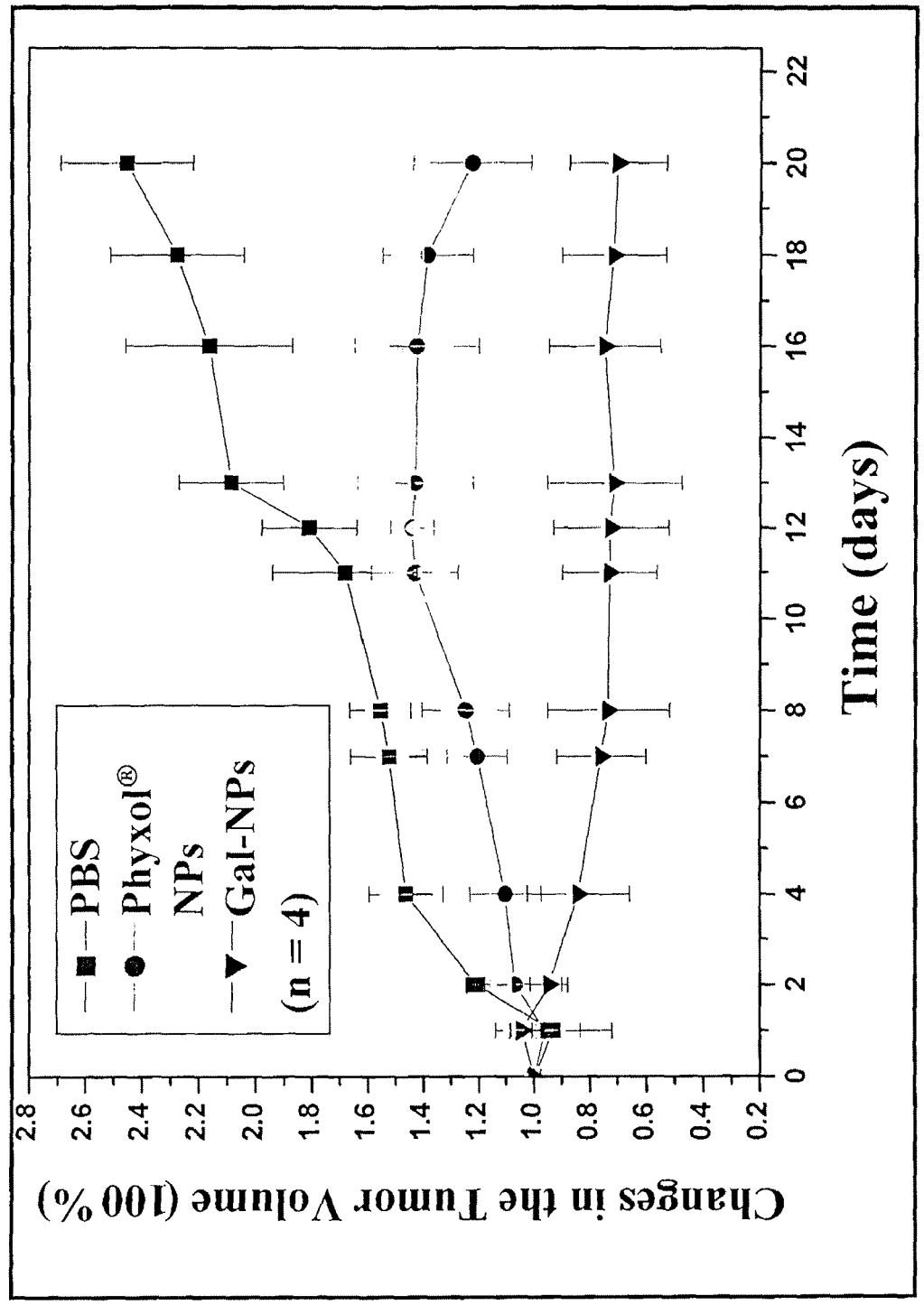
FIG. 9 shows changes in the tumor volume of the hepatoma-tumor-bearing nude mice injected with distinct paclitaxel formulations. PBS: mice injected with PBS; Phyxol®: mice injected with a clinically available paclitaxel formulation (Sinphar Pharmaceutical); NPs: mice injected with the paclitaxel-loaded nanoparticles without galactosamine conjugated; and Gal-NPs: mice injected with the paclitaxel-loaded nanoparticles with galactosamine conjugated.

The antitumor efficacy of the NPs and the Gal-NPs was studied in hepatoma-tumor-bearing nude mice. FIG. 9 shows the progress of the tumor growth observed for 20 days in nude mice injected with PBS (control) or distinct paclitaxel formulations. It was found that the size of the tumor for the control group increases significantly with time, indicating that PBS has no significant effect in preventing the tumor growth. In contrast, the groups injected with Phyxol®, the NPs or the Gal-NPs significantly delayed the tumor growth as compared to the control group ($p<0.05$). Among all study groups, the group injected with the Gal-NPs appears to have the most significant efficacy in the reduction of the size of the tumor ($p<0.05$). This is because a large number of the Gal-NPs actively targets at the tumor site as mentioned earlier (FIG. 8b), and subsequently release their encapsulated paclitaxel to inhibit the growth of the tumor.

Some weight loss was observed with time for all study groups, with the exception of the group injected with the Gal-NPs ($p>0.05$). The observation of weight loss was particularly remarkable for the group injected with Phyxol® ($p<0.05$). These observations implied that for the group injected with Phyxol® (a free form of paclitaxel), paclitaxel is delivered not only to the tumor cells but also to other normal cells in nude mice, whereas the Gal-NPs are mainly accumulated at the tumor site and the liver.

Plasmid DNA

Plasmids (pEGFP-N2, 4.7 kb) containing a CMV promoter and an enhanced green fluorescence protein reporter (EGFP reporter) were obtained from BD Biosciences Clontech (Palo Alto, Calif., USA). pEGFP-N2 was amplified and isolated using a Plasmid Mega Kit (QIAGEN, Valencia, Calif., USA). The recovered plasmids were stored at 4° C. in sterile deionized (DI) water. The purity of plasmids was analyzed by gel electrophoresis (0.8% agarose), while their concentration was measured by UV absorption at 260 nm (V-530, Jasco, Tokyo, Japan). One aspect of the invention relates to preparation of the NPs (i.e., CS/γ-PGA/DNA NPs) encapsulated with a plasmid DNA containing a reporter gene. Physicochemical characteristics of the prepared NPs were examined by Fourier transformed infrared (FT-IR) spectroscopy and transmission electron microscopy (TEM) as well as small angle X-ray scattering (SAXS) and dynamic light scattering (DLS) measurements.

Preparation of NPs

The charge ratio (N/C/P) of NPs was expressed as the ratio of moles of the amino groups (N) on CS to the carboxyl groups (C) on γ-PGA and the phosphate groups (P) on DNA or siRNA. Test NPs at various known N/C/P molar ratios (study groups of 8:0:1, 8:1:1, 8:2:1, 8:4:1 and 8:6:1) were prepared by an ionic-gelation method. By ways of illustration, an aqueous DNA (pEGFP-N2, 33 µg) was mixed with an aqueous γ-PGA (20 kDa, Vedan, Taichung, Taiwan) at different concentrations (12.8 µg, 25.6 µg, 51.2 µg or 76.8 µg, final volume 80 µl). NPs were obtained upon addition of the mixed solution, using a pipette, into an aqueous CS (80 kDa, 0.4 µg/µl, 400 µl, pH 6.0, Challenge Bioproducts, Taichung, Taiwan). The solutions were thoroughly mixed for 10-15 seconds and left for at least 1 hour at room temperature. NPs were collected by centrifugation at 14,000 rpm for 30 min. Supernatants were discarded and NPs were resuspended in DI water at pH 6.0 for further studies.

Characteristics of NPs

The pKa values of CS and γ-PGA are 6.5 and 2.9, respectively. In DI water (pH 6.0), CS and γ-PGA are in ionized forms. The ionized CS, γ-PGA and DNA can form polyelectrolyte complexes (CS/γ-PGA/DNA NPs) by ionic interactions between the positively charged amino groups ($—NH_3^+$) on CS and the negatively charged carboxyl groups ($—COO^-$) on γ-PGA and phosphate groups ($—PO_4^-$) on DNA. The particle size, polydispersity index, zeta potential and DNA encapsulation efficiency of NPs prepared at varying N/C/P molar ratios, obtained by DLS, are shown in Table 3. It can be seen that the prepared NPs are in the nanometer scale (150-250 nm) with a positively charged zeta potential. With increasing amount of the negatively charged γ-PGA, the positively charged zeta potential of NPs decreases.

TABLE 3

Particle size (nm), polydispersity index (PI), zeta potential (mV) and encapsulation efficiency (EE, %) of CS/DNA or CS/γ-PGA/DNA nanoparticles prepared at varying N/C/P molar ratios (n = 5). CS: chitosan; γ-PGA: poly-γ-glutamic acid.

| N/C/P Ratio | 8:0:1 | 8:1:1 | 8:2:1 | 8:4:1 | 8:6:1 |
|---|---|---|---|---|---|
| Particle Size | 229.3 ± 29.2 | 174.5 ± 12.1 | 146.0 ± 8.6 | 146.6 ± 10.2 | 173.9 ± 14.7 |
| PI | 0.54 ± 1.81 | 0.43 ± 0.15 | 0.28 ± 0.09 | 0.14 ± 0.03 | 0.17 ± 0.05 |
| Zeta Potential | 36.2 ± 0.5 | 34.3 ± 0.8 | 32.9 ± 1.5 | 20.6 ± 0.8 | 16.4 ± 1.4 |
| EE | 98.4 ± 1.9 | 97.0 ± 2.5 | 96.8 ± 3.1 | 98.1 ± 1.4 | 98.5 ± 1.2 |

The encapsulation efficiencies of DNA in the NPs prepared at distinct N/C/P ratios are about the same and approached 100%, even with the incorporation of the negatively charged γ-PGA. Among all study groups, the NPs prepared at an N/C/P ratio of 8:4:1 have the smallest polydispersity index. Polydispersity index, obtained by the photon correlation spectroscopy analysis, is a parameter defining the particle size distribution of NPs. It is a dimensionless number extrapolated from the autocorrelation function and ranges from a value of 0.01 for monodispersed particles up to a value around 0.5-0.7. A value greater than 0.7 is characteristic of samples with a very broad size distribution. For a better control of DNA delivery or for gene expression, the NPs prepared at an N/C/P ratio of 8:4:1, which display the smallest size distribution among all study groups, were chosen for further studies. However, the NPs at N/C/P ratio range of 8:1:1 to 8:6:1 all show favorably a PI of between about 0.45 and 0.1 and an average particle size of between about 200 nm and 100 nm.

Figure 13:
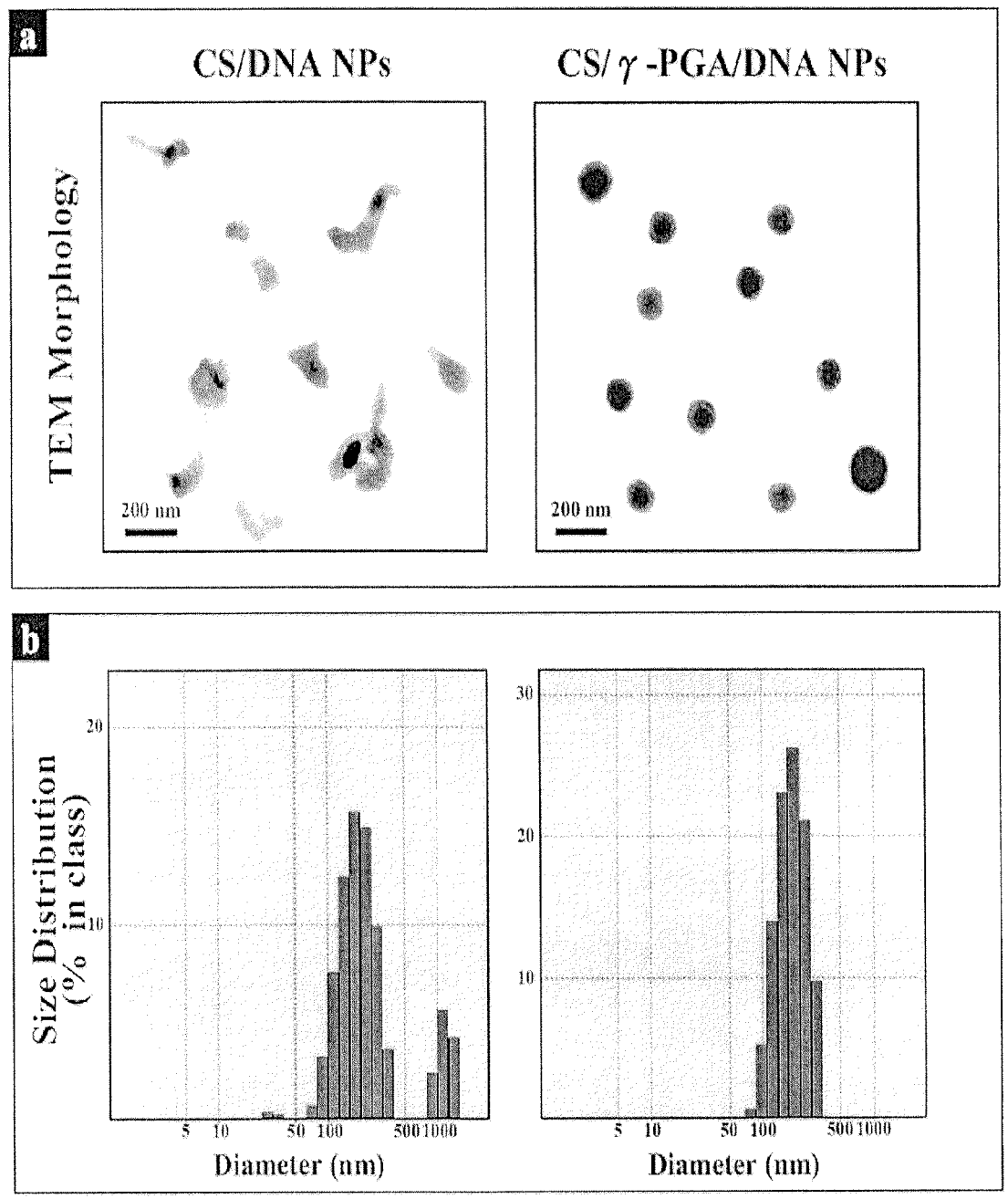
FIG. 13 shows (a) TEM micrographs of CS/DNA and CS/γ-PGA/DNA NPs; (b) size distribution of CS/DNA and CS/γ-PGA/DNA NPs obtained by dynamic light scattering. CS: chitosan; γ-PGA: poly-γ-glutamic acid; NPs: nanoparticles.

In one embodiment, the CS/γ-PGA/DNA NPs (N/C/P ratio of 8:4:1) prepared in DI water (pH 6.0) are spherical in shape with a relatively homogeneous size distribution (FIGS. 13a and 13b). In contrast, CS/DNA NPs (N/C/P ratio of 8:0:1) have a heterogeneous size distribution with a donut, rod or pretzel shape. Similar observation was also reported by other groups on the control CS/DNA NPs. Additionally, the CS/γ-PGA/DNA NPs appear to be more compact than CS/DNA NPs. All other CS/γ-PGA/DNA NPs (N/C/P ratio of 8:1:1 to 8:6:1) are all in spherical or spheroidal shape.

The diameters of NPs observed by TEM (FIG. 13a) (JEOL, Tokyo, Japan) are significantly smaller than those obtained by DLS (Table 3). This is because the diameters of NPs obtained by DLS reflect the hydrodynamic diameters of NPs swollen in aqueous solution, while those observed by TEM are the diameters of dried NPs.

Stability of NPs at Different pH Environments

No aggregation of CS/DNA NPs or CS/γ-PGA/DNA NPs during storage in DI water (pH 6.0) for at least 8 weeks is observed and changes in their particle size and zeta potential are minimal, as a result of the electrostatic repulsion between the positively charged NPs. Precipitation of particles is observed with time (within 2 weeks) for aqueous suspensions of CS/γ-PGA/DNA NPs but not for CS/DNA NPs, indicating that the density of CS/γ-PGA/DNA NPs is greater than that of CS/DNA NPs. However, the precipitated CS/γ-PGA/DNA NPs can be resuspended in DI water after a vigorous vortex.

Figure 14:
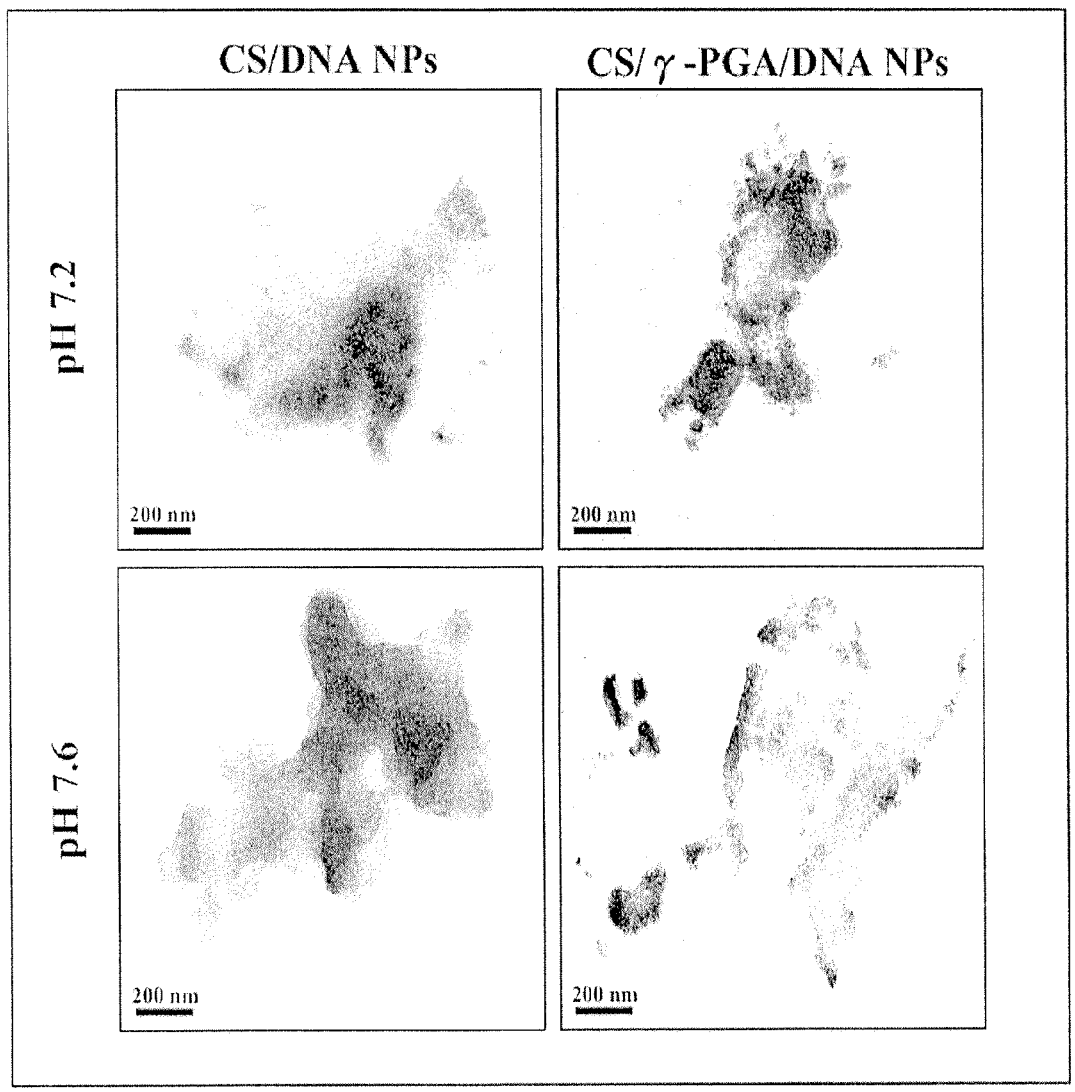
FIG. 14 show TEM micrographs of CS/DNA NPs and CS/γ-PGA/DNA NPs at pH 7.2 and pH 7.6 (simulating the pH environments in the cytoplasm and nuclei of cells, respectively). CS: chitosan; γ-PGA: poly-γ-glutamic acid; NPs: nanoparticles.

At pH 7.2 and pH 7.6 (simulating the pH environments in the cytoplasm and nuclei of cells, respectively), most amino groups on CS are in the form of —$NH_2$. There is little electrostatic interaction between the deprotonated CS and DNA/γ-PGA. CS/DNA NPs and CS/γ-PGA/DNA NPs become unstable and subsequently break apart (FIG. 14). These results indicate that both CS/DNA and CS/γ-PGA/DNA NPs are pH-sensitive.

DNA Protection Against DNase I Treatment

It was reported that the plasmid DNA encapsulated in CS/DNA NPs can be protected from nuclease degradation. The plasmid DNA must remain intact to assure its functionality once inside the cell. It is noted that the encapsulation results in a transformation of DNA from the supercoiled to the open circular form. These results indicate that CS/γ-PGA/DNA NPs are able to effectively retain the encapsulated DNA and protect it from nuclease degradation.

Animal Study with CS/γ-PGA/DNA NPs

A carrier must release its encapsulated DNA at some point in the delivery process. The NPs prepared herein are pH-sensitive. At pH values simulating the environments of cytoplasm and nuclei within the cell, both CS/DNA NPs and CS/γ-PGA/DNA NPs become unstable and break apart in a short time (FIG. 14). Therefore, once into skin cells, both test NPs and control NPs might collapse, subsequently release the encapsulated DNA and facilitate expression of the encoded protein.

The Balb/C mice (female, 10-12 weeks old; n=5) were used in the study of DNA delivery. Mice were anesthetized using pentobarbital prior to experiment. After removing the hair covering the abdomen, the skin was wiped with an alcohol swab and allowed to air dry. Subsequently, control NPs (CS/DNA NPs) or test NPs (CS/γ-PGA/DNA NPs) containing 10 μg pEGFP-N2 in sterile DI water (5 μl) were loaded in a low-pressure gene gun and then bombarded into the skin. The helium pressure used was about 100 psi.

CLSM was used to visualize the penetration depth of the FITC-labeled NPs bombarded into the mouse skins using a low-pressure gene gun (about 50-150 psi). This non-invasive method allows for optical sectioning and imaging of the bombarded NPs in the mouse skins, without disrupting their structures. Both test NPs and control NPs are able to penetrate into the mouse skins after bombardment.

CS/DNA NPs were found in the superficial layer of epidermis (including the stratum corneum), whereas CS/γ-PGA/DNA NPs were able to penetrate into deeper regions in the epidermis. Also, there are more CS/γ-PGA/DNA NPs bombarded into the skin as compared with CS/DNA NPs. These observations could be attributed to the fact that CS/γ-PGA/DNA NPs are more compact in their internal structures (with a better integrity propensity; less propensity for breaking-up) and have a greater density than the density of their CS/DNA counterparts, thus having a larger momentum to penetrate into the skin barrier. Some aspects of the invention relate to a nanoparticle system that enhances penetrating efficiency overcoming the skin barrier when bombarded into the skin, wherein the nanoparticle system comprises a composition of CS, γ-PGA, and DNA.

The animal test results show more EGFP (enhanced green fluorescent protein) expression for CS/γ-PGA/DNA NPs than for CS/DNA NPs at 24 hours after bombardment. EGFP expression was mainly localized to the suprabasal layers of epidermis for the group bombarded by CS/γ-PGA/DNA NPs. In contrast, for the group of CS/DNA NPs, EGFP expression was limited to the superficial layer of epidermis. Selective gene expression in the epidermis has potential advantages in gene therapies for various epidermal disorders.

Ligand-Receptor Binding

Some aspects relate to a system, method and pharmaceutical composition of nanoparticles for lodging in tissue cells in situ of a patient, the nanoparticles comprising γ-PGA-PLA block copolymers that are conjugated with a ligand, wherein the ligand has ligand-receptor binding affinity for the ligand to bind a surface receptor of the tissue cells. In biochemistry, a receptor is a protein on the cell membrane or within the cytoplasm or cell nucleus that binds to a specific molecule (a ligand), such as a neurotransmitter, hormone, or other substance, and initiates the cellular response to the ligand. Ligand-induced changes in the behavior of receptor proteins result in physiological changes that constitute the biological actions of the ligands through a ligand-receptor binding process. Ligand binding to a receptor is an equilibrium process. Not every ligand that binds to a receptor it also activates the receptor. Antagonists bind to the receptor but do not activate it. This results in a receptor blockade that inhibits the binding of agonists. In one embodiment, the ligand of the present invention is a receptor-antagonist ligand.

A ligand that can bind to a receptor, alter the function of the receptor and trigger a physiological response is called an agonist for that receptor. Agonist binding to a receptor can be characterized both in terms of how much physiological response can be triggered and the concentration of the agonist that is required to produce the physiological response. High affinity ligand binding implies that a relatively low concentration of a ligand is adequate to maximally occupy a ligand binding site and trigger a physiological response. Low affinity binding implies that a relatively high concentration of a ligand is required before the binding site is maximally occupied and the maximum physiological response to the ligand is achieved. Only the agonists that can maximally stimulate the receptor are defined as a "full agonist". An agonist that can only partially activate the physiological response is called a "partial agonist". Ligands that bind to a receptor but fail to activate the physiological response are receptor "antagonists".

Receptors exist in different types, dependent on their ligand and function. Some receptor proteins are peripheral membrane proteins. Many hormone receptors and neurotransmitter receptors are transmembrane proteins. Transmembrane receptors are embedded in the lipid bilayer of cell membranes that allow the activation of signal transduction pathways in response to the activation by the binding molecule, or ligand. Metabotropic receptors are coupled to G proteins and affect the cell indirectly through enzymes that control ion channels. Ionotropic receptors contain a central pore that functions as a ligand-gated ion channel. Another major class of receptors is intracellular proteins such as those for steroid and intracrine peptide hormone receptors. These receptors often can enter the cell nucleus and modulate gene expression in response to the activation by the ligand. Some transmembrane receptors include, for example, Muscarinic acetylcholine receptor, Adenosine receptors, Adrenoceptors, GABA receptors, Angiotensin receptors, Cannabinoid receptors, Dopamine receptors, Glucagon receptors, Histamine receptors, Olfactory receptors, and so on.

In biochemistry, a ligand is a molecule that is able to bind to and form a complex with a biomolecule to serve a biological purpose. In a narrower sense, it is an effector molecule binding to a site on a target protein, by intermolecular forces such as ionic bonds, hydrogen bonds and Van der Waals forces. The docking (association) is usually reversible (dissociation). Actual irreversible covalent binding between a ligand and its target molecule is rare in biological systems. As opposed to the meaning in metalorganic and inorganic chemistry, it is irrelevant, whether or not the ligand actually binds at a metal site, as it is the case in hemoglobin. Ligand binding to receptors alters the chemical conformation, i.e. the three dimensional shape of the receptor protein. The conformational state of a receptor protein determines the functional state of a receptor. The tendency or strength of binding is called affinity. Ligands include substrates, inhibitors, activators, and neurotransmitters. Radioligands are radioisotope labeled compounds and used in vivo as tracers in PET studies and for in vitro binding studies.

The interaction of most ligands with their binding sites can be characterized in terms of a binding affinity. In general, high affinity ligand binding results from greater intermolecular force between the ligand and its receptor while low affinity ligand binding involves less intermolecular force between the ligand and its receptor. In general, high affinity binding involves a longer residence time for the ligand at its receptor binding site than is the case for low affinity binding. High affinity binding of ligands to receptors is often physiologically important when some of the binding energy can be used to cause a conformational change in the receptor, resulting in altered behavior of an associated ion channel or enzyme. One aspect of the invention comprises a nanoparticle having a high affinity binding ligand so that the nanoparticle stays with the tissue cells long enough to biodegrade and/or release encapsulated bioactive agent within the nanoparticle.

An advantage of administering a protein or peptide via a biodegradable nanoparticle capable of producing an immune response is the ability to cause the immunogen to be effectively presented to the animal or human over an extended period of time. Similarly, an advantage of administering siRNA via a biodegradable nanoparticle is the ability for siRNA to interfere with the expression of a specific gene over an extended period of time or in a control-release manner. RNA silencing, the process triggered by siRNA molecules, can turn off the ability of cancer cells to produce the key proteins that make them different from normal cells, and by doing so, stop malignancy in its tracks.

Some aspects of the invention provide a pharmaceutical composition of nanoparticles for lodging in a target tissue of an animal subject, each nanoparticle comprising a first component of a positively charged chitosan, a second component of negatively charged substrate that complexes with the first positively charged component, and at least one bioactive agent encapsulated within the nanoparticles. In one embodiment, the nanoparticles are biodegradable. In another embodiment, the nanoparticle is about 50 µm to 500 µm in size.

Freeze-Dried Nanoparticles

A pharmaceutical composition of nanoparticles of the present invention may comprise a first component of at least one bioactive agent, a second component of chitosan (including regular molecular weight and low molecular weight chitosan), and a third component that is negatively charged. In one embodiment, the second component dominates on a surface of the nanoparticle. In another embodiment, the low molecular weight chitosan has a molecular weight lower than that of a regular molecular weight chitosan. The nanoparticle may further comprise tripolyphosphate and magnesium. For example, a first solution of (2 ml 0.1% γ-PGA aqueous solution @pH 7.4+0.05% Insulin+0.1% Tripolyphosphate (TPP)+0.2% MgSO4) is added to a base solution (10 ml 0.12% chitosan aqueous solution @pH 6.0) as illustrated in Example no. 4 under magnetic stirring at room temperature. Nanoparticles were collected by ultracentrifugation at 38,000 rpm for 1 hour. Supernatants were discarded and nanoparticles were resuspended in deionized water for freeze-drying preparation. Other operating conditions or other bioactive agent (such as protein, peptide, siRNA, growth factor, the one defined and disclosed herein, and the like) may also apply.

Several conventional coating compounds that form a protective layer on particles are used to physically coat the nanoparticles before a freeze-drying process. The coating compounds may include trehalose, mannitol, glycerol, and the like. Trehalose, also known as mycose, is an alpha-linked (disaccharide) sugar found extensively but not abundantly in nature. It can be synthesized by fungi, plants and invertebrate animals. It TABLE 4-continued Properties of nanoparticles before and after an exemplary freeze-drying process.

| NPs solution | | A: DI Water A: DI water + NPs (volume 1:1), freeze-dried | | B: Trehalose B: Trehalose + NPs (volume 1:1), freeze-dried | | | | C: Mannitol C: Mannitol + NPs (volume 1:1), freeze-dried | | | D: Glycerol D: Glycerol + NPs (volume 1:1), freeze-dried | | | |
|---|---|---|---|---|---|---|---|---|---|---|---|---|---|---|
| Conc. | 2.50% | Conc | | Conc. | 2.50% | 5.00% | 10.00% | Conc. | 2.50% | 5.00% | Conc. | 2.50% | 5.00% | 10.00% |
| Kcps | 352.2 | Kcps | 465.3 | Kcps | 363.7 | 327.7 | 352.2 | Kcps | 305.4 | 303.7 | Kcps | 796.1 | 356.1 | 493.3 |
| PI | 0.291 | PI | 1 | PI | 0.361 | 0.311 | 0.266 | PI | 0.467 | 0.651 | PI | 1 | 1 | 1 |
| Zeta Potential | 25.3 | Zeta Potential | | Zeta Potential | 25.6 | 24.6 | 24.7 | Zeta Potential | 24.4 | 25.3 | Zeta Potential | | | |

Nanoparticle Loaded with siRNA Compound

One aspect of the invention provides a method of administering a bioactive agent into tissue cells in an animal subject by injecting bioactive agent-containing nanoparticles of the present invention intravascularly, wherein the bioactive agent is RNA or siRNA. Ribonucleic acid (RNA) is a nucleic acid polymer consisting of nucleotide monomers that plays several important roles in the processes that translate genetic information from deoxyribonucleic acid (DNA) into protein products. RNA acts as a messenger between DNA and the protein synthesis complexes known as ribosomes, forms vital portions of ribosomes, and acts as an essential carrier molecule for amino acids to be used in protein synthesis. RNA is very similar to DNA, but differs in a few important structural details. RNA nucleotides contain ribose sugars while DNA contains deoxyribose and RNA uses predominantly uracil instead of thymine present in DNA. RNA is transcribed from DNA by enzymes called RNA polymerases and further processed by other enzymes. RNA serves as the template for translation of genes into proteins, transferring amino acids to the ribosome to form proteins, and translating the transcript into proteins.

Figure 12:
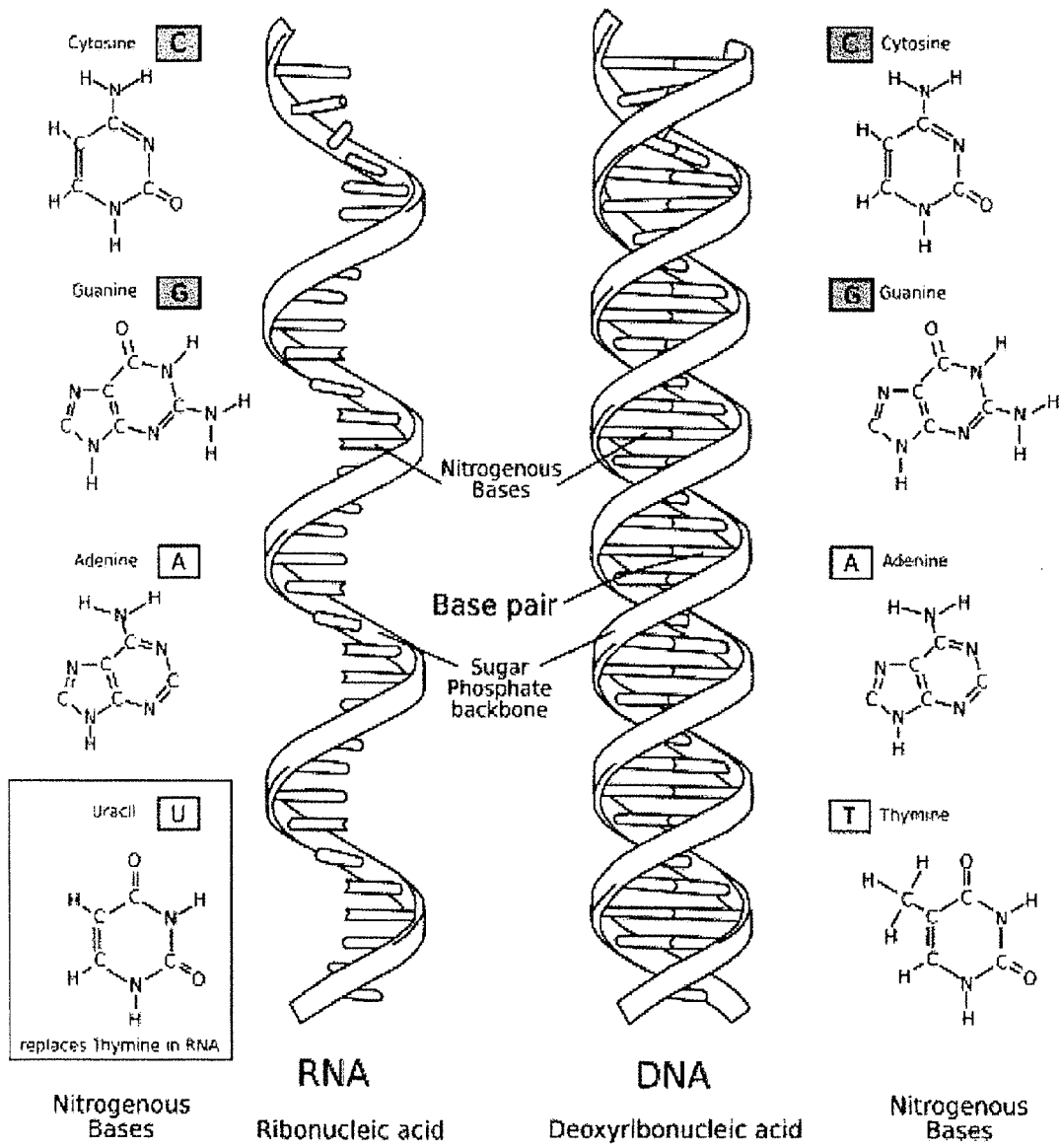
FIG. 12 show chemical and stereochemical structures for a representative RNA and DNA.

RNA is a polymer with a ribose and phosphate backbone and four different nucleotide bases: adenine, guanine, cytosine, and uracil. The first three are the same as those found in DNA, but in RNA thymine is replaced by uracil as the base complementary to adenine. This base is also a pyrimidine and is very similar to thymine. In DNA, however, uracil is readily produced by chemical degradation of cytosine, so having thymine as the normal base makes detection and repair of such incipient mutations more efficient. Thus, uracil is appropriate for RNA, where quantity is important but lifespan is not, whereas thymine is appropriate for DNA where maintaining sequence with high fidelity is more critical. FIG. 12 show chemical and stereochemical structures for a representative DNA and RNA (Wikimedia Commons).

There are also numerous modified bases and sugars found in RNA that serve many different roles. Pseudouridine (Ψ), in which the linkage between uracil and ribose is changed from a C—N bond to a C—C bond, and ribothymidine (T), are found in various places (most notably in the TΨC loop of tRNA). Another notable modified base is hypoxanthine (a deaminated Guanine base whose nucleoside is called Inosine). Inosine plays a key role in the Wobble Hypothesis of the Genetic Code. There are nearly 100 other naturally occurring modified nucleosides, of which pseudouridine and nucleosides with 2'-O-methylribose are by far the most common. The specific roles of many of these modifications in RNA are not fully understood. However, it is notable that in ribosomal RNA, many of the post-translational modifications occur in highly functional regions, such as the peptidyl transferase center and the subunit interface, implying that they are important for normal function.

The most important structural feature of RNA, that distinguishes it from DNA is the presence of a hydroxyl group at the 2'-position of the ribose sugar. The presence of this functional group enforces the C3'-endo sugar conformation (as opposed to the C2'-endo conformation of the deoxyribose sugar in DNA) that causes the helix to adopt the A-form geometry rather than the B-form most commonly observed in DNA. This results in a very deep and narrow major groove and a shallow and wide minor groove. A second consequence of the presence of the 2'-hydroxyl group is that in conformationally flexible regions of an RNA molecule (that is, not involved in formation of a double helix), it can chemically attack the adjacent phosphodiester bond to cleave the backbone.

Small interfering RNA (siRNA), sometimes known as short interfering RNA or silencing RNA, are a class of 20-25 nucleotide-long double-stranded RNA molecules that play a variety of roles in biology. Most notably, siRNA is involved in the RNA interference (RNAi) pathway where the siRNA interferes with the expression of a specific gene. In addition to their role in the RNAi pathway, siRNAs also act in RNAi-related pathways, e.g. as an antiviral mechanism or in shaping the chromatin structure of a genome; the complexity of these pathways is only now being elucidated.

SiRNAs were first discovered by David Baulcombe's group in Norwich, England, as part of post-transcriptional gene silencing (PTGS) in plants, and published their findings in *Science* in a paper titled "A species of small antisense RNA in posttranscriptional gene silencing in plants". Shortly thereafter, in 2001, synthetic siRNAs were then shown to be able to induce RNAi in mammalian cells by Thomas Tuschl and colleagues in a paper published in *Nature*. This discovery led to a surge in interest in harnessing RNAi for biomedical research and drug development.

SiRNAs have a well-defined structure: a short (usually 21-nt) double-strand of RNA (dsRNA) with 2-nt 3' overhangs on either end:

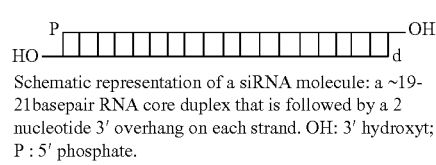

Schematic representation of a siRNA molecule: a ~19-21basepair RNA core duplex that is followed by a 2 nucleotide 3' overhang on each strand. OH: 3' hydroxyt; P : 5' phosphate.

Each strand has a 5' phosphate group and a 3' hydroxyl (—OH) group. This structure is the result of processing by dicer, an enzyme that converts either long dsRNAs or small hairpin RNAs into siRNAs. SiRNAs can also be exogenously (artificially) introduced into cells by various transfection methods to bring about the specific knockdown of a gene of interest. Essentially any gene of which the sequence is known can thus be targeted based on sequence complementarity with an appropriately tailored siRNA. This has made siRNAs an important tool for gene function and drug target validation studies in the post-genomic era.

RNA interference (RNAi) is a phenomenon in which the introduction of double-stranded RNA (dsRNA) into a diverse range of organisms and cell types causes degradation of the complementary mRNA. Upon introduction into the cell, long dsRNAs enter a cellular pathway that is commonly referred to as the RNA interference pathway. First, the dsRNA's are cleaved into short 21-25 nucleotide small interfering RNAs, or siRNAs, by a ribonuclease known as Dicer. The siRNAs subsequently assemble with protein components into an RNA-induced silencing complex (RISC). The siRNA strands are then unwound to form activated RISCs. These activated RISCs then bind to complementary RNA molecules by base pairing interactions between the siRNA antisense strand and the mRNA. The bound mRNA is cleaved and sequence specific degradation of mRNA results in gene silencing. Although there are different methods to generate siRNA for gene silencing, the easiest and most efficient way to achieve RNAi is to use synthetic small-interfering RNA (siRNA).

In an exemplary illustration, RNA silencing, the process triggered by siRNA molecules, can turn off the ability of cancer cells to produce the key proteins that make them different from normal cells, and by doing so, stop malignancy in its tracks. Early proof-of-principle experiments in various tumor cells showed quickly that RNA silencing had great potential as a means for treating cancer.

RNA oligos are susceptible to degradation by exogenous ribonucleases introduced during handling. RNase-free reagents and supplies should be used. Oligonucleotides may be re-suspended at a convenient concentration in RNase-free sterile water. The use of DEPC-treated water is not recommended. DEPC-treated water is deionized diethylpyrocarbonate treated and 0.22 μm membrane-filtered. Dried RNA oligos are usually stable for 1 year at −20° C. Once re-suspended, oligonucleotides solutions are best kept frozen at −20° C. for several weeks and may remain stable for several months. The most important factor in storing working solutions is using nuclease-free, sterile water. Drying down of your oligos and keeping them at −20° C. is recommended for long-term storage. Some aspects of the invention relate to a siRNA-containing nanoparticle that has been lyophilized (for example, using a freeze dryer by Eyela Co. Ltd, Tokyo, Japan) and stored at −20° C. until it is ready for administering into the tissue cells intravascularly.

The function of a gene can be determined based on the behavior of cells in which the level of gene expression or level of activity of the gene product has been reduced. Experimental procedures can be used to specifically inactivate or silence a target gene or inhibit the activity of its gene product. Inhibition of protein activity can be brought about at the level of gene transcription, protein translation or post translational modifications. For instance, the activity of a protein can be inhibited by directly inhibiting the activity of the protein such as altering a catalytic domain or alternatively by reducing the amount of the protein in the cell by reducing the amount of mRNA encoding the protein. In each case, the level of protein activity in the cell is reduced. Various techniques can be used to knock down the activity of a protein and these include knockout technologies (antibodies, antisense RNA, and RNA interference) and compounds that specifically inhibit the protein activity.

The ability to specifically knock down expression of a target gene by siRNA has many benefits. For example, siRNA could be used to mimic true genetic knockout animals to study gene function. There have been reports of using siRNA for various purposes including the inhibition of luciferase gene expression in human cells, (see U.S. Patent Application publication no. 2002/0132788).

The in situ nano-projectile bombardment of the present invention discloses a method of administering a nanoparticle into cells intravascularly in an animal subject, the nanoparticle comprising potent and stable siRNA compounds (or siRNA-containing compounds) to silence the genes that causes serious diseases. The potent and stable siRNA compound may comprise a polynucleotide or vector for expressing short interfering RNAs (siRNAs) to inhibit the expression of a target gene. One aspect of the invention relates to delivering polynucleotides encoding polypeptides to vertebrate cells in vivo, preferably via a vein or an artery. The siRNA compound may include a composition comprising the siRNA of interest and a pharmaceutically acceptable carrier or diluent. The ability to inhibit or disrupt the function of a specific gene is highly desirable. The ability to modulate the expression of a mutated allele or of an inappropriately expressed wild type allele in various diseases or disorders may therefore be used to provide therapies to treat the disorders.

The nanoparticles of the present invention may further comprise an adenovirus vector, wherein the adenovirus vector comprises a polynucleotide construct that may be in any of several forms, including, but not limited to, DNA, DNA encapsulated in an adenovirus coat, DNA packaged in another viral or viral-like form (such as herpes simplex, and AAV), DNA encapsulated in liposomes, DNA complexed with polylysine, complexed with synthetic polycationic molecules, conjugated with transferrin, and complexed with compounds such as PEG to immunologically "mask" the molecule and/or increase half-life, and conjugated to a non-viral protein. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides. For purposes of this invention, adenovirus vectors are replication-competent in a target cell. In an alternate embodiment, the nanoparticles of the present invention may further comprise an adenovirus vector, wherein the adenovirus vector comprises a siRNA.

Dual-Particle Tumor Targeting System

In the past few decades, scientists hypothesized that the proteins presented at the surface of a cancer cell will become useful markers to distinguish a malignant cell from normal tissue. Their goal has not been achieved yet because the difference between the surface protein expression patterns of normal and abnormal cells are negligible. It is difficult to find a protein specifically expressed on a tumor cell surface but not on the surface of normal cells. Laboratory experiments and clinical trial results have proved that the drugs or toxins targeting the "tumor marker" are not able to prevent the normal tissue from impairment completely. For example, a clinical trial with immunotoxin-diphtheria toxin/GMCSF fusion protein (DT388GMCSF) on 31 patients with refractory or relapsed acute myeloid leukemia revealed dose-related toxicity such as liver injury, fever, chills, hypoxemia, and transient post-infusion hypotension (Clin Cancer Res 2002; 8:1004-1013).

Tissue functions depend on adequate supply of oxygen and nutrition through blood vessels. The term "angiogenesis" is used to describe the growth of new blood vessels sprouting from preexisting vasculature. Angiogenesis is involved in many physiological and pathological processes such as wound healing, age-related macular degeneration, and tumor progression. Solid tumors require a functional blood supply for their continued growth, and the established tumor vasculature is therefore an attractive target for therapy (Nature Rev. Cancer 2005; 5:423-435). Therapeutic vascular targeting has so far concentrated on anti-angiogenic approaches, which aim to prevent the neovascularization process in tumors. It is disclosed herein that the specific pathological property of most newly formed, immature blood vessels in solid tumors is utilized to direct the specially designed nanoparticles to target these tumors, rather than directly destroy the angiogenic vasculature. This phenomenon is called "EPR effect" (enhanced permeability and retention effect).

The most powerful growth factor secreted by tumor that promotes angiogenesis is VEGF (vascular endothelial growth factor), also named as VPF (vascular permeability factor), which does not only support new blood vessel formation but also enhance permeability of the vasculature. In addition to this protein growth factor, tumor cells also produce other factors such as bradykinin, nitric oxide (NO) and matrix metalloproteinases (MMP) that further increase the permeability of capillaries within a tumor. Based on the synergistic effect of molecules mentioned above, tumor vasculature becomes leaky and allows large substances to pass through. The previous data (Journal of Controlled Release 2000; 65:271-284) using macromolecules and synthetic polymers that hardly penetrate normal blood vessel showed that they are entrapped and accumulate in solid tumors and that they are retained there at high concentrations for prolonged periods. This EPR effect for macromolecules has been observed in many human solid tumors, including hepatoma, renal cancer, lung cancer, and brain tumors. When this kind of drug carrier is used, large amount of polymer or macromolecules will still remain in circulating blood, and finally be caught by lymph nodes, liver, kidney or other organs (Journal of Controlled Release 2000; 65:271-284). The above observation suggests that normal tissue would still possibly be harmed by administration of macromolecules-anticancer drug conjugates that target tumors by EPR effect.

Human body is a very complicated bio-system that consists of billions of different cells and myriads of proteins. As described above, it is impossible to distinguish a tumor from normal tissue and treat the tumor solely with either ligand-mediated specific tumor cell targeting approach or EPR effect-mediated tumor vasculature targeting approach. Thus, it is beneficial to combine advantages of the two targeting methods and limit their shortcomings.

Some aspects of the invention relate to a dual-particle tumor targeting system. By ways of illustration, hepatoma (liver cancer) is used as an experimental demo model. Nanoparticles composed of biodegradable polymers of the present invention are used as drug and gene carriers. A first nanoparticle(s) conjugates with proteins or ligands (for example, galactosamine) which bind to the surface receptor (for example, ASGP receptor) of hepatocyte (normal cells) and hepatocyte-derived cell lines such as hepatoma (abnormal cells). The first conjugated nanoparticle is swallowed up (that is, up-taken) by receptor-mediated endocytosis of those cells. A second nanoparticle(s) that depends upon the EPR effect would accumulate in the angiogenic vasculature within hepatoma. The biodistribution of the above-disclosed two nanoparticles of the dual-particle tumor targeting system would only co-localize within hepatoma to be effective but not in other organs of the human body.

In a co-pending patent application, U.S. application Ser. No. 11/029,082, filed Jan. 4, 2005 and entitled "Nanoparticles For Paracellular Drug Delivery", now U.S. Pat. No. 7,265,090, entire contents of which are incorporated herein by reference, it is disclosed a nanoparticle made of chitosan or a mixture of chitosan and γ-PGA. In one embodiment, the chitosan is a low molecular weight chitosan. Some aspects of the invention provide a dual-particle tumor targeting system comprising a first ligand-mediated targeting nanoparticle and a second EPR-mediated targeting nanoparticle, wherein the first, the second, or both nanoparticles are made of chitosan or a mixture of chitosan and γ-PGA or a negatively charged substrate.

In a co-pending patent application, U.S. application Ser. No. 11/284,734, filed Nov. 21, 2005 and entitled "Nanoparticles For Protein Drug Delivery", now U.S. Pat. No. 7,282,194, entire contents of which are incorporated herein by reference, it is disclosed a nanoparticle made of crosslinked chitosan or a mixture of crosslinked chitosan and γ-PGA. In one embodiment, the chitosan is a low molecular weight chitosan. Some aspects of the invention provide a dual-particle tumor targeting system comprising a first ligand-mediated targeting nanoparticle and a second EPR-mediated targeting nanoparticle, wherein the first, the second, or both nanoparticles are made of crosslinked chitosan or a mixture of crosslinked chitosan and γ-PGA.

In a further embodiment, it is disclosed to produce cytotoxic effect in tumor cells by using enzyme/substrate system. As is well known to one ordinary skilled in the art, HSV (Herpes-simplex-virus) thymidine kinase gene does not exist in human body; the product of this gene is thymidine kinase enzyme that is nontoxic for human cells. The enzyme only acts on its substrate, e.g., the pro-drug ganciclovir, and thus turn ganciclovir into DNA analogue which can be incorporated into replicating chromosome and thereafter interrupt the DNA replication procedure. After that, cell cycle would be arrested at G2-M phase and then go through apoptosis (J Nucl Med 1997; 38:1230-1233; Science 1992; 256:1550-1552). In one embodiment, the HSV thymidine kinase gene is loaded in a nanoparticle and is used as a suicide gene.

The pro-drug ganciclovir is packaged in the first nanoparticle(s) that targets the hepatocyte/hepatoma cell lines by conjugated with galactosamine, the ligand of ASGP receptor of liver cell surface. The second nanoparticle(s) using EPR effect-mediated targeting contains the suicide gene, for example, HSV thymidine kinase gene. The first and second nanoparticles would only be effective when they co-localize in tumors as described herein. After cancer cells internalize the first and second nanoparticles together, thymidine kinase would digest ganciclovir and produce cytotoxic effect, and then these cancer cells would be killed or inactivated.

The drug delivery system of the present invention could suppress the tumor progression and destroy the abnormal tissue specifically. The other tissues/organs of human body may gather either the first nanoparticle alone or the second nanoparticle alone, but not produce any cytotoxic effect due to absence of any conjugatable ingredient, thus maintain the side effects at minimum. In one embodiment, the conjugatable ingredient may comprise galactosamine from liver tumor or a ligand of other tumor receptors. For additional safety precaution, a hepatocyte specific promoter could be used to make sure the HSV-thymidine kinase gene would only express at liver-related cells. FIG. 10 shows a dual-particle tumor targeting system comprising a first ligand-mediated targeting nanoparticle(s) with a pro-drug and a second EPR mediated targeting nanoparticle(s) with a thymidine kinase gene. Some aspects of the invention provide a dual-particle tumor targeting system comprising a first ligand-mediated targeting nanoparticle(s) and a second EPR-mediated targeting nanoparticle(s).

In a first alternate embodiment to the dual-particle tumor targeting system of FIG. 10, the matrix metalloproteinase (MMP) promoters would be used to regulate the expression of HSV-thymidine kinase (HSV-TK) gene in the second nanoparticles. As is known to one ordinary skilled in the art, matrix metalloproteinases express on most of invasive cancer cells and help them to degrade the extracellular matrix (ECM) and proceed metastasis (Nature Reviews of Cancer 2003; 3:489-501). Using MMP promoter/HSV-TK gene construct enables that this suicide gene would only express within the invasive cancer cells.

Matrix metalloproteinases (MMPs) are zinc-dependent endopeptidases; other family members are adamalysins, serralysins, and astacins. The MMPs belong to a larger family of proteases known as the metzincin superfamily. Collectively they are capable of degrading all kinds of extracellular matrix proteins, but also can process a number of bioactive molecules. They are known to be involved in the cleavage of cell surface receptors, the release of apoptotic ligands (such as the FAS ligand), and chemokine inactivation or activation. MMPs are also thought to play a major role on cell behaviors such as cell proliferation, migration (adhesion/dispersion), differentiation, angiogenesis, apoptosis and host defense. MMPs are distinguished from other endopeptidases by their dependence on metal ions as cofactors, their ability to degrade extracellular matrix, and their specific evolutionary DNA sequence. The MMPs share a common domain structure. The three common domains are the pro-peptide, the catalytic domain and the haemopexin-like C-terminal domain which is linked to the catalytic domain by a flexible hinge region.

Archetypal MMPs include: (A) the collagenases that are capable of degrading triple-helical fibrillar collagens into distinctive 3/4 and 1/4 fragments, for examples, MMP-1 (interstitial collagenase), MMP-8 (neutrophil collagenase), MMP-13 (collagenase 3), MMP-18, MMP-14 (MT1-MMP), and MMP-2; (B) the stromelysins that display a broad ability to cleave extracellular matrix proteins but are unable to cleave the triple-helical fibrillar collagens, for examples, MMP-3 (stromelysin 1, progelatinase), MMP-10 (stromelysin 2), and MMP-11 (stromelysin 3); (C) other MMPs, for examples, MMP-12 (metallloelastase, macrophage elastase), MMP-19 (RASI-1), Enamelysin (MMP-20), and MMP-27 (MMP-22, C-MMP); (D) the Matrylysins, for examples, MMP-7 (Matrylysin), and MMP-26 (Matrylysin-2); (E) the Gelatinases, for examples, MMP-2 (expressed in most tissues) and MMP-9 (predominantly found in neutrophils); (F) convertase-activatable MMPs, for examples, MMP-11 (stromelysin 3), MMP-21 (X-MMP), and MMP-28 (epilysin); (G) the Membrane Bound MMPs, for examples, the type-II transmembrane cysteine array MMP-23, the glycosyl phosphatidylinositol-attached MMPs 17 and 25 (MT4-MMP and MT6-MMP respectively), and the type-I transmembrane MMPs 14, 15, 16, 24 (MT1-MMP, MT2-MMP, MT3-MMP, and MT5-MMP respectively); and (H) MMP-23A and MMP-23B.

In a second alternate embodiment to the dual-particle tumor targeting system of FIG. 10, the HSV-TK gene is co-formulated or combined with an endothelial cells specific promoter response for angiogenesis (for example, VEGF receptor-2 promoter, $\alpha_v\beta_3$ integrin promoter, bFGF receptor promoter, and the like), the suicide gene would only destroy the newly formed, immature capillaries within a tumor and shutdown the blood supply to the tumor. The vascular endothelial growth factor (VEGF) receptor-2 (Flk-1) is the first endothelial receptor tyrosine kinase to be expressed in angioblast precursors, and its function is essential for the differentiation of endothelial cells and hematopoietic precursors (Blood 1999; 93:4284-4292). Some aspects of the invention provide a method for selectively inhibiting angiogenesis within hepatoma. Furthermore, the second nanoparticle(s) of the system might contain EC-specific promoter/HSV-TK gene constructed plasmid that would further enhance anti-angiogenesis by conjugating with the endothelial cells specific targeting domain at the surface of this second nanoparticle. This EC-specific targeting domain could enhance the specificity for endothelial cells targeting and lead to more efficient inhibition of angiogenesis within a tumor by the suicide gene. The pathological angiogenesis to be treated may include tumor, atherosclerotic plaques, retinopathy, rheumatoid arthritis, and the like.

Figure 11:
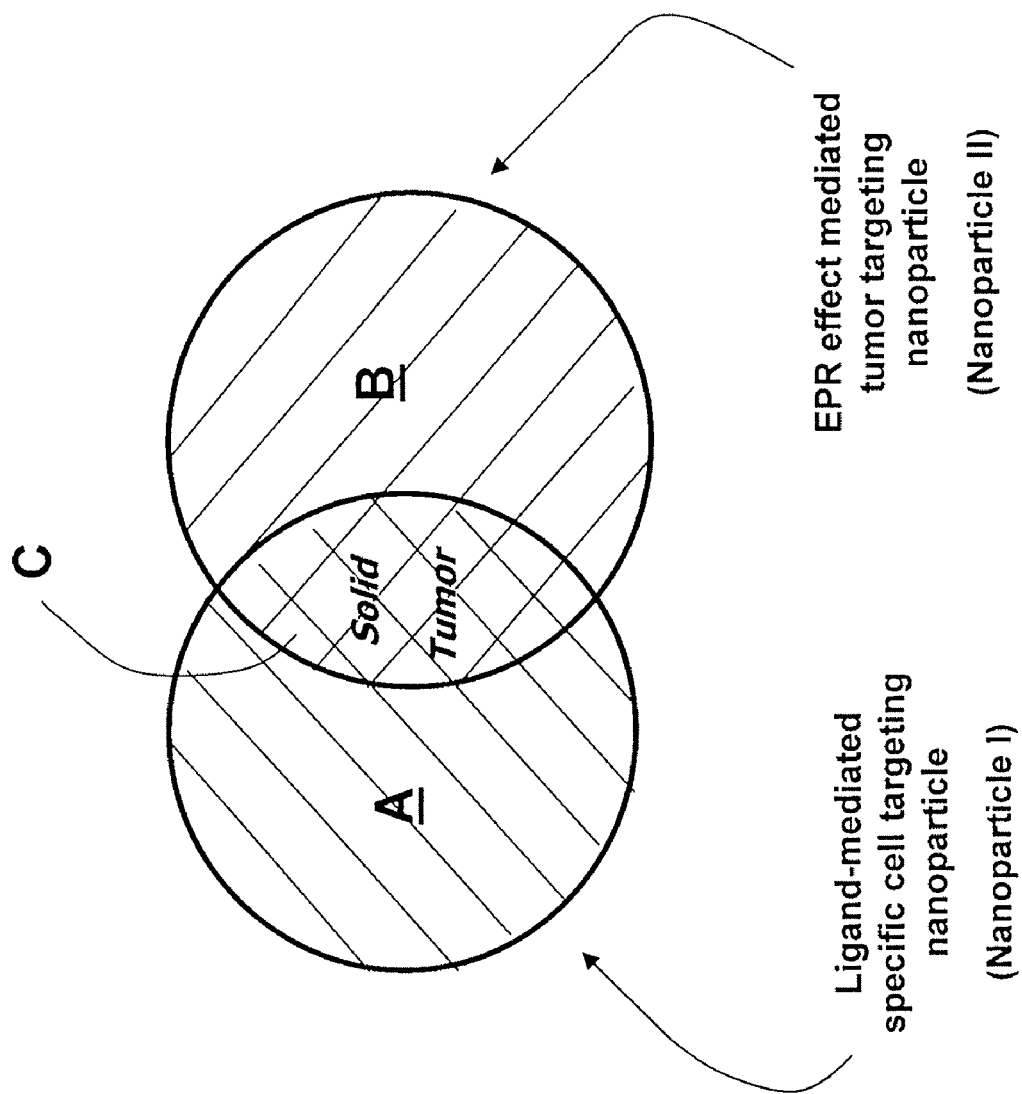
FIG. 11 shows a dual-particle tumor targeting system for locating a tumor.

Clinically, unable to detect (or unable to reliably detect) the early-stage tumors and metastases when they are quiescent with a small size is a major problem for cancer therapy. In addition to the therapeutic ability as disclosed herein, the "dual-particle tumor targeting system" of the invention has potential application to specifically pin point, target, identify, or locate the location of very small tumors. FIG. 11 shows a dual-particle tumor targeting system for locating a tumor, comprising a first ligand-mediated specific cell targeting nanoparticle and a second EPR mediated tumor targeting nanoparticle. The overlapped zone C between the first nanoparticle targeting zone A and the second nanoparticle targeting zone B is where the tumor could be located.

EXAMPLE NO. 16

Locating a Liver Tumor in a Patient

By ways of illustration, a dose of nanoparticles is administrated to a patient, wherein the dose comprises a first ligand-mediated cell targeting nanoparticle(s) and a second EPR-mediated tumor targeting nanoparticle(s). In one embodiment, the first or second nanoparticle is biodegradable. In another embodiment, the first or second nanoparticle is consisted of γ-PGA-PLA block copolymers. The first nanoparticle is conjugated with galactosamine for targeting hepatoma, wherein the first nanoparticle further comprises a radiotracer (for example, $^{18}$F-acyclovir for liver targeting) for locating purposes using a radioactivity counter or imaging instrument. The second nanoparticle comprises HSV thymidine kinase gene that is regulated by hepatocyte. The liver tumor cells that express this gene after up-taking both the first and the second nanoparticles possess radioactivity. It becomes feasible to take the radiograph of a patient to locate the liver tumor by using a PET (positron emission tomography) scan technique.

In a further alternate embodiment to the dual-particle tumor targeting system of FIG. 10, the HSV-TK suicide gene packaged in the second nanoparticle becomes a receptor gene whereas the first nanoparticle contains the radiotracer, for example, $^{131}$I/$^{124}$I-FIAU for RG2/W256 tumor, $^{18}$F-acyclovir for liver tissue, or $^{18}$F-FHPG for 9L glioma tissue. The enzyme produced by HSV-TK gene would receive and digest the radiotracer resulting in immovable metabolite with radioactivity and then stays inside the tumor cells that express this gene. Using PET (positron emission tomography), SPET (single photon emission tomography), MRI (magnetic resonance imaging) scan technique to take the radiograph of a patient, we could monitor/image the location, size and number of in situ tumors, and metastases.

EXAMPLE NO. 17

Micelles

Figure 18:
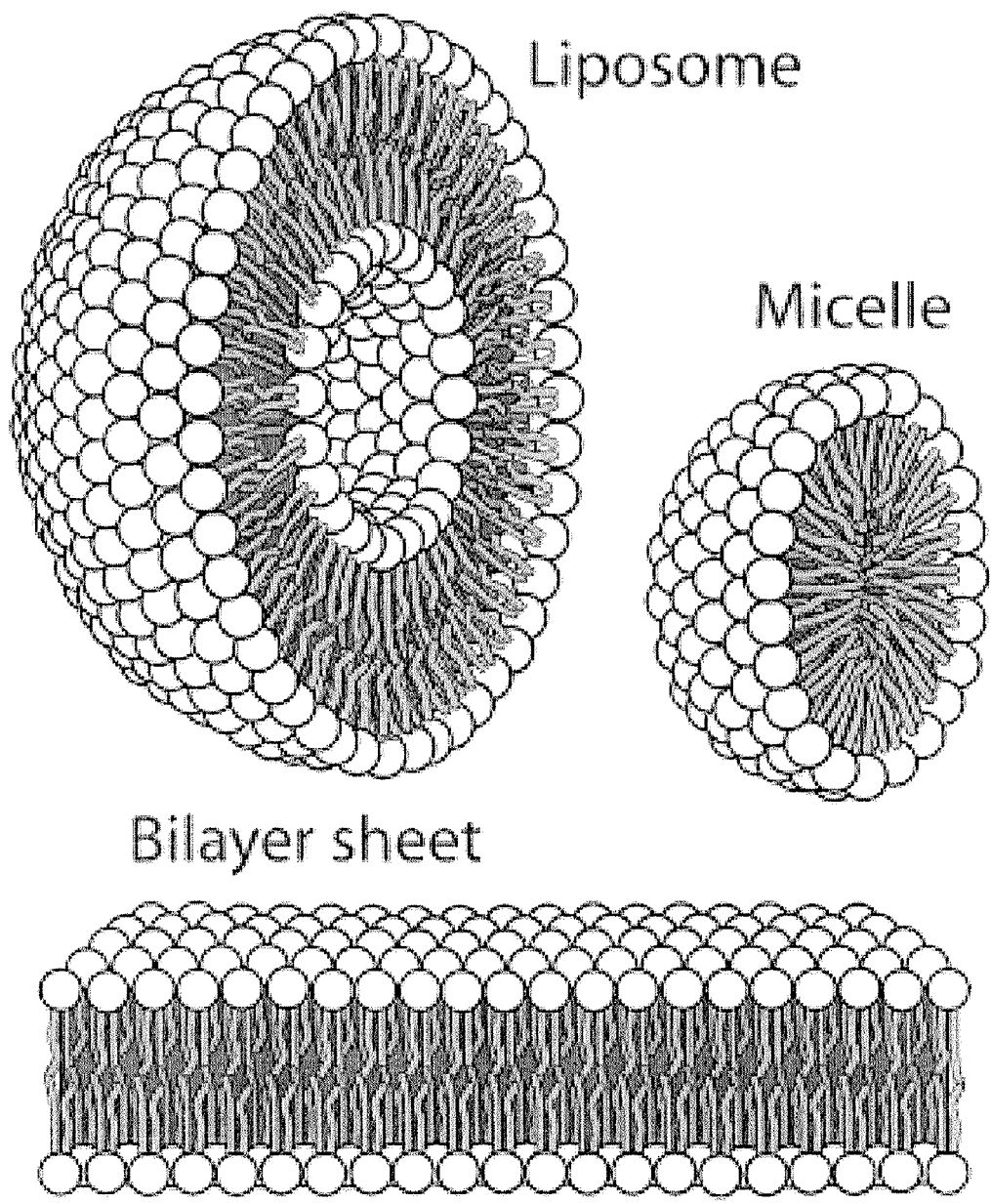
FIG. 18 shows cross-sections of different structures that phospholipids can take in an aqueous solution. The circles are the hydrophilic heads and the wavy lines are the fatty acyl side chains.

A micelle is an aggregate of surfactant molecules dispersed in a liquid colloid. A typical micelle in aqueous solution forms an aggregate with the hydrophilic "head" regions in contact with surrounding solvent, sequestering the hydrophobic single tail regions in the micelle centre (see FIG. 18). This phase is caused by the insufficient packing issues of single tailed lipids in a bilayer. The difficulty filling all the volume of the interior of a bilayer, while accommodating the area per head group forced on the molecule by the hydration of the lipid head group leads to the formation of the micelle. This type of micelle is known as a normal phase micelle (oil-in-water micelle). Inverse micelles have the headgroups at the centre with the tails extending out (water-in-oil micelle). Micelles are approximately spherical in shape. Other phases, including shapes such as ellipsoids, cylinders, and bilayers are also possible. The shape and size (typically a few nanometers to micrometers) of a micelle is a function of the molecular geometry of its surfactant molecules and solution conditions such as surfactant concentration, temperature, pH, and ionic strength. The process of forming micelles is known as micellization and forms part of the phase behavior of many lipids according to their polymorphism.

The ability of a soapy solution to act as a detergent has been recognized for centuries. The existence of "colloidal ions" or the highly mobile, spontaneously formed clusters came to be called micelles. Individual surfactant molecules that are in the system but are not part of a micelle are called "monomers." Lipid micelles represent a molecular assembly in which the individual components are thermodynamically in equilibrium with monomers of the same species in the surrounding medium. In water, the hydrophilic "heads" of surfactant molecules are always in contact with the solvent, regardless of whether the surfactants exist as monomers or as part of a micelle. However, the lipophilic "tails" of surfactant molecules have less contact with water when they are part of a micelle—this being the basis for the energetic drive for micelle formation. In a micelle, the hydrophobic tails of several surfactant molecules assemble into an oil-like core the most stable form of which has no contact with water. By contrast, surfactant monomers are surrounded by water molecules that create a "cage" of molecules connected by hydrogen bonds. This water cage is similar to a clathrate and has an ice-like crystal structure and can be characterized according to the hydrophobic effect. The extent of lipid solubility is determined by the unfavorable entropy contribution due to the ordering of the water structure according to the hydrophobic effect.

Micelles composed of ionic surfactants have an electrostatic attraction to the ions that surround them in solution, the latter known as counterions. Although the closest counterions partially mask a charged micelle (by up to 90%), the effects of micelle charge affect the structure of the surrounding solvent at appreciable distances from the micelle. Ionic micelles influence many properties of the mixture, including its electrical conductivity. Adding salts to a colloid containing micelles can decrease the strength of electrostatic interactions and lead to the formation of larger ionic micelles. This is more accurately seen from the point of view of an effective change in hydration of the system.

Micelles only form when the concentration of surfactant is greater than the critical micelle concentration (CMC), and the temperature of the system is greater than the critical micelle temperature, or Kraft temperature. The formation of micelles can be understood using thermodynamics: micelles can form spontaneously because of a balance between entropy and enthalpy. In water, the hydrophobic effect is the driving force for micelle formation, despite the fact that assembling surfactant molecules together reduces their entropy. At very low concentrations of the lipid, only monomers are present in true solution. As the concentration of the lipid is increased, a point is reached at which the unfavorable entropy considerations, derived from the hydrophobic end of the molecule, become dominant. At this point, the lipid hydrocarbon chains of a portion of the lipids must be sequestered away from the water. Therefore, the lipid starts to form micelles. Broadly speaking, above the CMC, the entropic penalty of assembling the surfactant molecules is less than the entropic penalty of caging the surfactant monomers with water molecules. Also important are enthalpy considerations, such as the electrostatic interactions that occur between the charged parts surfactants.

In a non-polar solvent, it is the exposure of the hydrophilic head groups to the surrounding solvent that is energetically unfavorable, giving rise to a water-in-oil system. In this case, the hydrophilic groups are sequestered in the micelle core and the hydrophobic groups extend away from the centre. These inverse micelles are proportionally less likely to form on increasing headgroup charge, since hydrophilic sequestration would create highly unfavorable electrostatic interactions.

When surfactants are present above the CMC, they can act as emulsifiers that will allow a compound that is normally insoluble (in the solvent being used) to dissolve. This occurs because the insoluble species can be incorporated into the micelle core, which is itself solubilized in the bulk solvent by virtue of the head groups' favorable interactions with solvent species. The most common example of this phenomenon is detergents, which clean poorly soluble lipophilic material (such as oils and waxes) that cannot be removed by water alone. Detergents also clean by lowering the surface tension of water, making it easier to remove material from a surface. The emulsifying property of surfactants is also the basis for emulsion polymerization.

Figure 16:
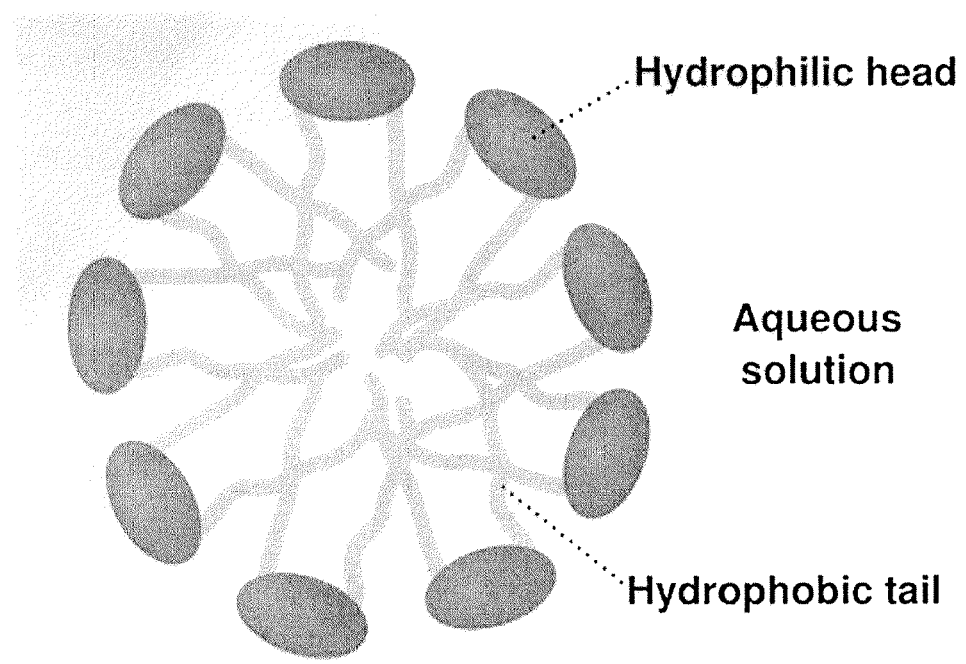
FIG. 16 shows scheme of a micelle formed by phospholipids in an aqueous solution.
Figure 17:
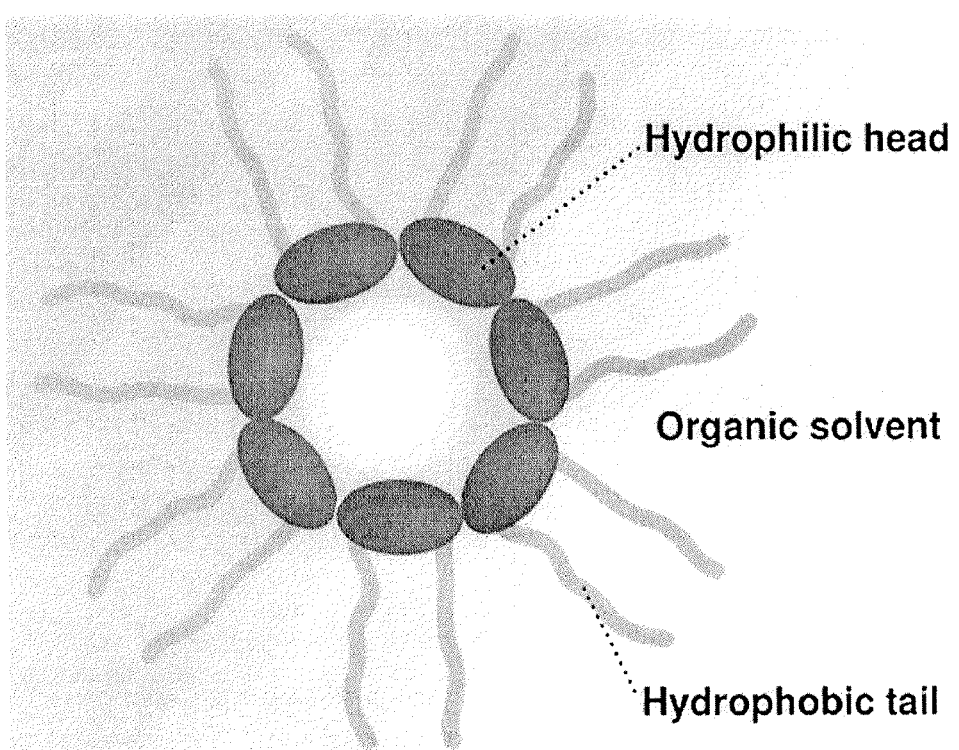
FIG. 17 shows scheme of a micelle formed by phospholipids in an organic solvent.

Micelle formation is essential for the absorption of fat-soluble vitamins and complicated lipids within the human body. Bile salts formed in the liver and secreted by the gall bladder allow micelles of fatty acids to form. This allows the absorption of complicated lipids (e.g., lecithin) and lipid soluble vitamins (A, D, E and K) within the micelle by the small intestine. FIG. 16 shows a schematic of a micelle formed by phospholipids in an aqueous solution, whereas FIG. 17 shows a schematic of a micelle formed by phospholipids in an organic solvent. In one embodiment, either scheme of micelles may be feasible to function as a drug delivery vehicle or be encapsulated in a nanoparticle formulation as disclosed in the present invention.

EXAMPLE NO. 18

Emulsifying Process for Micelles Formation

An emulsion is a mixture of two or more immiscible (unblendable) liquids. One liquid (the dispersed phase) is dispersed in the other (the continuous phase). Many emulsions are oil/water emulsions, with dietary fats being one common type of oil encountered in everyday life. Examples of emulsions include butter and margarine, milk and cream, and vinaigrettes; the photo-sensitive side of photographic film, magmas and cutting fluid for metal working. In butter and margarine, fat surrounds droplets of water (a water-in-oil emulsion). In milk and cream, water surrounds droplets of fat (an oil-in-water emulsion). In certain types of magma, globules of liquid NiFe may be dispersed within a continuous phase of liquid silicates. Emulsification is the process by which emulsions are prepared.

Emulsions are thermodynamically unstable liquid/liquid dispersions that are stabilized, in general, by surfactants. Surfactants are usually added to emulsion systems, assembling in the interface of the emulsion droplets, thus providing a protective membrane that prevents the droplets from flocculating or coalescing and thus enhancing the droplets formation and stability. Emulsion dispersion is not about reactor blends for which one polymer is polymerized from its monomer in the presence of the other polymers; emulsion dispersion is a novel method of choice for the preparation of homogeneous blends of thermoplastic and elastomer. In emulsion dispersion system the preparation of well-fined polymers droplets maybe acquired by the use of water as dispersing medium. The surfactant molecules adsorb on the surface of emulsion by creating a dispersion of droplets, which reduces interfacial tension and retards particle flocculation during mixing. The molecules of surfactant have polar and non-polar parts which act as an intermediary to combine polar and non-polar polymers; the intermolecular interactions between the polar and the non-polar polymer segments resemble the macroscopic hydrocarbon-water interface.

Emulsions tend to have a cloudy appearance, because the many phase interfaces (the boundary between the phases is called the interface) scatter light that passes through the emulsion. Emulsions are unstable and thus do not form spontaneously. Energy input through shaking, stirring, homogenizing, or spray processes are needed to form an emulsion. Over time, emulsions tend to revert to the stable state of the phases comprising the emulsion. Surface-active substances (surfactants) can increase the kinetic stability of emulsions greatly so that, once formed, the emulsion does not change significantly over years of storage. Vinaigrette is an example of an unstable emulsion that will quickly separate unless shaken continuously. This phenomenon is called coalescence, and happens when small droplets recombine to form bigger ones.

Emulsions are part of a more general class of two-phase systems of matter called colloids. Although the terms colloid and emulsion are sometimes used interchangeably, emulsion tends to imply that both the dispersed and the continuous phase are liquid. There are three types of emulsion instability: floculation, where the particles form clumps; creaming, where the particles concentrate towards the surface (or bottom, depending on the relative density of the two phases) of the mixture while staying separated; and breaking and coalescence where the particles coalesce and form a layer of liquid. Whether an emulsion turns into a water-in-oil emulsion or an oil-in-water emulsion depends on the volume fraction of both phases and on the type of emulsifier. Generally, the Bancroft rule applies: emulsifiers and emulsifying particles tend to promote dispersion of the phase in which they do not dissolve very well; for example, proteins dissolve better in water than in oil and so tend to form oil-in-water emulsions (that is they promote the dispersion of oil droplets throughout a continuous phase of water).

The basic color of emulsions is white. If the emulsion is dilute, the Tyndall effect will scatter the light and distort the color to blue; if it is concentrated, the color will be distorted towards yellow. This phenomenon is easily observable on comparing skimmed milk (with no or little fat) to cream (high concentration of milk fat). Microemulsions and nanoemulsions tend to appear clear due to the small size of the disperse phase.

An emulsifier (also known as an emulgent) is a substance that stabilizes an emulsion, frequently a surfactant. Examples of food emulsifiers are egg yolk (where the main emulsifying chemical is lecithin), honey, and mustard, where a variety of chemicals in the mucilage surrounding the seed hull act as emulsifiers; proteins and low-molecular weight emulsifiers are common as well. In some cases, particles can stabilize emulsions as well through a mechanism called Pickering stabilization. Both mayonnaise and Hollandaise sauce are oil-in-water emulsions that are stabilized with egg yolk lecithin. Detergents are another class of surfactant, and will physically interact with both oil and water, thus stabilizing the interface between oil or water droplets in suspension. This principle is exploited in soap to remove grease for the purpose of cleaning. A wide variety of emulsifiers are used in pharmacy to prepare emulsions such as creams and lotions. Common examples include emulsifying was, cetearyl alcohol, polysorbate 20, and ceteareth 20.

Sometimes the inner phase itself can act as an emulsifier, and the result is nanoemulsion—the inner state disperses into nano-size droplets within the outer phase. A well-known example of this phenomenon, the ouzo effect, happens when water is poured in a strong alcoholic anize-based beverage, such as ouzo, pastis, arak or raki. The anisolic compounds, which are soluble in ethanol, now form nano-sized droplets and emulgate within the water. The color of such diluted drink is opaque and milky.

Microemulsions are clear, stable, isotropic liquid mixtures of oil, water and surfactant, frequently in combination with a cosurfactant. The aqueous phase may contain salt(s) and/or other ingredients, and the "oil" may actually be a complex mixture of different hydrocarbons and olefins. In contrast to ordinary emulsions, microemulsions form upon simple mixing of the components and do not require the high shear conditions generally used in the formation of ordinary emulsions. The two basic types of microemulsions are direct (oil dispersed in water, o/w) and reversed (water dispersed in oil, w/o). In ternary systems such as microemulsions, where two immiscible phases (water and 'oil') are present with a surfactant, the surfactant molecules may form a monolayer at the interface between the oil and water, with the hydrophobic tails of the surfactant molecules dissolved in the oil phase and the hydrophilic head groups in the aqueous phase. As in the binary systems (water/surfactant or oil/surfactant), self-assembled structures of different types can be formed, ranging, for example, from (inverted) spherical and cylindrical micelles to lamellar phases and discontinuous microemulsions, which may coexist with predominantly oil or aqueous phases.

The microemulsion region is usually characterized by constructing ternary-phase diagrams. Three components are the basic requirement to form a microemulsion: an oil phase, an aqueous phase and a surfactant. If a cosurfactant is used, it may sometimes be represented at a fixed ratio to surfactant as a single component, and treated as a single "pseudo-component". The relative amounts of these three components can be represented in a ternary phase diagram. Gibbs phase diagrams can be used to show the influence of changes in the volume fractions of the different phases on the phase behavior of the system. The three components composing the system are each found at an apex of the triangle, where their corresponding volume fraction is 100%. Moving away from that corner reduces the volume fraction of that specific component and increases the volume fraction of one or both of the two other components. Each point within the triangle represents a possible composition of a mixture of the three components or pseudo-components, which may consist (ideally, according to the Gibbs' phase rule) of one, two or three phases. These points combine to form regions with boundaries between them, which represent the "phase behavior" of the system at constant temperature and pressure.

Some aspects of the invention provide a formulation of liposome micelles and methods of formulating micelles, the micelles comprising a basic structure as described above and at least one compound or agent enclosed within. In one embodiment, the compound can be a thermal triggered phase-transition compound. In another embodiment, the agent can be hydrophobic or lipophilic agent. In another embodiment, the agent can be a cancer drug. In general, the micelles of the present invention may also be referred as 'bioactive micelles'. The micelles are generally less than about a few hundred nanometers, preferably less than about 20 nanometers, and most preferably less than about 10 nanometers.

Liposomes are artificially prepared vesicles made of lipid bilayer. Liposomes can be filled with drugs, and used to deliver drugs for cancer and other disease. Liposomes can be prepared by disrupting biological membranes, for example by sonication. Liposomes can be composed of naturally-derived phospholipids with mixed lipid chains (like egg phosphatidylethanolamine) or other surfactants. Liposomes should not be confused with micelles and reverse micelles composed of monolayers. Liposomes are composite structures made of phospholipids and may contain small amounts of other molecules. Though liposomes can vary in size from low micrometer range to tens of micrometers, unilamellar liposomes are typically in the lower size range with various targeting ligands attached to their surface allowing for their surface-attachment and accumulation in pathological areas for treatment of disease. Another interesting property of liposomes is their natural ability to target cancer. The endothelial wall of all healthy human blood vessels is encapsulated by endothelial cells that are bound together by tight junctions. These tight junctions stop any large particles in the blood from leaking out of the vessel. Tumor vessels do not contain the same level of seal between cells and are diagnostically leaky. This ability is known as the Enhanced Permeability and Retention effect. Liposomes of certain sizes, typically less than about 200 nm, can rapidly enter tumor sites from the blood, but are kept in the bloodstream by the endothelial wall in healthy tissue vasculature. Anticancer drugs such as Doxorubicin (Doxil), Camptothecin and Daunorubicin (Daunoxome) are currently being marketed in liposome delivery systems. The thermal triggered phase-transition compound inside a liposome delivery system, after entering a cancer cell, functions to abruptly blow up the cancer cell for physical cancer therapy.

Formation of liposomes and nanoliposomes is not a spontaneous process. Lipid vesicles are formed when phospholipids such as lecithin are placed in water and consequently form one bilayer or a series of bilayers, each separated by water molecules, once enough energy is supplied. Liposomes can be created by sonicating phospholipids in water. Low shear rates create multilamellar liposomes, which have many layers like an onion. Continued high-shear sonication tends to form smaller unilamellar liposomes. In this technique, the liposome contents are the same as the contents of the aqueous phase. Sonication is generally considered a "gross" method of preparation as it can damage the structure of the drug to be encapsulated. Newer methods such as extrusion and Mozafari method are employed to produce materials for human use.

Figure 15:
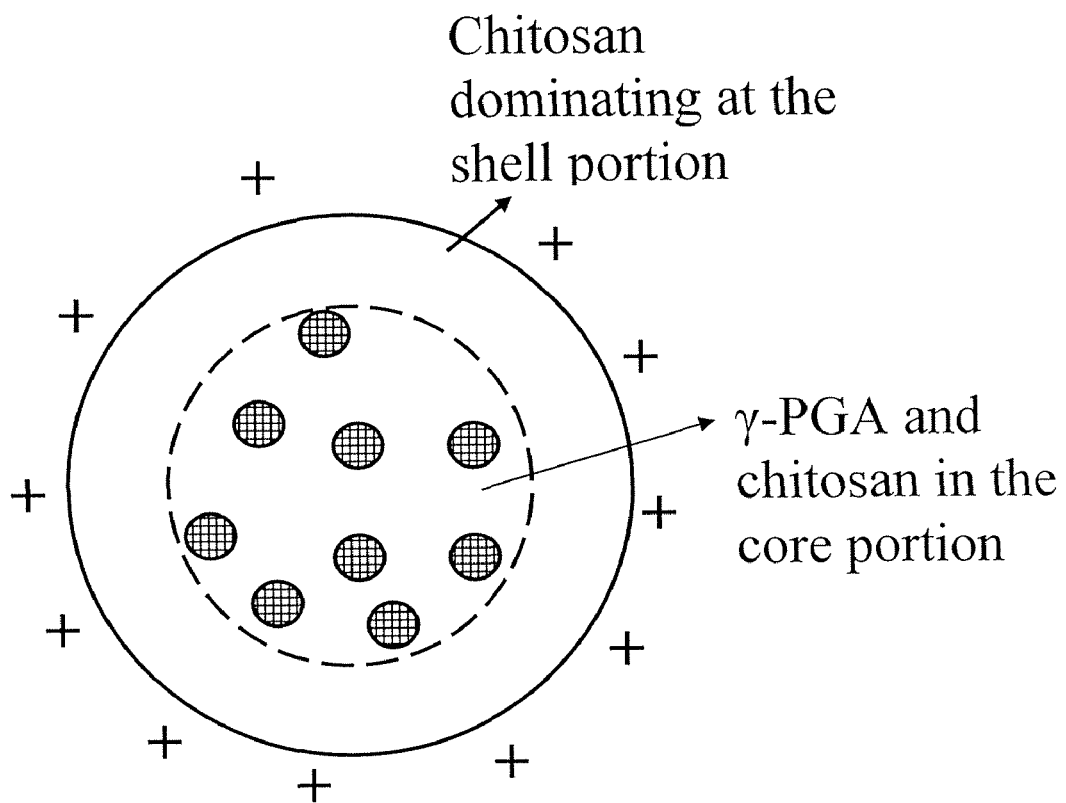
FIG. 15 shows a CS-γ-PGA chitosan-shelled nanoparticle having positive surface charges and at least one thermal triggered phase-transition compound (the bioactive agent) being associated in micelles before being encapsulated in nanoparticles.

Some aspects of the invention provide a pharmaceutical composition of nanoparticles, the nanoparticles consisting of a positively charged chitosan, a negatively charged substrate, optionally a zero-charge compound, and liposome micelles. FIG. 15 shows a CS-γ-PGA chitosan-shelled nanoparticle having positive surface charges and the bioactive agent (a thermal triggered phase-transition compound) being associated in micelles before being encapsulated in nanoparticles.

EXAMPLE NO. 19

Thermal Triggerable Phase-Transition Liposomes for Physical Cancer Therapy

Liposome micelles are manufactured by mixing a thermal triggered phase-transition compound (e.g., ammonium bicarbonate or other suitable compound) into liposome material. In one embodiment, the liposome material is comprised of HSPC (L-α-phosphatidylcholine, hydrogenated), which is a non-thermal responsible material serving as the base forming material, DOTMA (N-[1-(2,3-dioleyloxy)propyl]-N,N,N-trimethylammonium chloride) as an enhancer to increase cell uptake, and/or cholesterol ((10R,13R)-10,13-dimethyl-17-(6-methylheptan-2-yl)-2,3,4,7,8,9,11,12,14,15,16,17-dodecahydro-1H-cyclopenta [α]phenanthren-3-ol) as a stabilizer for liposome. In one exemplary embodiment, the molar ratio of HSPC:cholesterol:DOTMA of the liposome material is in the range of 6:4:0.5. The external surface of liposome micelles of the invention may be positive charged and have an average size of about 300 nm.

At room temperature, ammonium bicarbonate is a white, crystalline powder. Ammonium bicarbonate decomposes at 36 to 60° C. into ammonia, carbon dioxide, and water vapor in an endothermic process with rapid volume increase as shown below:

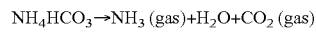

$$NH_4HCO_3 \rightarrow NH_3 \text{ (gas)} + H_2O + CO_2 \text{ (gas)}$$

The average liposome nanoparticle has been shown to be about 1200 nm after rapid decomposition of ammonium bicarbonate inside the nanoparticle; though the exploded nanoparticle is no longer in perfect spherical shapes. In one embodiment, the ammonium bicarbonate compound in the liposome nanoparticle formulation is a solid compound. Other thermal triggered phase-transition biocompatible compounds (for example, ammonium carbonate, ammonium sesquecarbonate, and the like) may be used in this liposome particle formulation. As used herein, the phrase "a thermal triggered phase-transition compound" means a temperature sensitive gaseous precursor, which denotes a solid or liquid compound that forms a gas following a change in temperature. In one embodiment, the compound may include the sublimable compound, wherein sublimation is the transition of a substance from the solid phase to the gas phase without passing through an intermediate liquid phase. Sublimation requires additional energy and is an endothermic change.

Figure 19:
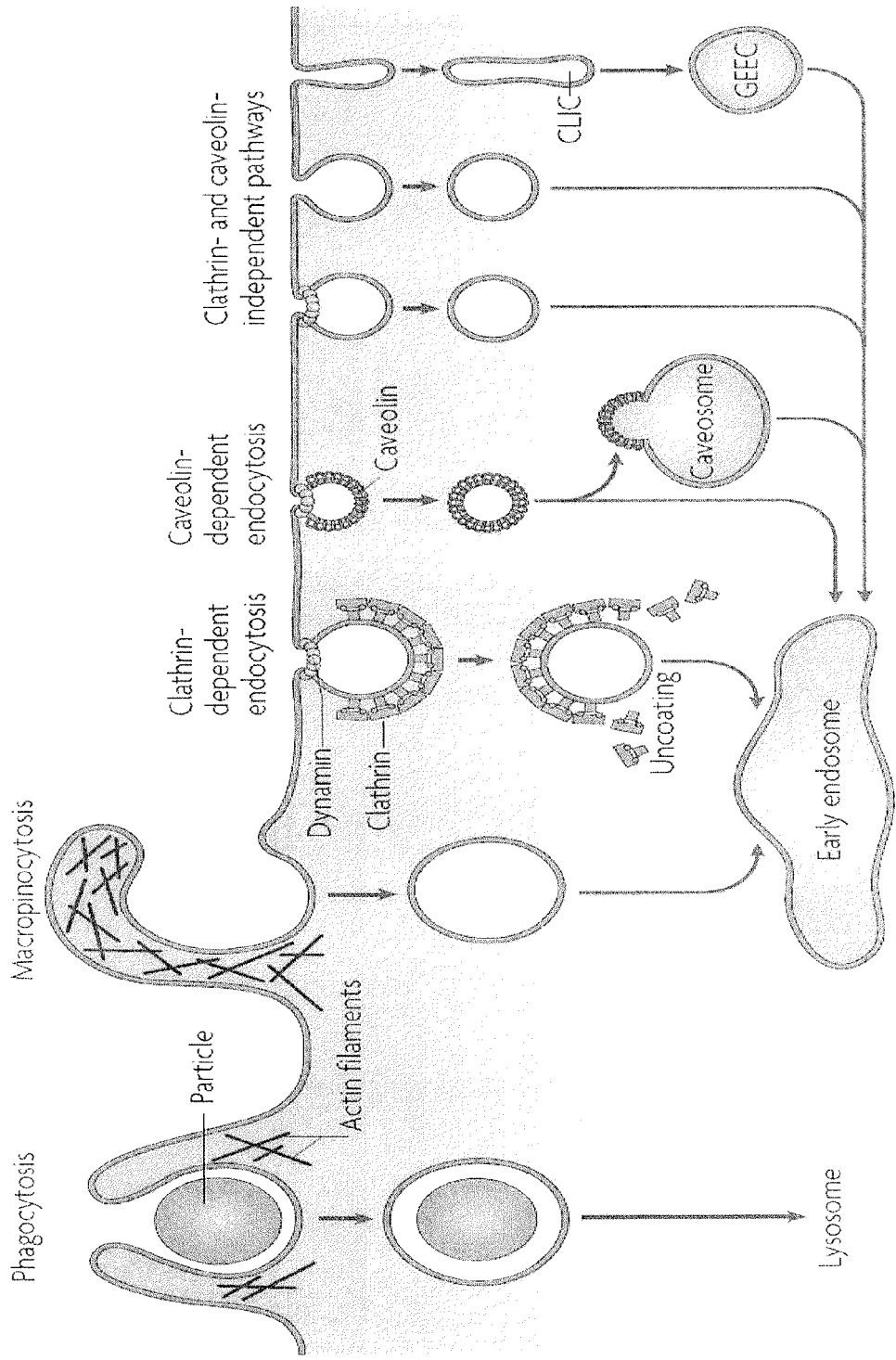
FIG. 19 shows proposed endocytosis pathways for liposome micelles or nanoparticles uptake.

Some aspects of the invention relate to a pharmaceutical composition of liposome nanoparticles composed of at least one thermal triggered or triggerable phase-transition compound and at least one cancer drug. In clinical applications, the liposome nanoparticles are benign to a body as long as the liposome shell is intact. The term "thermal triggerable" is meant to indicate 'being able to be triggered thermally'. After the liposome nanoparticles are delivered to an animal subject following one of proposed endocytosis pathways (see FIG. 19, sources: *Nature Cell Biology Letter* 1 (2006)), some nanoparticles are heated to trigger phase transition of the loaded phase-transition compound and to cause physical damage of cancer cells as means for physical cancer therapy. Furthermore, the liposome nanoparticles may further comprise a cancer drug as means for a dual physical and biochemical cancer treatment.

The energy source for causing the phase transition of the enclosed 'at least one thermal triggered phase-transition compound' can be supplied from outside the animal subject toward the cancer or tumor cells. In one embodiment, the energy is applied via a radiofrequency catheter that contacts the target cancer cells in situ. In another embodiment, the ultrasound energy is applied through an intravascular ultrasound catheter. In another embodiment, the energy is provided via an external ultrasound system as a result of the ultrasound-induced hyperthermia, particularly with a high-intensity focused ultrasound (HIFU), toward the cancer cells. HIFU is a highly precise medical procedure using high-intensity focused ultrasound to heat and destroy pathogenic tissue rapidly. It is one modality of therapeutic ultrasound, and, although it induces hyperthermia, it should not be confused with this technique, which heats much less rapidly and to much lower therapeutic temperatures (in general <45° C.). In still another embodiment, the energy can be supplied via electromagnetic means toward the phase-transition compound from outside the animal subject. In an alternate embodiment, iron-containing quantum dots or tiny particles may be encapsulated within the liposome particles of the present invention. An external ultrasonic energy source could be applied to the iron-containing particles to provide heat to the phase-transition compound for blowing up the cancer cells. In one embodiment, the energy is supplied via hot or warm saline.

In one embodiment, the liposome portion of the liposome nanoparticles is less thermal sensitive than the thermal triggerable phase-change compound of the liposome nanoparticles. In another embodiment, the thermal energy source for causing the phase transition of the encapsulated 'at least one thermal triggered phase-transition compound' is configured to be insufficient to cause any thermal damage to the liposome portion of the liposome nanoparticles of the present invention.

Some aspects of the invention relate to a pharmaceutical composition of liposome nanoparticles composed of at least one thermal triggered or triggerable phase-transition compound and at least one cancer targeting moiety as means for a dual function of cell targeting and physical cancer therapy.

Some aspects of the invention relate to a method of cell treating a cancer or tumor cell of an animal subject, comprising steps of: (a) providing a pharmaceutical composition of nanoparticles, wherein the nanoparticles comprise liposome and at least one thermal triggered phase-transition compound; (b) lodging the nanoparticles in the cancer or tumor cell in situ of the animal subject; and (c) supplying thermal energy to the at least one thermal triggered phase-transition compound, wherein the thermal energy is sufficient to cause a phase transition of the thermal triggered phase-transition compound. In one embodiment, the cell is a liver cell. In another embodiment, at least a portion of the nanoparticles comprises a hydrophilic outer shell, a hydrophobic outer shell or a bilayer.

Some aspects of the invention provide a method of cell treatment in an animal subject, comprising steps of: (a) providing a pharmaceutical composition of nanoparticles, wherein the nanoparticles comprise liposome and at least one thermal triggerable phase-transition compound; (b) lodging the nanoparticles in the cell in situ of the animal subject; and (c) supplying thermal energy to the at least one thermal triggerable phase-transition compound, wherein the thermal energy is sufficient to cause a phase transition of the thermal triggerable phase-transition compound.

Some aspects of the invention relate to a method of treating a cancer or tumor cell by providing a pharmaceutical composition of liposome nanoparticles of the present invention to an animal subject, wherein nanoparticles are further loaded with at least one bioactive agent. In one embodiment, the at least one bioactive agent is an anticancer or antitumor drug, paclitaxel, a chemotherapy component, a deoxyribonucleic acid, or a small interfering ribonucleic acid.

pH and Temperature Sensitive Liposomes

Liposome delivery systems offer the potential to enhance the therapeutic index of anticancer drugs, either by increasing the drug concentration in tumor cells or by decreasing the exposure in normal host tissues. Long-circulating pegylated liposomal DOX (Doxil®/Caelyx®) have been shown to result in increased accumulation of drug in solid tumors and minimizes the acute cardiotoxicity associated with free DOX. The Doxil® formulation is the first approved nanomedicine for cancer therapy and is clinically indicated for Kaposi sarcoma, multiple myeloma and advanced ovarian cancer. Despite the prolonged circulation time and increased tumor accumulation, slow and passive drug release from these liposomes hinders an optimal antitumor effect (<5% in 24 h). It is clinical relevant to design a liposomal carrier which can be triggered to release encapsulated contents.

Figure 20:
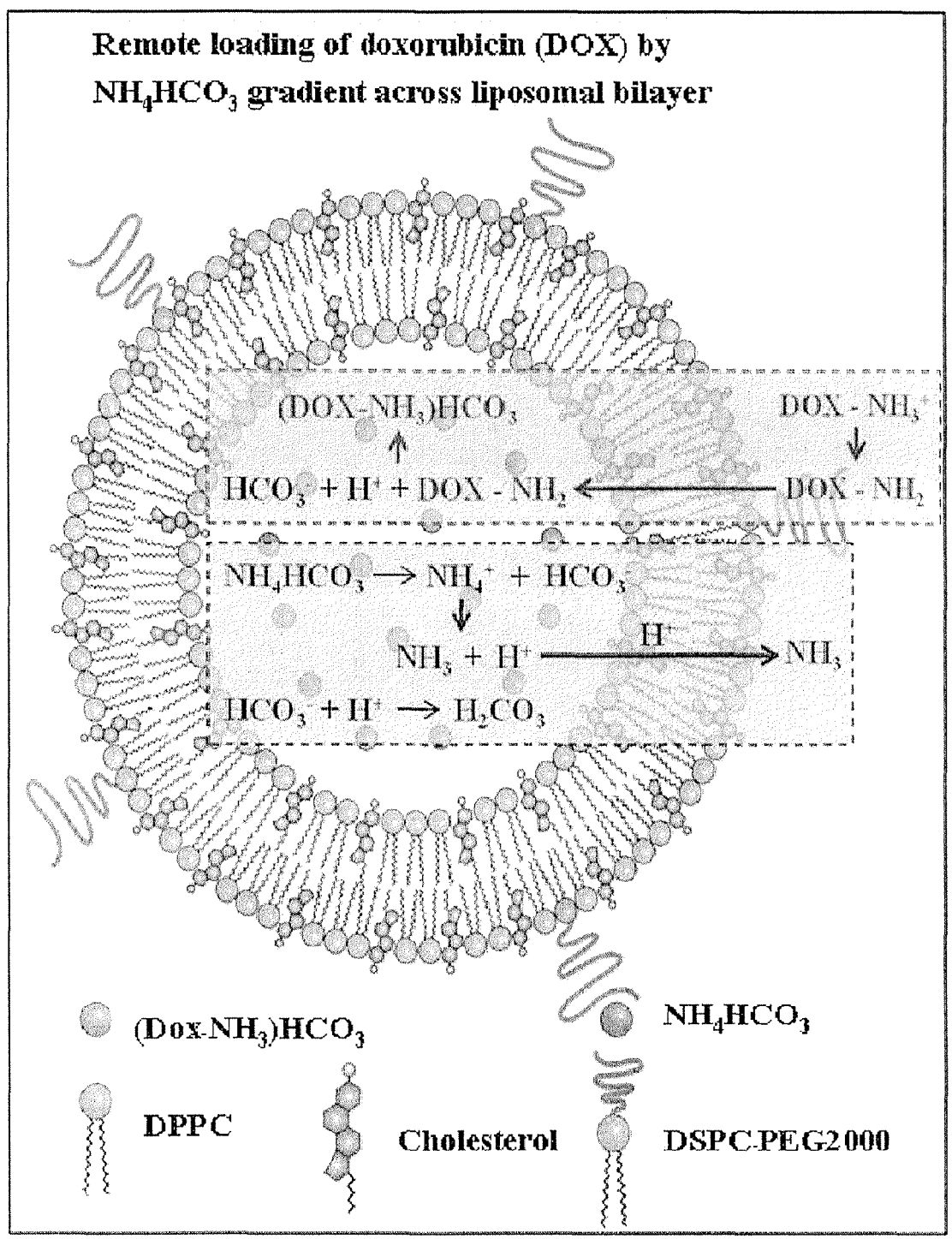
FIG. 20 shows schematic of remote loading of doxorubicin by ammonium bicarbonate gradient across liposomal bilayer.
Figure 21:
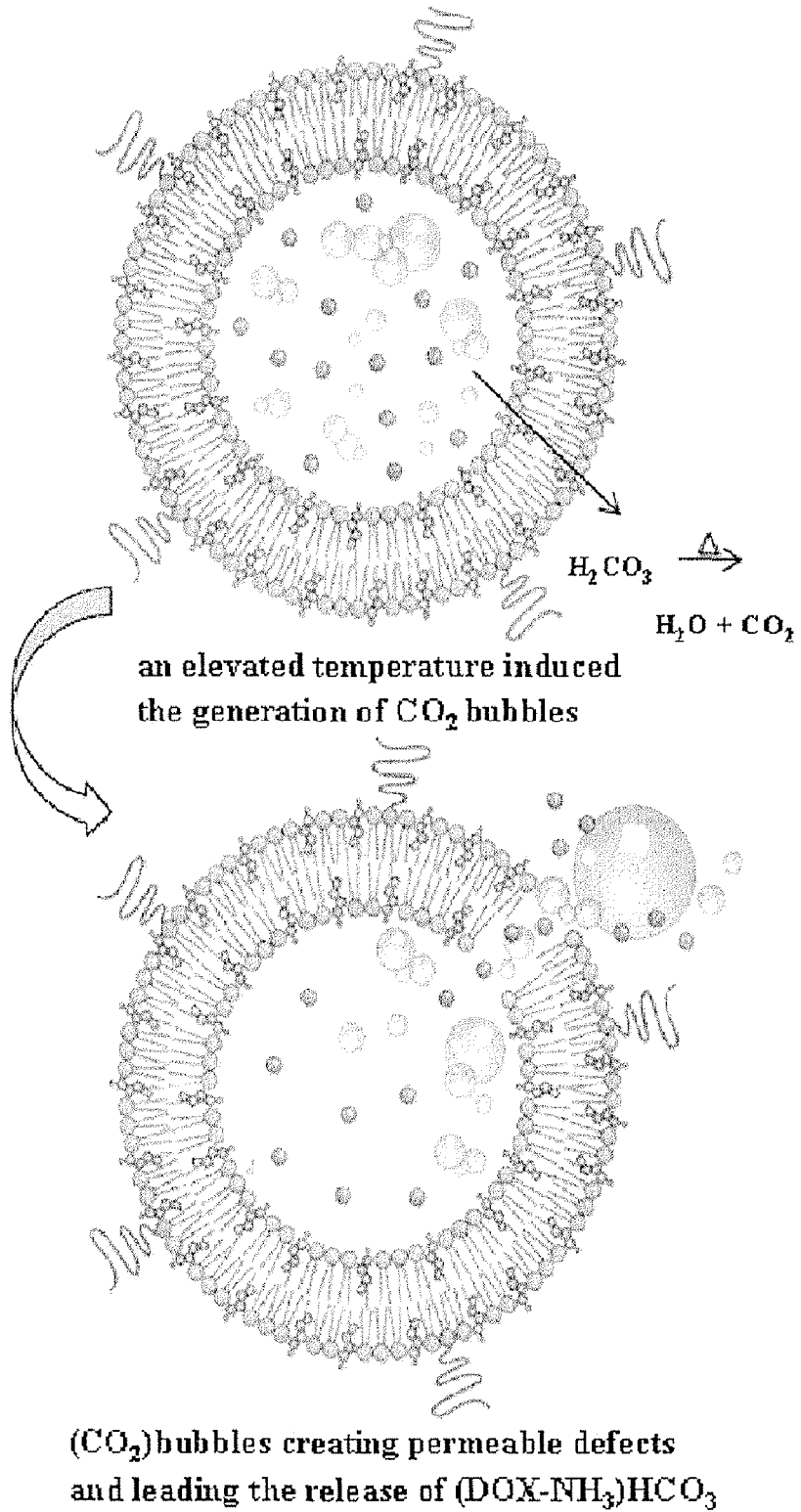
FIG. 21 shows schematic of hyperthermia-induced drug release mechanism.

One triggering mechanism to effect changes in local microenvironment is known as thermosensitive liposomes (TSLs), which maintains the drug within the liposome during blood transport (~37° C.), and release their payload in regions where local tissue temperatures are elevated (about 40-42° C.), permitting their combination with an external source of hyperthermia for improved local drug delivery. Another triggering mechanism to effect change in local microenvironment is known as pH-sensitive liposomes. A DOX loaded liposomal system incorporated ammonium bicarbonate ($NH_4HCO_3$, ABC) (DOX-ABC liposomes) was disclosed. An active liposome DOX loading process could be promoted by creating an ammonium ($NH_4^+$) gradient between internal and external aqueous phase of liposome. And an elevated temperature (40-42° C.) can stimulated the internal bicarbonate ($HCO_3^-$) to generate carbon dioxide ($CO_2$) bubbles, creating permeable defects in the bilayer and thereby swiftly releasing DOX (FIGS. 20 and 21).

The liposomes were prepared by lipid film hydration followed by sequential extrusion. DOX was encapsulated into the liposomes by remote loading using an ammonium ($NH_4^+$) gradient. Briefly, the liposome suspension and DOX was mixed at 0.1, 0.05 or 0.02 (drug/lipid (w/w)), and the mixture was maintained at room temperature for 24 h. Unloaded DOX was removed by passing the suspension through a Sephadex G-50 column (GE Healthcare, Buckinghashire, UK) eluted with 10 wt % sucrose solution. The $NH_4HCO_3$ gradient is formed by lowering the $NH_4^+$ concentration on the outside of liposome, and the transmembrane equilibrium was create by removing and leaving behind a proton $H^+$, this results in active loading of DOX. As shown in FIG. 20, the unprotonated form of DOX ($DOX-NH_2$) enters the inside of the liposome water phase, becomes protonated ($DOX-NH_3^+$), and reacts with $HCO_3^-$ to form a divalent DOX-bicarbonate salt (($DOX-NH_3$)$HCO_3$).

Other versions of ammonium-based gradients, such as $(NH_4)_2SO_4$, ammonium citrate and ammonium acetate, have also been successfully demonstrated with the above-referred method. And the hyperthermia-induced drug release mechanism is presented as the internal $HCO_3^-$ of liposome, which can be stimulated to generate $CO_2$ bubbles under hyperthermia temperatures (above 40° C. or above about 40° C.) rapidly, causing permeable defects in the bilayer membrane due to the increase in internal pressure, and thereby swiftly releasing DOX (FIG. 21). In one embodiment, the liposome nanoparticles of the present invention is applicable to those clinically approved liposomal drugs, for example, Liposomal amphotericin B. Liposomal cytarabine, Liposomal daunorubicin, Liposomal doxorubicin, Liposomal IRIV vaccine, Liposomal morphine, Liposomal verteporfin, Liposomal estradiol, Liposome-PEG doxorubicin, and the like.

Clathrin is a protein that plays a major role in the formation of coated vesicles, such as micelles, liposomes, or nanoparticles. Clathrin forms a triskelion shape composed of three clathrin heavy chains and three light chains. When the triskelia interact they form a polyhedral lattice that surrounds the vesicle. Coat-proteins, like clathrin, are used to build small vesicles in order to safely transport molecules between cells. The endocytosis and exocytosis of vesicles allows cells to transfer nutrients, to import signaling receptors, to mediate an immune response after sampling the extracellular world, and to clean up the cell debris left by tissue inflammation. On occasion, this mechanism also provides a pathway for raiding pathogens or toxins. Clathrin offers many new and interesting possibilities for delivering drugs and medical imaging agents into the brain. Clathrin-directed nanoparticles were able to cross the blood-brain barrier or tight junctions noninvasively. Some aspects of the invention relate to nanoparticles, liposomes, micelles, or vesicles having clathrin as a targeting agent, thus forming clathrin-directed nanoparticles.

Like many proteins, clathrin represents a perfect case of form following function; it performs critical roles in shaping rounded vesicles in the cytoplasm for intracellular trafficking. Clathrin-coated vesicles (CCV) selectively sort cargo at the cell membrane, trans-Golgi network, and endosomal compartments for multiple membrane traffic pathways. After a vesicle buds into the cytoplasm, the coat rapidly disassembles, allowing the clathrin to recycle while the vesicle gets transported to a variety of locations. Adaptor molecules are responsible for self-assembly and recruitment. Clathrin-mediated endocytosis regulates many cellular physiological processes such as the internalization of growth factors and receptors, entry of pathogens, and synaptic transmission. It is believed that cellular invaders use the nutrient pathway to gain access to a cell's replicating mechanisms. Certain signaling molecules open the nutrients pathway. Two chemical compounds called Pitstop 1 and Pitstop 2, selective clathrin inhibitors, can interfere with the pathogenic activity, and thus protect the cells against invasion. These two compounds selectively block the endocytic ligand association with the clathrin terminal domain.

Clathrin has another function aside from the coating of organelles. In non-dividing cells, the formation of clathrin-coated vesicles occurs continuously. Formation of clathrin-coated vesicles is shut down in cells undergoing mitosis. During mitosis, clathrin binds to the spindle apparatus. Clathrin aids in the congression of chromosomes by stabilizing fibers of the mitotic spindle. Clathrin is bound directly through the amino-terminal domain of the clathrin heavy chain. During mitosis the clathrin binds directly to the microtubules or microtubule-associated proteins. The stabilization of kinetochore fibers requires the trimetric structure of clathrin in order to strengthen the spindle fibers. Some aspects of the invention relate to a composition of nanoparticles or liposomal nanoparticles, comprising clathrin, at least one bioactive agent, and a thermal triggerable phase-transition compound, wherein said thermal triggerable phase-transition compound is selected from the group consisting of ammonium bicarbonate, ammonium sulfate, ammonium citrate, ammonium acetate, ammonium carbonate, and ammonium sesquecarbonate. In one embodiment, the clathrin-loaded nanoparticles are administered into an animal subject via a parenteral route, optionally passing through blood-brain barrier of the subject to deliver the at least one bioactive agent to brains.

Although the present invention has been described with reference to specific details of certain embodiments thereof, it is not intended that such details should be regarded as limitations upon the scope of the invention except as and to the extent that they are included in the accompanying claims. Many modifications and variations are possible in light of the above disclosure.

What is claimed is:

1. A composition of liposomes, comprising at least one antitumor or anticancer agent and a thermal triggerable phase-transitional compound, wherein said thermal triggerable phase-transitional compound is selected from the group consisting of ammonium bicarbonate, ammonium sulfate, ammonium citrate, ammonium acetate, ammonium carbonate, and ammonium sesquecarbonate, and wherein a temperature above 40° C. is provided to induce said compound to decompose and release carbon dioxide.

2. The composition according to claim 1, wherein the liposomes comprises HSPC (L-α-phosphatidylcholine, hydrogenated), DOTMA (N-[1-(2,3-dioleyloxy)propyl]-N,N,N-trimethylammonium chloride), and cholesterol.

3. The composition according to claim 1, wherein at least a portion of the liposomes comprises a hydrophilic outer shell.

4. The composition according to claim 1, wherein at least a portion of the liposomes comprises a hydrophobic outer shell.

5. The composition according to claim 1, wherein said liposomes are adapted for delivery to a blood vessel of an animal subject.

6. The composition according to claim 5, wherein said liposomes, enter cells of the animal subject via an endocytosis pathway.

7. The composition according to claim 1, wherein said at least one antitumor or anticancer agent is paclitaxel.

8. The composition according to claim 1, wherein said at least one antitumor or anticancer agent is a chemotherapy component.

9. The composition according to claim 1, wherein said liposomes further comprise a cancer targeting moiety.

10. The composition according to claim 1, wherein said liposomes further comprise a deoxyribonucleic acid.

11. The composition according to claim 1 wherein said liposomes further comprise a small interfering ribonucleic acid.

12. The composition according to claim 1, wherein said at least one antitumor or anticancer agent is loaded into said liposomes via a concentration gradient of said compound across a liposomal layer of said liposomes.

13. The composition according to claim 1, wherein said compound has a phase-transitional temperature below 60° C.

14. The composition according to claim 13, wherein thermal energy is supplied to raise temperature of said compound inside the liposomes.

15. The composition according to claim 14, wherein the thermal energy is supplied via a source selected from the group consisting of radiofrequency energy, ultrasonic energy, high-intensity focused ultrasound energy, electromagnetic energy, and hot saline energy.

16. The composition according to claim 15, wherein a duration of the thermal energy supplied to said compound is within 30 minutes.

17. The composition according to claim 1, wherein said compound is a sublimable compound.

18. The composition according to claim 1, wherein said at least one antitumor or anticancer drug is doxorubicin, camptothecin, or daunorubicin.

19. The composition according to claim 1, wherein the liposomes have a size less than about 300 nanometers.

* * * * *